(12) United States Patent
Van Berkel et al.

(10) Patent No.: US 11,059,893 B2
(45) Date of Patent: Jul. 13, 2021

(54) HUMANIZED ANTI-AXL ANTIBODIES

(71) Applicant: BERGENBIO ASA, Bergen (NO)

(72) Inventors: Patricius Hendrikus Cornelis Van Berkel, Lausanne (CH); David G. Williams, Epson (GB)

(73) Assignee: BERGENBIO ASA, Bergen (NO)

( * ) Notice: Subject to any disclaimer, the term of this patent is extended or adjusted under 35 U.S.C. 154(b) by 195 days.

(21) Appl. No.: 15/566,635

(22) PCT Filed: Apr. 15, 2016

(86) PCT No.: PCT/EP2016/058368
§ 371 (c)(1),
(2) Date: Oct. 13, 2017

(87) PCT Pub. No.: WO2016/166296
PCT Pub. Date: Oct. 20, 2016

(65) Prior Publication Data
US 2019/0352407 A1 Nov. 21, 2019

(30) Foreign Application Priority Data
Apr. 15, 2015 (GB) .................................. 1506411

(51) Int. Cl.
*C07K 16/00* (2006.01)
*C07K 16/28* (2006.01)

(52) U.S. Cl.
CPC ...... *C07K 16/2863* (2013.01); *C07K 2317/24* (2013.01); *C07K 2317/76* (2013.01); *C07K 2317/92* (2013.01); *C07K 2317/94* (2013.01)

(58) Field of Classification Search
CPC ............ C07K 16/2863; C07K 2317/24; C07K 2317/76; C07K 2317/92; C07K 2317/94
See application file for complete search history.

(56) References Cited

U.S. PATENT DOCUMENTS

| | | | |
|---|---|---|---|
| 3,361,742 A | 1/1968 | Julius et al. |
| 3,523,941 A | 8/1970 | Leimgruber et al. |
| 3,524,849 A | 8/1970 | Batcho et al. |
| 3,794,644 A | 2/1974 | Karlyone et al. |
| 4,185,016 A | 1/1980 | Takanabe et al. |
| 4,239,683 A | 12/1980 | Takanabe et al. |
| 4,309,437 A | 1/1982 | Ueda et al. |
| 4,353,827 A | 10/1982 | Hunkeler et al. |
| 4,382,032 A | 5/1983 | Hunkeler et al. |
| 4,386,028 A | 5/1983 | Hunkeler et al. |
| 4,405,516 A | 9/1983 | Hunkeler et al. |
| 4,405,517 A | 9/1983 | Hunkeler et al. |
| 4,407,752 A | 10/1983 | Hunkeler et al. |
| 4,427,587 A | 1/1984 | Kaneko et al. |
| 4,427,588 A | 1/1984 | Kaneko et al. |
| 4,701,325 A | 10/1987 | Ueda et al. |
| 4,816,567 A | 3/1989 | Cabilly et al. |
| 4,923,984 A | 5/1990 | Matsumura et al. |
| 4,923,990 A | 5/1990 | Nakano et al. |
| 5,362,852 A | 11/1994 | Geoghegan |
| 5,418,241 A | 5/1995 | Jegham et al. |
| 5,440,021 A | 8/1995 | Chuntharapai et al. |
| 5,468,634 A | 11/1995 | Liu |
| 5,538,861 A | 7/1996 | Scheider et al. |
| 5,583,024 A | 12/1996 | McElroy et al. |
| 5,621,002 A | 4/1997 | Bosslet et al. |
| 5,644,033 A | 7/1997 | Seon |
| 5,674,713 A | 10/1997 | McElroy et al. |
| 5,700,670 A | 12/1997 | Yamagishi et al. |
| 5,773,223 A | 6/1998 | Shyamala et al. |
| 5,792,616 A | 8/1998 | Persico et al. |
| 5,854,399 A | 12/1998 | Salomon et al. |
| 5,869,445 A | 2/1999 | Cheever et al. |
| 5,968,508 A | 10/1999 | Goldfine et al. |
| 5,976,551 A | 11/1999 | Mottez et al. |
| 6,011,146 A | 1/2000 | Mottez et al. |
| 6,087,144 A | 7/2000 | Scadden |
| 6,153,408 A | 11/2000 | Abastado et al. |
| 6,211,142 B1 | 4/2001 | Hammonds et al. |
| 6,214,345 B1 | 4/2001 | Firestone et al. |
| 6,218,519 B1 | 4/2001 | Kenten et al. |
| 6,235,769 B1 | 5/2001 | Clary et al. |
| 6,268,488 B1 | 7/2001 | Barbas, III et al. |
| 6,362,331 B1 | 3/2002 | Kamal et al. |
| 6,518,404 B1 | 2/2003 | Li et al. |
| 6,534,482 B1 | 3/2003 | Fikes et al. |
| 6,555,339 B1 | 4/2003 | Liaw et al. |
| 6,562,806 B1 | 5/2003 | Thurston et al. |
| 6,602,677 B1 | 8/2003 | Wood et al. |
| 6,608,192 B1 | 8/2003 | Thurston et al. |
| 6,660,742 B2 | 12/2003 | Lee |

(Continued)

FOREIGN PATENT DOCUMENTS

| EP | 0522868 | 1/1993 |
|---|---|---|
| EP | 0875569 | 11/1998 |

(Continued)

OTHER PUBLICATIONS

Paul, Fundamental Immunology, 3rd Edition, 1993, pp. 292-295 (Year: 1993).*
Rudikoffetal., (Proc. Natl. Acad. Sci. USA 1982 vol. 79: p. 1979) (Year: 1982).*
Cassetetal (BBRC 307, 198-205 2003) (Year: 2003).*
Pascalis et al (The Journal of Immunology vol. 169, 3076-3084, 2002 (Year: 2002).*
"Mus musculus isolate 26 immunoglobulin V kappa light chain mRNA, partial cds," NCBI Accession No. GU563184, 1 page, 2010.
Ben-Batalla; et al., "Axl, a prognostic and therapeutic target in acute myeloid leukemia mediates paracrine crosstalk of leukemia cells with bone marrow stroma." Blood. Oct. 3, 2013; 122(14):2443-52.
Byers; et al., "An epithelial-mesenchymal transition gene signature predicts resistance to EGFR and PI3K inhibitors and identifies Axl as a therapeutic target for overcoming EGFR inhibitor resistance." Clin Cancer Res. Jan. 1, 2013; 19(1):279-90.

(Continued)

*Primary Examiner* — Lei Yao
(74) *Attorney, Agent, or Firm* — Casimir Jones, S.C.; Melissa E. Karabinis

(57) ABSTRACT

The present disclosure relates to humanized anti-Axl antibodies.

11 Claims, 3 Drawing Sheets

Specification includes a Sequence Listing.

(56) References Cited

U.S. PATENT DOCUMENTS

| | | |
|---|---|---|
| 6,660,856 B2 | 12/2003 | Wang |
| 6,677,435 B2 | 1/2004 | Barbas, III et al. |
| 6,747,144 B1 | 6/2004 | Thurston et al. |
| 6,759,509 B1 | 7/2004 | King et al. |
| 6,835,807 B1 | 12/2004 | Sasaki et al. |
| 6,884,799 B2 | 4/2005 | Kamal et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,223,837 B2 | 5/2007 | De Groot et al. |
| 7,244,724 B2 | 7/2007 | Liu et al. |
| 7,265,105 B2 | 9/2007 | Thurston et al. |
| 7,375,078 B2 | 5/2008 | Feng |
| 7,407,951 B2 | 8/2008 | Thurston et al. |
| 7,429,658 B2 | 9/2008 | Howard et al. |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,528,126 B2 | 5/2009 | Howard et al. |
| 7,557,099 B2 | 7/2009 | Howard et al. |
| 7,612,062 B2 | 11/2009 | Gregson et al. |
| 7,704,924 B2 | 4/2010 | Thurston et al. |
| 7,723,485 B2 | 5/2010 | Junutula et al. |
| 7,741,319 B2 | 6/2010 | Howard et al. |
| 8,034,808 B2 | 11/2011 | Delavault et al. |
| 8,163,736 B2 | 4/2012 | Gauzy et al. |
| 8,487,092 B2 | 7/2013 | Howard et al. |
| 8,501,934 B2 | 8/2013 | Howard et al. |
| 8,592,576 B2 | 11/2013 | Howard et al. |
| 8,609,089 B2 | 12/2013 | Langermann |
| 8,633,185 B2 | 1/2014 | Howard et al. |
| 8,637,664 B2 | 1/2014 | Howard et al. |
| 8,697,688 B2 | 4/2014 | Howard et al. |
| 8,735,553 B1 | 5/2014 | Li et al. |
| 8,829,184 B2 | 9/2014 | Howard et al. |
| 8,940,733 B2 | 1/2015 | Howard et al. |
| 9,321,774 B2 | 4/2016 | Howard et al. |
| 9,376,440 B2 | 6/2016 | Howard et al. |
| 9,399,641 B2 | 7/2016 | Howard et al. |
| 9,624,227 B2 | 4/2017 | Howard et al. |
| 9,889,207 B2 | 2/2018 | Howard |
| 2001/0055751 A1 | 12/2001 | Reiter et al. |
| 2002/0034749 A1 | 3/2002 | Billing-Medel et al. |
| 2002/0042366 A1 | 4/2002 | Thompson et al. |
| 2002/0150573 A1 | 10/2002 | Nussenzweig |
| 2002/0193567 A1 | 12/2002 | Jacobs et al. |
| 2003/0060612 A1 | 3/2003 | Goddard et al. |
| 2003/0062401 A1 | 4/2003 | Hasz et al. |
| 2003/0064397 A1 | 4/2003 | Spancake et al. |
| 2003/0065143 A1 | 4/2003 | Eaton et al. |
| 2003/0091580 A1 | 5/2003 | Mitcham et al. |
| 2003/0096743 A1 | 5/2003 | Senter et al. |
| 2003/0096961 A1 | 5/2003 | Baker et al. |
| 2003/0105292 A1 | 6/2003 | Liaw et al. |
| 2003/0109676 A1 | 6/2003 | Li et al. |
| 2003/0118592 A1 | 6/2003 | Ledbetter et al. |
| 2003/0119121 A1 | 6/2003 | Baker et al. |
| 2003/0119122 A1 | 6/2003 | Baker et al. |
| 2003/0119125 A1 | 6/2003 | Baker et al. |
| 2003/0119126 A1 | 6/2003 | Baker et al. |
| 2003/0119128 A1 | 6/2003 | Baker et al. |
| 2003/0119129 A1 | 6/2003 | Baker et al. |
| 2003/0119130 A1 | 6/2003 | Baker et al. |
| 2003/0119131 A1 | 6/2003 | Baker et al. |
| 2003/0124140 A1 | 7/2003 | Bangur et al. |
| 2003/0124579 A1 | 7/2003 | Mack et al. |
| 2003/0129192 A1 | 7/2003 | Chenault et al. |
| 2003/0130189 A1 | 7/2003 | Senter et al. |
| 2003/0134790 A1 | 7/2003 | Langenfeld |
| 2003/0143557 A1 | 7/2003 | Penner |
| 2003/0157089 A1 | 8/2003 | Xu et al. |
| 2003/0165504 A1 | 9/2003 | Retter et al. |
| 2003/0185830 A1 | 10/2003 | Xu et al. |
| 2003/0186372 A1 | 10/2003 | Baker et al. |
| 2003/0186373 A1 | 10/2003 | Baker et al. |
| 2003/0194704 A1 | 10/2003 | Penn et al. |
| 2003/0195196 A1 | 10/2003 | Thurston et al. |
| 2003/0206918 A1 | 11/2003 | Fanger et al. |
| 2003/0219806 A1 | 11/2003 | Glucksmann et al. |
| 2003/0224411 A1 | 12/2003 | Stanton et al. |
| 2003/0224454 A1 | 12/2003 | Ryseck et al. |
| 2003/0228319 A1 | 12/2003 | Frantz et al. |
| 2003/0232056 A1 | 12/2003 | Fanger et al. |
| 2003/0232350 A1 | 12/2003 | Afar et al. |
| 2004/0001827 A1 | 1/2004 | Dennis |
| 2004/0005320 A1 | 1/2004 | Thompson et al. |
| 2004/0005538 A1 | 1/2004 | Chen et al. |
| 2004/0005563 A1 | 1/2004 | Mack et al. |
| 2004/0005598 A1 | 1/2004 | Devaux et al. |
| 2004/0018194 A1 | 1/2004 | Francisco et al. |
| 2004/0018553 A1 | 1/2004 | Billing-Medel et al. |
| 2004/0022727 A1 | 2/2004 | Stanton et al. |
| 2004/0044179 A1 | 3/2004 | Baker et al. |
| 2004/0044180 A1 | 3/2004 | Baker et al. |
| 2004/0052793 A1 | 3/2004 | Carter et al. |
| 2004/0101874 A1 | 5/2004 | Ghosh et al. |
| 2004/0101899 A1 | 5/2004 | Dillon et al. |
| 2004/0121940 A1 | 6/2004 | De Groot et al. |
| 2004/0138269 A1 | 7/2004 | Sun et al. |
| 2004/0197325 A1 | 10/2004 | Law et al. |
| 2004/0198722 A1 | 10/2004 | Thurston et al. |
| 2004/0249130 A1 | 12/2004 | Stanton et al. |
| 2005/0271615 A1 | 12/2005 | Shabat et al. |
| 2006/0116422 A1 | 6/2006 | De Groot et al. |
| 2007/0072846 A1 | 3/2007 | Vishnuvajjala et al. |
| 2007/0185336 A1 | 8/2007 | Rossen et al. |
| 2007/0191349 A1 | 8/2007 | Howard et al. |
| 2007/0232592 A1 | 10/2007 | Delavault et al. |
| 2007/0249591 A1 | 10/2007 | Howard et al. |
| 2008/0090812 A1 | 4/2008 | Pepper et al. |
| 2008/0092940 A1 | 4/2008 | Nakajima |
| 2008/0112961 A1 | 5/2008 | Stavenhagen et al. |
| 2008/0206239 A1 | 8/2008 | Jones et al. |
| 2008/0213289 A1 | 9/2008 | Francisco et al. |
| 2008/0214525 A1 | 9/2008 | Howard et al. |
| 2009/0036431 A1 | 2/2009 | Gauzy et al. |
| 2009/0148942 A1 | 6/2009 | McDonagh et al. |
| 2009/0149449 A1 | 6/2009 | Liu et al. |
| 2009/0304710 A1 | 12/2009 | Park et al. |
| 2010/0047257 A1 | 2/2010 | Blanc et al. |
| 2010/0113425 A1 | 5/2010 | Howard et al. |
| 2010/0203007 A1 | 8/2010 | Li et al. |
| 2010/0330095 A1 | 12/2010 | Hettmann et al. |
| 2011/0044984 A1 | 2/2011 | Kitazawa et al. |
| 2011/0070227 A1 | 3/2011 | Novotney-Barry et al. |
| 2011/0160192 A1 | 6/2011 | Howard et al. |
| 2011/0196148 A1 | 8/2011 | Howard et al. |
| 2011/0201803 A1 | 8/2011 | Howard et al. |
| 2011/0256157 A1 | 10/2011 | Howard et al. |
| 2013/0028917 A1 | 1/2013 | Howard et al. |
| 2013/0028919 A1 | 1/2013 | Howard et al. |
| 2013/0243753 A1 | 9/2013 | Pei et al. |
| 2013/0266595 A1 | 10/2013 | Flygare et al. |
| 2014/0066435 A1 | 3/2014 | Howard et al. |
| 2014/0120118 A1 | 5/2014 | Howard |
| 2014/0127239 A1 | 5/2014 | Howard |
| 2014/0234346 A1 | 8/2014 | Howard |
| 2014/0274907 A1 | 9/2014 | Howard et al. |
| 2014/0275522 A1 | 9/2014 | Howard et al. |
| 2014/0294868 A1 | 10/2014 | Howard et al. |
| 2016/0074527 A1 | 7/2016 | Flygare et al. |
| 2016/0304607 A1 | 10/2016 | Sadineni et al. |
| 2017/0107290 A1 | 4/2017 | Micklem et al. |
| 2017/0129957 A1 | 5/2017 | Micklem |
| 2017/0349658 A1 | 12/2017 | Micklem |

FOREIGN PATENT DOCUMENTS

| | | |
|---|---|---|
| EP | 1295944 | 3/2003 |
| EP | 1347046 | 9/2003 |
| EP | 1394274 | 3/2004 |
| EP | 1439393 | 7/2004 |
| EP | 1813614 | 8/2007 |
| EP | 2019104 | 1/2009 |

(56) References Cited

FOREIGN PATENT DOCUMENTS

| | | |
|---|---|---|
| EP | 2228392 A1 | 9/2010 |
| EP | 2267454 A2 | 12/2010 |
| EP | 2298817 | 3/2011 |
| EP | 2431393 A1 | 3/2012 |
| EP | 2589609 A1 | 5/2013 |
| EP | 2528625 | 7/2013 |
| FR | 2027356 | 12/1969 |
| FR | 2586683 | 3/1987 |
| GB | 1299198 | 12/1972 |
| GB | 1410826 | 10/1975 |
| GB | 2053894 | 2/1981 |
| JP | 5382792 | 7/1978 |
| JP | 57131791 | 8/1982 |
| JP | 58180487 | 10/1983 |
| JP | 05003790 | 1/1993 |
| JP | 2004113151 | 4/2004 |
| WO | WO 199102536 | 3/1991 |
| WO | WO 9216221 | 3/1992 |
| WO | WO 199207574 | 5/1992 |
| WO | WO 199217497 | 10/1992 |
| WO | WO 199219620 | 11/1992 |
| WO | WO 199318045 | 9/1993 |
| WO | WO 199410312 | 5/1994 |
| WO | WO 199428931 | 12/1994 |
| WO | WO 199504718 | 2/1995 |
| WO | WO 199630514 | 10/1996 |
| WO | WO 199707198 | 2/1997 |
| WO | WO 199744452 | 11/1997 |
| WO | WO 199813059 | 4/1998 |
| WO | WO 199837193 | 8/1998 |
| WO | WO 199840403 | 9/1998 |
| WO | WO 199851805 | 11/1998 |
| WO | WO 199851824 | 11/1998 |
| WO | WO 199928468 | 6/1999 |
| WO | WO 199946284 | 9/1999 |
| WO | WO 1999049894 | 10/1999 |
| WO | WO 199958658 | 11/1999 |
| WO | WO 200003291 | 1/2000 |
| WO | WO 200012506 | 3/2000 |
| WO | WO 200012507 | 3/2000 |
| WO | WO 200012508 | 3/2000 |
| WO | WO 200012509 | 3/2000 |
| WO | WO 200014228 | 3/2000 |
| WO | WO 200020579 | 4/2000 |
| WO | WO 200022129 | 4/2000 |
| WO | WO 200032752 | 6/2000 |
| WO | WO 200036107 | 6/2000 |
| WO | WO 200040614 | 7/2000 |
| WO | WO 200044899 | 8/2000 |
| WO | WO 200012130 | 9/2000 |
| WO | WO 200053216 | 9/2000 |
| WO | WO 200055351 | 9/2000 |
| WO | WO 2000053216 | 9/2000 |
| WO | WO 200075655 | 12/2000 |
| WO | WO 2000076309 | 12/2000 |
| WO | WO 200100244 | 1/2001 |
| WO | WO 200116104 | 3/2001 |
| WO | WO 200116318 | 3/2001 |
| WO | WO 2001016181 | 3/2001 |
| WO | WO 200138490 | 5/2001 |
| WO | WO 2001032926 | 5/2001 |
| WO | WO 200140269 | 6/2001 |
| WO | WO 200140309 | 6/2001 |
| WO | WO 200141787 | 6/2001 |
| WO | WO 200145746 | 6/2001 |
| WO | WO 200146232 | 6/2001 |
| WO | WO 200146261 | 6/2001 |
| WO | WO 200148204 | 7/2001 |
| WO | WO 200153463 | 7/2001 |
| WO | WO 200157188 | 8/2001 |
| WO | WO 200162794 | 8/2001 |
| WO | WO 200166689 | 9/2001 |
| WO | WO 200172830 | 10/2001 |
| WO | WO 200172962 | 10/2001 |
| WO | WO 200175177 | 10/2001 |
| WO | WO 200177172 | 10/2001 |
| WO | WO 200188133 | 11/2001 |
| WO | WO 200190304 | 11/2001 |
| WO | WO 200194641 | 12/2001 |
| WO | WO 200198351 | 12/2001 |
| WO | WO 200202587 | 1/2002 |
| WO | WO 200202624 | 1/2002 |
| WO | WO 200202634 | 1/2002 |
| WO | WO 200206317 | 1/2002 |
| WO | WO 200206339 | 1/2002 |
| WO | WO 200210187 | 2/2002 |
| WO | WO 200210382 | 2/2002 |
| WO | WO 200212341 | 2/2002 |
| WO | WO 200213847 | 2/2002 |
| WO | WO 200214503 | 2/2002 |
| WO | WO 200216413 | 2/2002 |
| WO | WO 200222153 | 3/2002 |
| WO | WO 200222636 | 3/2002 |
| WO | WO 200222660 | 3/2002 |
| WO | WO 200222808 | 3/2002 |
| WO | WO 200224909 | 3/2002 |
| WO | WO 200226822 | 4/2002 |
| WO | WO 200230268 | 4/2002 |
| WO | WO 200238766 | 5/2002 |
| WO | WO 200254940 | 7/2002 |
| WO | WO 200259377 | 8/2002 |
| WO | WO 200260317 | 8/2002 |
| WO | WO 200261087 | 8/2002 |
| WO | WO 200264798 | 8/2002 |
| WO | WO 200271928 | 9/2002 |
| WO | WO 200272596 | 9/2002 |
| WO | WO 200278524 | 10/2002 |
| WO | WO 200281646 | 10/2002 |
| WO | WO 200283866 | 10/2002 |
| WO | WO 200286443 | 10/2002 |
| WO | WO 200288170 | 11/2002 |
| WO | WO 200288172 | 11/2002 |
| WO | WO 200289747 | 11/2002 |
| WO | WO 200292836 | 11/2002 |
| WO | WO 200294852 | 11/2002 |
| WO | WO 02098897 | 12/2002 |
| WO | WO 200298358 | 12/2002 |
| WO | WO 200299074 | 12/2002 |
| WO | WO 200299122 | 12/2002 |
| WO | WO 2002101075 | 12/2002 |
| WO | WO 2002102235 | 12/2002 |
| WO | WO 200216429 | 1/2003 |
| WO | WO 2003000842 | 1/2003 |
| WO | WO 2003002717 | 1/2003 |
| WO | WO 2003003906 | 1/2003 |
| WO | WO 2003003984 | 1/2003 |
| WO | WO 2003004529 | 1/2003 |
| WO | WO 2003004989 | 1/2003 |
| WO | WO 2003008537 | 1/2003 |
| WO | WO 2003009814 | 2/2003 |
| WO | WO 2003014294 | 2/2003 |
| WO | WO 2003016475 | 2/2003 |
| WO | WO 2003016494 | 2/2003 |
| WO | WO 2003018621 | 3/2003 |
| WO | WO 2003022995 | 3/2003 |
| WO | WO 2003023013 | 3/2003 |
| WO | WO 2003024392 | 3/2003 |
| WO | WO 2003025138 | 3/2003 |
| WO | WO 2003025148 | 3/2003 |
| WO | WO 2003025228 | 3/2003 |
| WO | WO 2003026493 | 4/2003 |
| WO | WO 2003026577 | 4/2003 |
| WO | WO 2003029262 | 4/2003 |
| WO | WO 2003029277 | 4/2003 |
| WO | WO 2003029421 | 4/2003 |
| WO | WO 2003034984 | 5/2003 |
| WO | WO 2003035846 | 5/2003 |
| WO | WO 2003042661 | 5/2003 |
| WO | WO 2003043583 | 5/2003 |
| WO | WO 2003045422 | 6/2003 |
| WO | WO 2003048202 | 6/2003 |
| WO | WO 2003054152 | 7/2003 |
| WO | WO 2003055439 | 7/2003 |
| WO | WO 2003055443 | 7/2003 |

(56) References Cited

FOREIGN PATENT DOCUMENTS

| | | |
|---|---|---|
| WO | WO 2003060612 | 7/2003 |
| WO | WO 2003062401 | 7/2003 |
| WO | WO 2003068983 | 8/2003 |
| WO | WO 2003072035 | 9/2003 |
| WO | WO 2003072036 | 9/2003 |
| WO | WO 2003077836 | 9/2003 |
| WO | WO 2003081210 | 10/2003 |
| WO | WO 2003083041 | 10/2003 |
| WO | WO 2003083047 | 10/2003 |
| WO | WO 2003083074 | 10/2003 |
| WO | WO 2003087306 | 10/2003 |
| WO | WO 2003087768 | 10/2003 |
| WO | WO 2003088808 | 10/2003 |
| WO | WO 2003089624 | 10/2003 |
| WO | WO 2003089904 | 10/2003 |
| WO | WO 2003093444 | 11/2003 |
| WO | WO 2003097803 | 11/2003 |
| WO | WO 2003101283 | 12/2003 |
| WO | WO 2003101400 | 12/2003 |
| WO | WO 2003104270 | 12/2003 |
| WO | WO 2003104275 | 12/2003 |
| WO | WO 2003104399 | 12/2003 |
| WO | WO 2003105758 | 12/2003 |
| WO | WO 2004000221 | 12/2003 |
| WO | WO 2004000997 | 12/2003 |
| WO | WO 2004001004 | 12/2003 |
| WO | WO 2004005598 | 1/2004 |
| WO | WO 2004009622 | 1/2004 |
| WO | WO 2004011611 | 2/2004 |
| WO | WO 2004015426 | 2/2004 |
| WO | WO 2004016225 | 2/2004 |
| WO | WO 2004020583 | 3/2004 |
| WO | WO 2004020595 | 3/2004 |
| WO | WO 2004022709 | 3/2004 |
| WO | WO 2004022778 | 3/2004 |
| WO | WO 2004027049 | 4/2004 |
| WO | WO 2004031238 | 4/2004 |
| WO | WO 2004032828 | 4/2004 |
| WO | WO 2004032842 | 4/2004 |
| WO | WO 2004040000 | 5/2004 |
| WO | WO 2004042346 | 5/2004 |
| WO | WO 2004043361 | 5/2004 |
| WO | WO 2004043963 | 5/2004 |
| WO | WO 2004044178 | 5/2004 |
| WO | WO 2004045516 | 6/2004 |
| WO | WO 2004045520 | 6/2004 |
| WO | WO 2004045553 | 6/2004 |
| WO | WO 2004046342 | 6/2004 |
| WO | WO 2004047749 | 6/2004 |
| WO | WO 2004048938 | 6/2004 |
| WO | WO 2004053079 | 6/2004 |
| WO | WO 2004058309 | 7/2004 |
| WO | WO 2004063355 | 7/2004 |
| WO | WO 2004063362 | 7/2004 |
| WO | WO 2004063709 | 7/2004 |
| WO | WO 2004065576 | 8/2004 |
| WO | WO 2004065577 | 8/2004 |
| WO | WO 2004074320 | 9/2004 |
| WO | WO 2005023814 | 3/2005 |
| WO | WO 2005040170 | 5/2005 |
| WO | WO 2005042535 | 5/2005 |
| WO | WO 2005079479 | 9/2005 |
| WO | WO 2005082023 | 9/2005 |
| WO | WO 2005085177 | 9/2005 |
| WO | WO 2005085250 | 9/2005 |
| WO | WO 2005085251 | 9/2005 |
| WO | WO 2005085259 | 9/2005 |
| WO | WO 2005085260 | 9/2005 |
| WO | WO 2005105113 | 11/2005 |
| WO | WO 2005110423 | 11/2005 |
| WO | WO 2006065533 | 6/2006 |
| WO | WO 2006105021 | 10/2006 |
| WO | WO 2006111759 | 10/2006 |
| WO | WO 2007005874 | 1/2007 |
| WO | WO 2007039752 | 4/2007 |
| WO | WO 2007044515 | 4/2007 |
| WO | WO 2007085930 | 8/2007 |
| WO | WO 2008010101 | 1/2008 |
| WO | WO 2008047242 | 4/2008 |
| WO | WO 2008070593 | 6/2008 |
| WO | WO 2009009116 | 1/2009 |
| WO | WO 2009062690 A1 | 1/2009 |
| WO | WO 2009016516 | 2/2009 |
| WO | WO 2009052249 | 4/2009 |
| WO | WO 2009062690 A1 | 5/2009 |
| WO | WO 2009117531 | 9/2009 |
| WO | WO 2010010347 | 1/2010 |
| WO | WO 2010043877 | 4/2010 |
| WO | WO 2010043880 | 4/2010 |
| WO | WO 2010091150 | 8/2010 |
| WO | WO 2010130751 A1 | 11/2010 |
| WO | WO 2011005481 | 1/2011 |
| WO | WO 2011014457 A1 | 2/2011 |
| WO | WO 2011023883 | 3/2011 |
| WO | WO 2011028683 | 3/2011 |
| WO | WO 2011028811 | 3/2011 |
| WO | WO 2011038159 | 3/2011 |
| WO | WO 2011100227 | 8/2011 |
| WO | WO 2011130598 | 10/2011 |
| WO | WO 2011130613 | 10/2011 |
| WO | WO 2011130615 | 10/2011 |
| WO | WO 2011130616 | 10/2011 |
| WO | WO 2011159980 A1 | 12/2011 |
| WO | WO 2011161699 | 12/2011 |
| WO | WO 2012064733 A2 | 5/2012 |
| WO | WO 2012112687 | 8/2012 |
| WO | WO 2012112708 | 8/2012 |
| WO | WO 2012128868 | 9/2012 |
| WO | WO 2012145493 | 10/2012 |
| WO | WO 2012175691 A1 | 12/2012 |
| WO | WO 2012175692 A1 | 12/2012 |
| WO | WO 2013041606 | 3/2013 |
| WO | WO 2013053871 | 4/2013 |
| WO | WO 2013053873 | 4/2013 |
| WO | WO 2013055987 | 4/2013 |
| WO | WO 2013055990 | 4/2013 |
| WO | WO 2013055993 | 4/2013 |
| WO | WO 2013093809 | 6/2013 |
| WO | WO 2013177481 | 11/2013 |
| WO | WO 2014011518 | 1/2014 |
| WO | WO 2014022679 | 2/2014 |
| WO | WO 2014055648 | 4/2014 |
| WO | WO 2014057072 | 4/2014 |
| WO | WO 2014057073 | 4/2014 |
| WO | WO 2014057074 | 4/2014 |
| WO | WO 2014057113 | 4/2014 |
| WO | WO 2014057114 | 4/2014 |
| WO | WO 2014057115 | 4/2014 |
| WO | WO 2014057117 | 4/2014 |
| WO | WO 2014057118 | 4/2014 |
| WO | WO 2014057119 | 4/2014 |
| WO | WO 2014057120 | 4/2014 |
| WO | WO 2014057122 | 4/2014 |
| WO | WO 2014174111 A1 | 10/2014 |
| WO | WO 2015031693 A1 | 3/2015 |
| WO | WO 2015031698 | 3/2015 |
| WO | WO 2015095423 | 6/2015 |
| WO | WO 2015153514 | 8/2015 |
| WO | WO 2016000619 | 1/2016 |
| WO | WO 2016007235 | 1/2016 |
| WO | WO 2016011160 | 1/2016 |
| WO | WO 2016053107 | 4/2016 |
| WO | WO 2016057667 | 4/2016 |
| WO | WO 2016073380 | 5/2016 |
| WO | WO 2016081384 | 5/2016 |
| WO | WO 2016127052 | 8/2016 |
| WO | WO 2016166297 | 10/2016 |
| WO | WO 2016166302 | 10/2016 |
| WO | WO 2016179517 | 11/2016 |
| WO | WO 2016189124 | 12/2016 |
| WO | WO 2016196792 | 12/2016 |
| WO | WO 2017004016 | 1/2017 |

(56) References Cited

FOREIGN PATENT DOCUMENTS

| WO | WO 2017130076 | 8/2017 |
|----|---------------|--------|
| WO | WO 2018146189 | 8/2018 |
| WO | WO 2015042246 | 3/2019 |

OTHER PUBLICATIONS

Chothia; et al., "Domain association in immunoglobulin molecules. The packing of variable domains." J Mol. Biol. 1985, 186(3), 651.

Cree et al., "Methotrexate chemosensitivity by ATP luminescence in human leukemia cell lines and in breast cancer primary cultures: comparison of the TCA-100 assay with a clonogenic assay," (1995) AntiCancer Drugs 6:398-404.

Crouch et al., "The use of ATP bioluminescence as a measure of cell proliferation and cytotoxicity," (1993) J. Immunol. Meth. 160:81-88.

Gjerdrum, et al., "Axl is an essential epithelial-to-mesenchymal transition-induced regulator of breast cancer metastasis and patient survival." Proc Natl Acad Sci U S A. Jan. 19, 2010; 107(3):1124-9.

Handbook of Pharmaceutical Additives, 2nd Edition (eds. M. Ash and I. Ash), 2001 (Synapse Information Resources, Inc., Endicott, New York, USA).

Handbook of Pharmaceutical Excipients, 2nd edition, 1994.

Holland; et al., "R428, a selective small molecule inhibitor of Axl kinase, blocks tumor spread and prolongs survival in models of metastatic breast cancer." Cancer Res 2010, 70: 1544.

International Preliminary Report on Patentability and Written Opinion issued in PCT/EP2015/063700, dated Dec. 20, 2016; 8 pages.

International Preliminary Report on Patentability and Written Opinion issued in PCT/EP2015/063704, dated Dec. 20, 2016; 8 pages.

International Search Report and Written Opinion issued in PCT Application No. PCT/EP2015/063700, dated Dec. 8, 2015, 12 pages.

International Search Report and Written Opinion issued in PCT Application No. PCT/EP2015/063704, dated Oct. 8, 2015, 11 pages.

International Search Report and Written Opinion issued in PCT Application No. PCT/EP2016/058368, dated Oct. 10, 2016, 30 pages.

Ishikawa; et al. "Higher expression of receptor tyrosine kinase Axl, and differential expression of its ligand, Gas6, predict poor survival in lung adenocarcinoma patients." Ann Surg Oncol. Dec. 2013; 20 Suppl 3:S467-76.

J. Foote and G. Winter, "Antibody framework residues affecting the conformation of the hypervariable loops," J Mol. Biol. 1992, 224(2): 487-499.

Korshunov, "Axl-dependent signalling: a clinical update." Clin Sci (Lond). Apr. 2012; 122(8):361-8.

Leconet; et al., "Preclinical validation of Axl receptor as a target for antibody-based pancreatic cancer immunotherapy." Oncogene. Nov. 20, 2014;33(47):5405-14.

Li, et al., "Axl-Targeted Cancer Imaging with Humanized Antibody h173", Molecular Imaging and Biology, Jan. 15, 2014, 16(4): 511-518.

Linger, et al., "Taking aim at Mer and Axl receptor tyrosine kinases as novel therapeutic targets in solid tumors." Expert Opin Ther Targets. Oct. 2010; 14(10):1073-90.

Linger, et al., "TAM receptor tyrosine kinases: biologic functions, signaling, and potential therapeutic targeting in human cancer." Adv Cancer Res. 2008; 100:35-83.

Liu & May, "Disulfide bond structures of IgG molecules Structural variations, chemical modifications and possible impacts to stability and biological function." Jan./Feb. 2012; Landes Bioscience, pp. 17-23.

Loges; et al., "Malignant cells fuel tumor growth by educating infiltrating leukocytes to produce the mitogen Gas6." Blood. Mar. 18, 2010;115(11):2264-73.

McDonagh; et al., "Engineered antibody—drug conjugates with defined sites and stoichiometries of drug attachment." Protein Engineering, Design & Selection 2006, 19(7): 299-307.

Meyer, et al., "The receptor Axl diversifies EGFR signaling and limits the response to EGFR-targeted inhibitors in triple-negative breast cancer cells." Sci Signal. Aug. 6, 2013; 6(287):ra66.

Nicolaoua; et al., "Calicheamicin θ: A Rationally Designed Molecule with Extremely Potent and Selective DNA Cleaving Properties and Apoptosis Inducing Activity." Angewandte Chemie International Edition in English 1994, 33: 183-186.

Paccez; et al., "The receptor tyrosine kinase Axl is an essential regulator of prostate cancer proliferation and tumor growth and represents a new therapeutic target." Oncogene. Feb. 7, 2013; 32(6):689-98.

Rudikoff; et al., "Somatic diversification of immunoglobulins." Proc Natl Acad Sci U S A. Apr. 1984; 81(7):2162-6.

Song, et al., "Overexpression of receptor tyrosine kinase Axl promotes tumor cell invasion and survival in pancreatic ductal adenocarcinoma." Cancer. Feb. 15, 2011; 117(4):734-43.

Ye, et al., "An anti-Axl monoclonal antibody attenuates xenograft tumor growth and enhances the effect of multiple anticancer therapies." Oncogene, Nature Publishing Group, Sep. 1, 2010, 29(38): 5254-5264.

Yuen; et al., "Taz expression as a prognostic indicator in colorectal cancer." PLoS One. 2013;8(1):e54211.

Zhang; et al., "Activation of the Axl kinase causes resistance to Egfr-targeted therapy in lung cancer."Nat Genet. Jul. 1, 2012;44(8):852-60.

3-Aminobenzamide, NCBI Pubchem reference 1645.

Adair, J.R. et al., "Antibody-drug conjugates—a perfect synergy," Exp. Opin. Biol. Ther. (2012), pp. 1-16.

Adams et al., "Molecular modelling of a sequence-specific DNA-binding agent based on the pyrrolo[2,1-c][1,4]benzodiazepines," Pharm. Pharmacol. Commun. (1999) 5:555-560.

Aird, R.E. et al., "ABCB1 genetic polymorphism influences the pharmacology of the new pyrrolobenzodiazepine derivative SJG-136," Pharmacogenomics Journal (2008) 8(4):289-296.

Alley, M.C. et al., ""SJG-136 (NSC 694501), a novel rationally designed DNA minor groove interstrand cross-linking agent with potent and broad spectrum antitumor activity. Part 2: Efficacy evaluations,"" Cancer Res. (2004) 64:6700-6706.

Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.

Alley, S. C., "Contribution of Linker Stability to the Activities of Anticancer Immunoconjugates" Bioconjugate Chem 2008, 19, 759-765.

Althius, T. H. and Hess, H. J., "Synthesis and Identification of the Major Metabolites of Prazosin Formed in Dog and Rat," J. Medicinal Chem. (1977) 20(1):146-148.

Altuvia et al., "Ranking potential binding peptides to MHC molecules by a computational threading approach." J. Mol. Biol., 249, 244-250 (1995).

Amiel J., et al., "Heterozygous endothelin receptor B {EDNRB) mutations in isolated Hirschsprung disease," Hum. Mol. Genet. 5, 355-357, 1996.

Amir et al., "Self-Immolative Dendrimers," (2003) Angew. Chem. Int. Ed. 42:4494-4499.

Amsberry, et al, "The Lactonization of 2'-Hydroxyhydrocinnamic Acid Amides: A Potential Prodrug for Amines," (1990) J. Org. Chem. 55:5867-5877.

Anti-GITR Agonistic Monoclonal Antibody BMS-986156, NCI Thesaurus, Code C132267.

Anti-GITR Monoclonal Antibody GWN 323, NCI Thesaurus Code C128028.

Anti-GITR Monoclonal Antibody MK-4166, NCI Thesauruse Code C116065.

Anti-human GITR Monoclonal Antibody TRX518, NCI thesaurus code C95023.

Anti-OX40 Agonist Monoclonal Antibody PF-04518600, NCI thesaurus code C121927.

Antonow, D. et al., ""Synthesis of DNA-Interactive Pyrrolo [2,1-c][1,4] benzodiazepines (PBDs)"" Chemical Reviews, 2011, 111(4):2815-2864.

(56) References Cited

OTHER PUBLICATIONS

Antonow, D. et al., "Structure-activity relationships of monomeric C2-aryl pyrrolo[2,1-c][1,4]benzodiazepine (PBD) antitumor agents." J Med Chem. Apr. 8, 2010;53(7):2927-41.
Antonow, D. et al.,"Parallel synthesis of a novel C2-aryl pyrrolo[2,1-c][1,4]benzodiazepine (PBD) library," J. Comb. Chem. (2007) 9:437-445.
Arai H., et al., ""Molecular cloning of human endothelin receptors and their expressiOn in vascular endothelial cells and smooth muscle cells,"" Jpn. Circ. J. 56, 1303-1307, 1992.
Arai H., et al., "The Human Endotbelin-B Receptor Gene. Structural Organization and Chromosomal Assignment," J. Biol. Chem. 268, 3463-3470, 1993.
Arima et al., "Studies on Tomaymycin, a New Antibiotic. I. Isolation and Properties of Tomaymycin," J. Antibiotics (1972) 25:437-444.
Arnould, S., ""Impact on the cell cycle and involvement of ATM, ATR, chk1 and chk2 kinases in the cytotoxicity of SJG-136, a new pyrrolobenzodiazepine dimer,"" Proceedings of the American Association for Cancer Research Annual Meeting (Mar. 2004) 45:1298, Abstract No. 5618.
Arnould, S., "Time-dependent cytotoxicity induced by SJG-136 (NSC 694501): influence of the rate of interstrand cross-link formation on DNA damage signaling," Mol. Canc. Therap. 5(6):1602-1609 (2006).
Atezolizumab, Drug Bank Accession No. DB11595.
Attie T., et al., "Mutation of the endothelin-receptor B gene in Waardenburg-Hirschsprung disease," Hum. Mol. Genet. 4, 2407-2409, 1995.
Auricchio A., et al., "Endothelin-B receptor mutations in patients with isolated Hirschsprung disease from a non-inbred population," Hum. Mol. Genet. 5:351-354, 1996.
Axup et al., "Synthesis of site-specific antibody-drug conjugates using unnatural amino acids." Proc Natl Acad Sci U S A. Oct. 2, 2012; 109(40)1 6101-6.
Azacitidine, NCBI Pubchem reference 9444.
Babb et al. "Cancer phase I clinical trials: efficient dose escalation with overdose control." Stat Med. May 30, 1998; 17(10):1103-20.
Bahrenberg et al., ""Reduced Expression of PSCA, a Member of the LY-6 Family of Cell Surface Antigens, in Bladder, Esophagus, and Stomach Tumors,"" Biochem. Biophys. Res. Commun. (2000) 275(3):783-788.
Banker, G.S. et al., "Modern Pharmaceutics", Third edition, Marcel Dekker, New York (1996) 451 and 596.
Barel M., et al., "Evidence fora new transcript of the Epstein-Barr virus/C3d receptor (CR2, CD21) which is due to alternative exon usage," Mol. Immunol. 35, 1025-1031, 1998.
Barella et al., "Sequence variation of a novel heptahelical leucocyte receptor through alternative transcript formation," (1995) Biochem. J. 309:773-779.
Barnett T., et al., "Carcinoembryonic Antigen Family: Characterization of cDNAs Coding for NCA and CEA and Suggestion of Nonrandom Sequence Variation in Their Conserved Loop-Domains," Genomics 3, 59-66, 1988.
Batisse, et al., "A new delivery system for Auristatin in STxB-drug conjugate therapy." European J. Medicinal Chemistry, 2015, 95: 483-491.
Beck et al., "DNA Sequence Analysis of 66 kb of the Human MHC Class II Region Encoding a Cluster of Genes for Antigen Processing," (1992) J. Mol. Biol. 228:433-441.
Beck et al., "Evolutionary Dynamics of Non-coding Sequences Within the Class II Region of the Human MHC," (1996) J. Mol. Biol. 25 255:1-13.
Berge et al., "Pharmaceutical Salts," J. Pharm. Sci. (1977) 66:1-19.
Berry, J. M. et al., "Solid-phase synthesis of DNA-interactive pyrrolo[2,1-c][1,4]benzodiazepines," Tetrahedron Letters (2000) 41:6171-6174.
Blanc et al., "SAR3419: an anti-CD19-Maytansinoid Immunoconjugate for the treatment of B-cell malignancies," Clin Cancer Res., 2011, 17(20):6448-58.

Bloom et al., "Intrachain disulfide bond in the core hinge region of human IgG4." Protein Sci. Feb. 1997; 6(2):407-15.
Blumberg H., et al., ""Interleukin 20: Discovery, Receptor Identification, and Role in Epidermal Function,"" Cell 104, 9-19, 2001.
Borch et al., "Reorienting the immune system in the treatment of cancer by using anti-Pd-1 and anti-Pd-L1 antibodies." Drug Discov Today. Sep. 2015; 20(9):1127-34.
Bose et al., "New Approaches to Pyrrolo[2,1-c][1,4]benzodiazepines: Synthesis, DNA-binding and cytotoxicity of DC-81," Tetrahedron, 48, 751-758 (1992).
Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20: 1518-1520.
Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).
Bourgeois C., et al., "Endothelin-1 and ETA Receptor Expression in Vascular Smooth Muscle Cells from Human Placenta: A New ETA Receptor Messenger Ribonucleic Acid Is Generated by Alternative Splicing of Exon 3," J. Clin. Endocrinol. Metab. 82, 3116-3123, 1997.
Brand et al., Prospect for anti-HER2 receptor therapy in breast cancer. Anticancer. Res. Jan.-Feb. 2006;26(16):463-70.
Brinster et al., ""Introits increase transcriptional efficiency in transgenic mice,"". (1988) Proc. Natl. Acad. Sci. USA 85:836-840.
Buchman et al., "Comparison of Intron-Dependent and Intron-Independent Gene Expression," (1988) Mol. Cell. Biol. 8:4395-4405.
Buhrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.
Burke, P.J. et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.
Burke, P.J. et al., "Novel immunoconjugates comprised of streptonigrin and 17-amino-geldanamycin attached via a dipeptide-p-aminobenzylamine linker system," Bioorg. Med. Chem. Lett., Apr. 2009, 19(10):2650-2653.
Burton, "Immunoglobulin G: functional sites." Mol Immunol. Mar. 1985; 22(3):161-206.
Calcutt, M.W., "Determination of chemically reduced pyrrolobenzodiazepine SJG-136 in human plasma by HPLC-MS/MS: application to an anticancer phase I dose escalation study," J. Mass Spectrom. (2008) 43(1):42-52.
Camrelizumab, NCI Thesaurus code C123816.
Capellas et al., "Enzymatic condensation of cholecystokinin CCK-8 (4-6) and CCK-8 (7-8) peptide fragments in organic media." Biotechnol Bioeng. Nov. 20, 1997; 56(4):456-63.
Carl et al., "A Novel Connector Linkage Applicable in Prodrug Design," (1981) J. Med. Chem. 24:479-480.
Carlsson et al., "Protein Thiolation and Reversible Protein-Protein Conjugation," (1978) Biochem. J. 173:723-737.
Carter, P., "Potent antibody therapeutics by design," (2006) Nature Reviews Immunology 6:343-357.
Casset et al., "A peptide mimetic of an anti-CD4 monoclonal antibody by rational design." Biochem Biophys Res Commun. Jul. 18, 2003; 307(1):198-205.
CellTiter-Glo Luminescent Cell Viability Assay, Promega Corp. Technical Bulletin TB288, dated Jan. 13, 2012 (14 pages).
Cemiplimab, NCI thesaurus code C121540.
Chakravarty et al., ""Plasmin-Activated Prodrugs for Cancer Chemotherapy. 2. Synthesis and Biological Activity of Peptidyl Derivatives of Doxorubicin,"" (1983) J. Med. Chern. 26:638-644.
Chan, J. and Watt, V.M., "eek and erk, new members of the eph subclass of receptor protein-tyrosine kinases," Oncogene 6 (6), 1057-1061 (1991).
Chang et al., "Molecular cloning of mesothelin, a differentiation antigen present on mesothelium, mesotheliomas, and ovarian cancers," Proc. Natl. Acad. Sci. U.S.A. 93 (1):136-140 (1996).

(56) References Cited

OTHER PUBLICATIONS

Chen, Z. et al., A novel approach to the synthesis of cytotoxic C2-C3 unsaturated pyrrolo[2,1-c][1,4]benzodiazepines (PBDs) with conjugated acrylyl C2-substituents, Biorg. Med. Chem. Lett. (2004) 14:1547-1549.

Cheung, A., "Direct liquid chromatography determination of the reactive imine SJG-136 (NSC 694501)," J. Chromat. B: Anal. Techn. Biomed. Life Sci. (2005) 822(1-2):1020.

Child et al., "Translational Control by an Upstream Open Reading Frame in the HER-2/neu Transcript," (1999) J. Bioi. Chern. 274:24335-24341.

Cho et al., ""Structure of the extracellular region of HER2 alone and in complex with the Herceptin Fab,"" Nature 421, 756-760, 2003.

Ciccodicola, A., et al., ""Molecular characterization of a gene of the 'EGF family' expressed in undifferentiated human NTERA2 teratocarcinoma cells,"" EMBO J. 8 (7):1987-1991 (1989).

Cipolla, L., "Pyrrolo[2,1-c][1,4]benzodiazepine as a scaffold for the design and synthesis of anti-tumour drugs," Anti-Cancer Agents in Medicinal Chemistry (Jan. 2009) 9(1):1-31.

Clackson et al., "Making antibody fragments using phage display libraries," (1991) Nature, 352:624-628.

Clark H.F., et al., "The Secreted Protein Discovery Initiative (SPDI], a Large-Scale Effort to Identify Novel Human Secreted and Transmembrane Proteins: A Bioinformatics Assessment," Genome Res. 13, 2265-2270, 2003.

Clingen, P.H., "The role of nucleotide excision repair and homologous recomination in the sensitivity of mammalian cells to the minor groove crosslinking pyrrolo[2,1-c][1,4]benzodiazepine dimer SJG-136 (NSC694501)," Proceedings of the American Association for Cancer Research Annual Meeting (Jul. 2003) 44:524.

Clingen, P.H., "The XPF-ERCC1 endonuclease and homologous recombination contribute to the repair of minor groove DNA interstrand crosslinks in mammalian cells produced by the pyrrolo[2,1-c][1,4]benzodiazepine dimer SJG-136," Nucl. Acids Res. (2005) 33(10):3283-3291.

Clinical Trial, "Translational research: 4 ways to fix the clinical trial." 2011, http://www.nature.com/news/2011/110928/full/477526a.html.

Clinical Trials Identifier: NCT01239134, "ITrial of TRX518 (Anti-GITR mAb) in Stage III or IV Malignant Melanoma or Other Solid Tumors (TRX518-001)," Actual Study Completion Date: Sep. 2018; Leap Therapeutics, Inc.

Clinical Trials Identifier: NCT02013804; Study Completion Date: May 18, 2017, "A Phase 1 Multicenter Open-label Study to Evaluate the Safety Tolerability and PK of MED10680 (AMP-514) in Subjects with Advanced Malignancies", Medimmune LLC.

Clinical Trials Identifier: NCT02028403, "Safety and Immune Response of BMS-936559 in Hiv-Infected People Taking Combination Antiretroviral Therapy" Study Start Date: Jun. 2014; Completion Date: Nov. 2015; National Cancer Institute (NCI).

Clinical Trials Identifier: NCT02132754, "Study of MK-4166 and MK-4166 in Combination with Pembrolizumab (MK-3475) in Participants With Advanced Solid Tumors (MK-4166-001)" Study Start Date: Jun. 27, 2014; Estimated Completion Date: Oct. 17, 2019; Merck Sharp & Dohme Corp.

Clinical Trials Identifier: NCT02221960, "A Phase 1 Study to Evaluate MEDI6383 Alone and in Combination with MEDI4736 in Adult Subjects With Select Advanced Solid Tumors." Study Start Date: Sep. 15, 2014; Completion Date: Jul. 3, 2017; MedImmune LLC.

Clinical Trials Identifier: NCT02271945; Study Completion Date: May 24, 2016, "Safety/Efficacy of MEDI-551 in Combination With Immunomodulating Therapies in Subjects With Aggressive B-cell Lymphomas", Medimmune LLC.

Clinical Trials Identifier: NCT02298946, "AMP-224, a PD-1 Inhibitor, With Stereotactic Body Radiation Therapy in Metastatic Colorectal Cancer" Study Start Date: Nov. 21, 2014; Completion Date: Mar. 7, 2017; National Cancer Institute (NCI).

Clinical Trials Identifier: NCT02315066, "Study of OX40 Agonist PF-04518600 Alone and in Combination With 4-1BB Agonist PF-05082566." Study Start Date: Apr. 23, 2015; Estimated Completion Date: Apr. 30, 2020; Pfizer.

Clinical Trials Identifier: NCT02318394, "AA Phase 1 Study of MEDI0562 in Adult Subjects with Selected Advanced Solid Tumors." Study Start Date: Mar. 2, 2015; Completion Date: Jan. 9, 2018; MedImmune LLC.

Clinical Trials Identifier: NCT02528357, "GSK3174998 Alone or With Pembrolizumab in Subjects with Advanced Solid Tumors (ENGAGE-1)." Study Start Date: Sep. 11, 2015; Estimated Completion Date: Apr. 8, 2021; GlaxoSmithKline.

Clinical Trials Identifier: NCT02553499, "Study of MK-1248 With and Without Pembrolizumab (MK-3475) for Participants With Advanced Solid Tumors (MK-1248001)," Study Start Date: Nov. 12, 2015; Completion Date: Oct. 17, 2018; Merck Sharp & Dohme Corp.

Clinical Trials Identifier: NCT02583165, "A Study in Adult Subjects With Select Advanced Solid Tumors," Study Completion Date: Dec. 19, 2018; MedImmune LLC.

Clinical Trials Identifier: NCT02598960, "An Investigational Immunotherapy Study of Experimental Medication BMS-986156, Given by Itself or in Combination With Nivolumab in Patients With Solid Cancers or Cancers That Have Spread." Study Start Date: Oct. 9, 2015; Estimated Completion Date: Jan. 31, 2020; Bristol-Myers Squibb.

Clinical Trials Identifier: NCT02628574, "Phase 1 Open-label Study of TRX518 Monotherapy and TRX518 in Combination With Gemcitabine, Pembrolizumab, or Nivolumab," Study Start Date: Jan. 2016; Leap Therapeutics, Inc.

Clinical Trials Identifier: NCT02923349, "A Phase 1/2, Open-Label, Dose-Escalation, Safety Study of INCAGN01949 in Subjects With Advanced or Metastatic Solid Tumors." Study Start Date: Oct. 2016; Completion Date: Mar. 26, 2019; Incyte Biosciences International Sàrl.

Clinical Trials Identifier: NCT03277352, "INCAGN01876 in Combination With Immune Therapies in Subjects With Advanced or Metastatic Malignancies," Estimated Study Completion Date: May 2020; Incyte Biosciences International Sàrl.

Collins, "Generation and initial analysis of more than 15,000 full-length human and mouse eDNA sequences," Proc. Natl. Acad. Sci. U.S.A. 99 (26):16899-16903 (2002).

Cooper, N. et al., "Synthesis of novel PBDs as anti-tumour agents," Chem. Commun. (2002) 16:1764-1765.

Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.

Corey et al., "LuCap35: a new model of prostate cancer progression to androgen independence." The Prostate 2003;55:239-46.

Courtney, S. M. et al., "A new convenient procedure for the synthesis of pyrrolo[2,1-c][1,4]benzodiazepines", Tetrahedron Letters, vol. 34, No. 33, 5327-28 (1993).

Coussens et al., "Tyrosine Kinase Receptor with Extensive Homology to EGF Receptor Shares Chromosomal Location With neu Oncogene," Science (1985) 230(4730):1132-1139.

Cragg et al., "The alternative transcript of CD79b is overexpressed in B-CLL and inhibits signaling for apoptosis," Blood (2002) 100 (9):3068-3076.

Cytarabine; NCBI Pubchem reference 6253.

Dall'Acqua, W. F. et al., "Antibody humanization by framework shuffling" Methods, 36, 43-60 (2005).

Dattolo, G. et al., "Polycondensed nitrogen heterocycles. IX. 5,6-dihydro-7H-pyrrolo[1,2-d][1,4]benzodiazepin-6-one," J. Heterocyclic. Chem. (1980) 17:701-703.

Davis et al., "Identification of a family of Fe receptor homo logs with preferential B cell expression," (2001) Proc. Natl. Acad. Sci. USA 98(17):9772-9777.

De Groot et al., ""Cascade-Release Dendrimers"" Liberate All End Groups upon a Single Triggering Event in the Dendritic Core, (2003) Angew. Chern. Int. Ed. 42:4490-4494.

(56) References Cited

OTHER PUBLICATIONS

De Groot et al., "Elongated Multiple Electronic Cascade and Cyclization Spacer Systems in Activatible Anticancer Prodrug for Enhanced Drug Release," (2001) J. Org. Chern. 66:8815-8830.
De Pascalis et al., "Grafting of "abbreviated" complementarity-determining regions containing specificity-determining residues essential for ligand contact to engineer a less immunogenic humanized monoclonal antibody." J Immunol. Sep. 15, 2002;169(6):3076-84.
Decitabine, NCBI Pubchem reference 451668.
Dennis et al., (2002) "Albumin Binding As a General Strategy for Improving the Pharmacokinetics of Proteins" J Biol Chem. 277:35035-35043.
Dijke, P., et al., "Characterization of Type I Receptors for Transforming Growth Factor-beta and Activin," Science 264 (5155):101-104 (1994).
Dobner et al., "Differentiation-specific expression of a novel G protein-coupled receptor from Burkitt's lymphoma," (1992) Eur. J. Immunol. 22:2795-2799.
Dong, Q. et al., "Reductive cleavage of TROC groups under neutral conditions with cadmium-lead couple," Tetrahedron Lett. (1995) 36(32):5681-5682.
Dono et al., "Isolation and Characterization of the CRI PTO Autosomal Gene and Its X-linked Related Sequence," Am. J. Hum. Genet. 49:555-565, 1991.
Dornan et al., "Therapeutic potential of an anti-CD79b antibody-drug conjugate, anti-CD79b-vc-MMAE, for the treatment of non-Hodgkin lymphoma," (2009) Blood 114(13):2721-2729.
Doronina et al., "Enhanced Activity of Monomethylauristatin F through Monoclonal Antibody Delivery: Effects of Linker Technology on Efficacy and Toxicity," (2006) Bioconj. Chem. 17:114-124.
Doronina, S.O. et al., "Development of potent monoclonal antibody auristatin conjugates for cancer therapy," Nature Biotech. (2003) 21:778-784.
Dorwald, F.Z., Side Reactions in Organic Synthesis: a Guide to Successful Synthesis Design, Weinheim: Wiley-VCH Verlag GmbH & Co., KGaA (2005) Preface.
Doyle, M., "Response of *Staphylococcus aureus* to subinhibitory concentrations of a sequence-selective, DNA minor groove cross-linking pyrrolobenzodiazepine dimer," J. Antimicrob. Chemo., Aug. 2009, 64(5):949-959.
Dubowchik et al, "Cathepsin B-sensitive dipeptide prodrugs. 1. A model study of structural requirements for efficient release of doxorubicin." Bioorg Med Chem Lett. Dec. 1, 1998; 8(23):3341-6.
Dubowchik et al, "Cathepsin B-sensitive dipeptide prodrugs. 2. Models of anticancer drugs paclitaxel (Taxol), mitomycin C and doxorubicin." Bioorganic & Medicinal Chemistry Letters, 8:3347-3352, (1998).
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem. (2002) 13, 855-869.
Dubowchik, et al., "Monomethoxytrityl (MMT) as a Versatile Amino Protecting Group for Complex Prodrugs of Anticancer Compounds Sensitive to Strong Acids, Bases and Nucleophiles," (1997) Tetrahedron Letters. 38:5257-5260.
Dumoutier L., et al., "Cutting Edge: STAT Activation by IL-19, IL-20 and mda-7 Through IL-20 Receptor Complexes of Two Types," J. Immunol. 167, 3545-3549, 2001.
Dupont, C. et al., "Synthesis of rhazinilam analogue acting as an inhibitor of tubulin assembly," Tetrahedron Lett. (2000) 41:5853-5856.
Efizonerimod, NCI Thesaurus, Code C118282.
Ehsani A., et al., "Characterization of a New Allele of the Human ERBB2 Gene by Allele-Specific Competition Hybridization," (1993) Genomics 15, 426-429.
Elshourbagy N.A., et al., "Molecular Characterization and Regulation of the Human Endothelin Receptors," J. Biol. Chem. 268, 3873-3879, 1993.
Erickson et al., "Antibody-Maytansinoid Conjugates Are Activated in Targeted Cancer Cells by Lysosomal Degradation and Linker-Dependent Intracellular Processing," (2006) Cancer Res. 66(8): 4426-4433.
Farmer, J.D. et al., "Synthesis and DNA crosslinking ability of a dimeric anthramycin analog," Tetrahedron Letters (1988) 29(40):5105-5108, Abstract only.
Farmer, J.D. et al., "DNA binding properties of a new class of linked anthramycin analogs," Chemical Abstracts, Abstract No. 239940r, vol. 114, No. 25, 25 899-903 (1991).
Feild, J.A., et al., "Cloning and Functional Characterization of a Sodium-Dependent Phosphate Transporter Expressed in Human Lung and Small Intestine," (1999) Biochem. Biophys. Res. Commun. 258 (3):578-582.
Fey, T. et al., "Silica-supported Tempo catalyst: synthesis and application in the anelli oxidation of alcohols," J. Org. Chem. (2001) 66:8154-8159.
Fields, G. and Noble, R. (1990) "Solid phase peptide synthesis utilizing 9-fluoroenylmethoxycarbonyl amino acids", Int. J. Peptide Protein Res. 35:161-214.
Firsching, A. et al., "Antiproliferative and angiostatic activity of suramin analogues," Cancer Res. (1995) 55:4957-4961.
Fisch et al., "Site-specific modification of a fragment of a chimeric monoclonal antibody using reverse proteolysis." Bioconjug Chem. Mar.-Apr. 1992; 3(2):147-53.
Flanagan et al., "The ephrins and Eph receptors in neural development," Annu. Rev. Neurosci. 21:309-345 (1998).
Fludarabine, NCBI Pubchem reference 657237.
Foloppe, M.P. et al., "DNA-binding properties of pyrrolo[2,1-c][1,4]benzodiazephine N10-C11 amidines," Eur. J. Med. Chem., 31, 407-410 (1996).
Fox et al., "cDNA cloning and tissue distribution of five human EPH-like receptor protein-tyrosine kinases," Oncogene 10 (5):897-905 (1995).
Fuchs S., et al., "Functional Characterization of Three Mutations of the Endothelin B Receptor Gene in Patients with Hirschsprung's Disease: Evidence for Selective Loss of Gi Coupling," Mol. Med. 7, 115-124, 2001.
Fujisaku et al., "Genomic Organization and Polymorphisms of the Human C3d/Epstein-Barr Virus Receptor," (1989) J. Biol. Chem. 264 (4):2118-2125.
Fujisawa Pharmaceutical Co. Ltd., "Benzodiazepine derivatives," SciFinder Scholar, 2-3 (2002).
Fujisawa Pharmaceutical Co., Ltd., Abstract No. 139983k,"Benzodiazepine derivatives", Chemical Abstracts, vol. 99, No. 17, 603 (1983).
Fujisawa Pharmaceutical Co., Ltd., Abstract No. 72145x,"Benzodiazepine derivatives", Chemical Abstracts, vol. 98, No. 9, 638 (1983).
Fukuyama, T. et al., "Total Synthesis of (+)-Porothramycin B," Tetrahedron Letters, vol. 34, 16, 2577-2580 (1993).
Gallmeier, E., "Targeted disruption of FANCC and FANCG in human cancer provides a preclinical model for specific therapeutic options," Gastroenterology (2006) 130(7):2145-2154.
Gary S.C., et al., "cDNA cloning chromosomal localization, and expression analysis of human BEHAB/brevican, a brain specific proteoglycan regulated during cortical development and in glioma," Gene 256, 139-147, 2000.
Gaugitsch, H.W., et al., "A novel transiently expressed, integral membrane protein linked to cell activation. Molecular cloning via the rapid degradation signal AUUUA.," (1992) J. Biol. Chem. 267 (16):11267-11273.
Gavezzotti, A., "Are crystal structures predictable?" Acc. Chem. Res. (1994) 27:309-314.
Geiser et al "Automation of solid-phase peptide synthesis" in Macromolecular Sequencing and Synthesis, Alan R. Liss, Inc., 1988, pp. 199-218.
Gemcitabine, DrugBank reference DB00441.
Gemcitabine, NCBI Pubchem reference 60750.
Genbank accession No. 11038674 (2013).
Genbank accession No. AAA60137, 1995.
Genbank accession No. AAC51773, 2005.
Genbank accession No. AAD22635, 1999.

(56) References Cited

OTHER PUBLICATIONS

Genbank accession No. AAF25807, Mar. 10, 2010.
Genbank accession No. AAH32229 (2006).
Genbank accession No. AAH46618 (2006).
Genbank accession No. AAL07473, 2001.
Genbank accession No. AB040878 (2001).
Genbank accession No. AF116456 (1999).
Genbank accession No. AF125304.1, 1999.
Genbank accession No. AF177937, version No. AF177937.1, Mar. 10, 2010.
Genbank accession No. AF179274 (2001).
Genbank accession No. AF229053 (2000).
Genbank accession No. AF343662 (2001).
Genbank accession No. AF343663 (2001).
Genbank accession No. AF343664 (2001).
Genbank accession No. AF343665 (2001).
Genbank accession No. AF361486 (2003).
Genbank accession No. AF369794 (2001).
Genbank accession No. AF397453 (2001).
Genbank accession No. AF414120.1, 2001.
Genbank accession No. AF455138 (2003).
Genbank accession No. AJ297436 (2008).
Genbank accession No. AK026467 (2006).
Genbank accession No. AK089756 (2010).
Genbank accession No. AK090423 (2006).
Genbank accession No. AK090475 (2006).
Genbank accession No. AL834187 (2008).
Genbank accession No. AX092328 (2001).
Genbank accession No. AY158090 (2003).
Genbank accession No. AY260763 (2003).
Genbank accession No. AY275463 (2003).
Genbank accession No. AY358085 (2003).
Genbank accession No. AY358628 (2003).
Genbank accession No. AY358907 (2003).
Genbank accession No. AY506558 (2004).
Genbank Accession No. BAB15489.1 (2006).
Genbank accession No. BC017023 (2006).
Genbank accession No. CAA53576.1, 2008.
Genbank accession No. CAA76847.1 (2001).
Genbank accession No. CAF85723 (2004).
Genbank accession No. CQ782436 (2004).
GenBank Accession No. gi:23238190.
GenBank Accession No. gi:23238193.
GenBank Accession No. gi:23238196.
GenBank Accession No. gi:40354198, 2007.
Genbank accession No. M11730 (1995).
Genbank accession No. M18112.1, 1995.
Genbank accession No. M18728 (1995).
Genbank accession No. M26004 (1993).
Genbank accession No. M76125 (1995).
Genbank accession No. NM_000626 (2013).
Genbank accession No. NM_001203 (2013).
Genbank accession No. NM_003212 (2013).
Genbank accession No. NM_003486 (2013).
Genbank accession No. NM_004442 (2013).
Genbank accession No. NM_005823 (2013).
Genbank accession No. NM_006424 (2013).
Genbank accession No. NM_009465 (2019).
Genbank accession No. NM_012449 (2013).
Genbank accession No. NM_017636 (2013).
Genbank accession No. NM_030764 (2013).
Genbank accession No. NP_002111.1 (2013).
Genbank accession No. NP_001194 (2013).
Genbank accession No. NP_001707.1 (2013).
Genbank accession No. NP_001773.1 (2013).
Genbank accession No. NP_001774.10 (2013).
Genbank accession No. NP_002552.2 (2013).
Genbank accession No. NP_003203 (2013).
Genbank accession No. NP_005573.1 (2007).
Genbank accession No. NP_112571.1 (2007).
Genbank accession No. U64863, 2005.
Genbank accession No. X75962, 2008.
Geoghegan & Stroh, "Site-Directed Conjugation of Nonpeptide Groups to Peptides and Proteins via Periodate Oxidation of a 2-Amino Alcohol. Application to Modification at N-Terminal Serine," (1992) Bioconjugate Chem. 3:138-146.
Getz et al., "A Comparison between the Sulfhydryl Reductants Tris(2-carboxyethyl)phosphine and Dithiothreitol for Use in Protein Biochemistry," (1999) Anal. Biochem. vol. 273:73-80.
GITR Agonist MEDI1873, NCI thesaurus code C124651.
Glynne-Jones et al., "Tenb2, A Proteogl Ycan Identified in Prostate Cancer That Is Associated With Disease Progression and Androgen Independence," (2001) Int J Cancer. Oct. 15; 94(2): 178-184.
Gomez et al., "Effect of temperature, pH, dissolved oxygen, and hydrolysate on the formation of triple light chain antibodies in cell culture." Biotechnol Prog. Sep.-Oct. 2010; 26(5):1438-45.
Gomez et al., "Triple light chain antibodies: factors that influence its formation in cell culture." Biotechnol Bioeng. Mar. 1, 2010; 105(4):748-60.
Gonzalez et al. "Abstract 3204: INCAGN01949: an anti-OX40 agonist antibody with the potential to enhance tumor-specific T-cell responsiveness, while selectively depleting intratumoral regulatory T cells." Proceedings: AACR 107th Annual Meeting 2016; Apr. 16-20, 2016.
Gordon et al., "Somatic hypermutation of the B cell receptor genes B29 (Igβ, CD79b) and mb1 (Igα, CD79a)," PNAS, 2003, vol. 100, No. 7, 4126-4131.
Greene & Wuts, Protective Groups in Organic Synthesis, John Wiley & Sons, 2nd ed., Ch 7, 315-345 (1991).
Greene, et al., Protective Groups in Organic Synthesis, John Wiley & Sons (1999) 3rd Edition, 23-200.
Greene, et al., Protective Groups in Organic Synthesis, John Wiley & Sons (1999) 3rd Edition, 503-549.
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.
Gregson, S.J. et al., "Linker length modulates Dna cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.
Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.
Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.
Gregson, S.J. et al., "Design, Synthesis and Evaluation of a Novel Pyrrolobenzodiazepine Dna-Interactive Agent with Highly Efficient Cross-Linking Ability and Potent Cytotoxicity", J. Med. Chem., 44: 737-748 (2001).
Gregson, S.J. et al., "Effect of C2-exo Unsaturation on the Cytotoxicity and DNA-Binding Reactivity of Pyrrolo[2,1-c]1,4]benzodiazepines", Bioorganic & Medicinal Chemistry Letters, 10: 1845-1847 (2000).
Gu Z., et al., "Prostate stem cell antigen (PSCA) expression increases with high gleason score, advanced stage and bone metastasis in prostate cancer," Oncogene 19, 1288-1296, 2000.
Guichard, S.M., "Influence of P-glycoprotein expression on in vitro cytotoxicity and in vivo antitumour activity of the novel pyrrolobenzodiazepine dimer SJG-136," Eur. J. Cancer (2005) 41(12):1811-1818.
Guiotto, A. et al., "Synthesis of novel C7-aryl substituted pyrrolo[2,1-c][1,4]benzodiazepines (PBDs) via Pro-N10-troc protection and suzuki coupling," Bioorganic & Medicinal Chemistry Letters, 8, No. 21, 3017-3018 (1998).
Guselnikov et al., "A family of highly diverse human and mouse genes structurally links leukocyte FcR, gp42 and PECAM-1," Immunogenetics 54 (2):87-95 (2002).

(56) References Cited

OTHER PUBLICATIONS

Ha et al., "Molecular Cloning and Expression Pattern of a Human Gene Homologous to the Murine mb-1 Gene," (1992) J. Immunol. 148(5):1526-1531.
Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004) 44:202.
Hadjivassileva, T., "Interactions of pyrrolobenzodiazepine dimers and duplex DNA from methicillin-resistant Staphylococcus aureus," Int. J. Antimicrob. Agents (2007) 29(6):672-678.
Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.
Haendler B., et al., "Molecular Cloning of Human Endothelin (ET) Receptors ETA and ETB," J. Cardiovasc. Pharmacal. 20, s1-S4, 1992.
Hamaguchi, A., "DNA cross-linking and in vivo antitumour activity of the extended pyrrolo[2,1- c][1,4]benzodiazepine dimer SG2057 (DRG-16)," EJC Supplements (Nov. 2006) 4(12):96.
Hamann P. "Monoclonal antibody-drug conjugates," (2005) Expert Opin. Ther. Patents 15(9):1087-1103.
Hamblett et al., "Effects of Drug Loading on the Antitumor Activity of a Monoclonal Antibody Drug Conjugate," (2004) Clin. Cancer Res. 10:7063-7070.
Hara et al., "DC 102, a new glycosidic pyrrolo(1,4)benzodiazepine antibiotic produced by Streptomyces sp.", J. Antibiotics, 41, 702-704 (1988).
Hartley, "The development of pyrrolobenzodiazepines as antitumour agents", Expert Opinion on Investigational Drugs, Ashley Publications Ltd., vol. 28, No. 6, Jan. 1, 2011, pp. 733-744.
Hartley, J.A. et al., "SG2285, a novel C2-aryl-substituted pyrrolobenzodiazepine dimer prodrug that cross-links DNA and exerts highly potent antitumor activity," Cancer Res., Sep. 2010, 70(17):6849-6858.
Hartley, J.A. et al., "SJG-136 (NSC 694501), a novel rationally designed DNA minor groove interstrand cross-linking agent with potent and broad spectrum antitumor activity. Part 1: Cellular pharmacology, in vitro and initial in vivo antitumor activity," Cancer Res. (2004) 64:6693-6699.
Hartley, J.A., "In vitro antitumor activity and in vivo DNA interstrand crosslinking by the novel pyrrolobenzodiazepine dimer SJG-136 (NSC 694501)," Proceedings of the American Association for Cancer Research Annual Meeting (Mar. 2002) 43:489.
Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.
Hashimoto et al., "Chromosomal localization, genomic structure, and allelic polymorphism of the human CD79a (Ig-alpha/mb-1) gene," (1994) Immunogenetics 40(4):287-295.
Hay et al., "A 2-Nitroimidazole Carbamate Prodrug of 5-Amin0-1-(Chloromethyl)-3-[(5,6,7-Trimethoxyindol-2-Yl)Carbonyl]-1,2-Dihydr0-3h-Benz[E]Indole (Amino-Seco-Cbi-Tmi) For Use With Adept and Gdept," (1999) Bioorg. Med. Chem. Lett. 9:2237-2242.
Herdwijn et al., "Synthesis of trans(+)6-phenoxyacetamido-1-methylene-3,3-dicarboxymethyl-1-carbapenam," Canadian Journal of Chemistry. 1982, 60, 2903-2907.
Hermanson, G.T., "Heterobifunctional Cross-linkers," (1996) Bioconjugate Techniques; Academic Press: New York, p. 228-286.
Hermanson, G.T., Bioconjugate Techniques, Academic Press: San Diego, Calif. (1996)—(Table of Contents Only).
Hezareh et al., "Effector function activities of a panel of mutants of a broadly neutralizing antibody against human immunodeficiency virus type 1." J Virol. Dec. 2001; 75(24):12161-8.
Hochhauser, D., "Phase I study of sequence-selective minor groove DNA binding agent SJG-136 in patients with advanced solid tumors," Clin. Cancer Res., Mar. 2009, 15(6):2140-2147.
Hochlowski, J. et al., "Abbeymycin, a new anthramycin-type antibiotic produced by a streptomycete," J. Antibiotics, 40, 145-148 (1987).
Hofstra R.M.W., et al., "A homozygous mUtation in the endothelin-3 gene associated with a combined Waardenburg type 2 and Hirschsprung phenotype (Shah-Waardenburg syndrome)" Nat. Genet. 12, 445-447, 1996.
Hofstra R.M.W., et al., "Mutations in Hirschsprung Disease: When Does a Mutation Contribute to the Phenotype," Eur. J. Hum. Genet. 5, 180-185, 1997.
Holland et al. "R428, a Selective Small Molecule Inhibitor of Axl Kinase, Blocks Tumor Spread and Prolongs Survival in Models of Metastatic Breast Cancer." Cancer Res 2010; 70:1544-1554.
Horie et al., "Identification and Characterization of TMEFF2, a Novel Survival Factor for Hippocampal and Mesencephalic Neurons," (2000) Genomics 67: 146-152.
Howard, et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem., Sep. 2009, In Press, 4 pages now: Sep. 2009, 19:6463-6466.
Howard, P.W. et al., "The design, synthesis and biological evaluation of a set of C2-aryl substituted pyrrolo[2,1- c][1,4]benzodiazepine dimers," EJC Supplements (2006) 4(12):95—Poster Abstract 301.
Howard, P.W., "Design, synthesis and biological evaluation of novel C2-aryl-substituted pyrrolo[2,1- c][1,4]benzodiazepine monomers," Proceedings of the American Association for Cancer Research Annual Meeting (Apr. 2006) 47:132.
Hubert, R.S., et al., "STEAP: A prostate-specific cell-surface antigen highly expressed in human prostate tumors," (1999) Proc. Natl. Acad. Sci. U.S.A. 96 (25):14523-14528.
Humphreys et al., "Formation of dimeric Fabs in Escherichia coli: effect of hinge size and isotype, presence of interchain disulphide bond, Fab' expression levels, tail piece sequences and growth conditions." J Immunol Methods. Dec. 1, 1997; 209(2):193-202.
Hurley, L. and Needham-Vandevanter, D., "Covalent Binding of Antitumor Antibiotics in the Minor Groove of DNA. Mechanism of Action of CC-1065 and the yrrolo(1,4)benzodiazepines," Acc. Chem. Res., 19, 230-237 (1986).
Hutterer et al., "Axl and growth arrest-specific gene 6 are frequently overexpressed in human gliomas and predict poor prognosis in patients with glioblastoma multiforme." Clin Cancer Res. Jan. 1, 2008;14(1):130-8.
Ide et al., "Cloning of human bone morphogenetic protein type IB receptor (BMPRIB) and its expression in prostate cancer in comparison with other BMPRs," Oncogene (1997) 14, 1377-1382.
Iida, H. et al. "Design and synthesis of pyrrolo[2,1-c][1,4]benzodiazepine (PBD)-polyaminoalkyl conjugates by the use of SNA4 reaction 2-nitro-5-fluorobenzoate precursor as key reaction," Heterocycles (2004) 62:693-711.
International Search Report and Written Opinion for Application No. PCT/EP2016/058369 dated Jun. 20, 2016 (16 pages).
International Search Report and Written Opinion for Application No. PCT/EP2012/070233 dated Jan. 28, 2013 (8 pages).
International Search Report and Written Opinion for Application No. PCT/EP2013/071352 dated Feb. 5, 2014 (14 pages).
International Search Report and Written Opinion for Application No. PCT/GB2015/052629 dated Nov. 2, 2015 (12 pages).
International Search Report and Written Opinion for Application No. PCT/US2011/032668 dated May 26, 2011 (12 pages).
Itoh et al., "Application of Inverse Substrates to Trypsin-Catalyzed Peptide Synthesis" Bioorg. Chem., 24(1): 59-68 (1996).
Itoh et al., "Sibanomicin, a new pyrrolo(1,4)benzodiazepine antitumor antibiotic produced by a Micromonospora sp." J. Antibiotics, 41, 1281-1284 (1988).
Janjigian, Y.Y., "A phase I trial of SJG-136 (NSC#694501) in advanced solid tumors," Cancer Chemotherapy and Pharmacology, Aug. 2009, 65(5):833-838.
Jeffrey et al., "Development and properties of beta-glucuronide linkers for monoclonal antibody-drug conjugates." Bioconjugate Chemistry, 5, 2006, 17, 831-840. (Abstract).

(56) References Cited

OTHER PUBLICATIONS

Jeffrey, S.C., "Design, synthesis, and in vitro evaluation of dipeptide-based antibody minor groove binder conjugates," J. Med. Chem. (2005) 48(5):1344-1358.
Jespers, L. S., "Guiding the Selection of Human Antibodies from Phage Display Repertoires to a Single Epitope of an Antigen" Nature Biotech., 12, 899-903 (1994).
Jia, L., "Interspecies differences in pharmacokinetics and time-dissociated toxicokinetics of SJG-136," Proceedings of the American Association for Cancer Research Annual Meeting (Mar. 2004) 45:487.
Jia, L., "Use of the comet assay as a surrogate biomarker for the in vivo measurement of DNA damage to lymphocytes," Proceedings of the American Association for Cancer Research Annual Meeting (Mar. 2004) 45:452-453.
Johnson & Goldin, "The clinical impact of screening and other experimental tumor studies." Cancer Treat Rev. Mar. 1975; 2(1):1-31.
Jones et al., "Releasable Luciferin—Transporter Conjugates: Tools for the Real-Time Analysis of Cellular Uptake and Release," J. Am. Chem. Soc., 2006, 128, 6526-6527.
Jonsson et al., "Human class II DNA and DOB genes display low sequence variability," (1989) Immunogenetics 29(6):411-413.
Jordan, V.C., "Tamoxifen: a most unlikely pioneering medicine," Nature Reviews: Drug Discovery (2003) 2:205-213.
Junutula et al., "Rapid identification of reactive cysteine residues for site-specific labeling of antibody-Fabs," (2008) Jour of Immun. Methods 332:41-52.
Junutula, et al., "Site-specific conjugation of a cytotoxic drug to an antibody improves the therapeutic index," 2008b Nature Biotech., 26(8):925-932.
Kabat et al., Sequences of proteins of immunological interest, 5 ed. (NIH National Technical Information Service, 1991).
Kamal et al., "Synthesis and Dna-binding affinity of A-C8/C-C2 alkoxyamido-linked pyrrolo[2,1- c][1,4]benzodiazepine dimers" Biorg. Med. Chem. Lett. (2003) 13(22): 3955-3958.
Kamal, A. et al., "Design, synthesis and evaluation of new noncross-linking pyrrolobenzodiazepine dimers with efficient DNA binding ability and potent antitumor activity," J. Med. Chem. (2002) 45:4679-4688.
Kamal, A., "Development of pyrrolo[2,1-c][1,4]benzodiazepine beta-galactoside prodrugs for selective therapy of cancer by ADEPT and PMT," Chemmedchem (2008) 3:794-802.
Kamal, A., "Remarkable DNA binding affinity and potential anticancer activity of pyrrolo[2,1- c][1,4]benzodiazepine-naphthalamide conjugates linked through piperazine side-armed alkane spacers," Bioorg. Med. Chem. (2008) 16(15):7218-7224.
Kamal, A., "Remarkable enhancement in the DNA-binding ability of C2-fluoro substituted pyrrolo[2,1- c][1,4]benzodiazepines and their anticancer potential," Bioorg. Med. Chem., Jan. 2009, 17(4):1557-1572.
Kamal, A., "Synthesis of fluorinated analogues of SJG-136 and their DNA-binding potential," Bioorg. Med. Chem. Lett (2004) 14(22):5699-5702.
Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).
Kamal, A., et al., "Synthesis of Pyrrolo [2,1-c][1,4]-Benzodiazepene Antibiotics: Oxidation of Cyclic Secondary Amine with TPAP", Tetrahedron, v. 53, No. 9, 3223-3230 (1997).
Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.
Kaneko, T. et al., "Bicyclic and tricyclic analogues of anthramycin," J. Med. Chem. (1985) 28:388-392.
Kang, G.-D. et al., "Synthesis of a novel C2-aryl substituted 1,2-unsaturated pyrrolobenzodiazepine," Chem. Commun. (2003) 1680-1689.

Kasahara et al., "Nucleotide sequence of a chimpanzee DOB eDNA clone," (1989) Immunogenetics 30(1):66-68.
King et al., "Facile synthesis of maleimide bifunctional Jinkers," (2002) Tetrahedron Letters 43:1987-1990.
Kingsbury et al., ""A Novel Peptide Delivery System Involving Peptidase Activated Prodrugs as Antimicrobial Agents. Synthesis and Biological Activity of Peptidyl Derivatives of 5 Fluorouracil,"" (1984) J. Med. Chem. 27:1447-1451.
Kohler et al., "Continuous cultures of fused cells secreting antibody of predefined specificity," (1975) Nature 256:495-497.
Kohn, K., "Anthramycin," Antibiotics III, Springer-Verlag, NY, 3-11 (1975).
Kojima et al., "Molecular Cloning and Expression of Megakaryocyte Potentiating Factor eDNA," The Journal of Biological Chemistry, vol. 270, No. 37, Issue of Sep. 15, pp. 21984-21990, 1995.
Konishi, M. et al., "Chicamycin, a new antitumor antibiotic II. Structure determination of chicamycins A and B," J. Antibiotics, 37, 200-206 (1984).
Kovtun et al., "Antibody-Drug Conjugates Designed to Eradicate Tumors with Homogeneous and Heterogeneous Expression of the Target Antigen," (2006) Cancer Res. 66(6):3214-3121.
Kreitman & Pastan "Immunotoxins for targeted cancer therapy." Adv Drug Deliv Rev. Apr. 6, 1998; 31(1-2):53-88.
Kuhns J.J., et al., "Poor Binding of a HER-2/neu Epitope (GP2) to HLA-A2.1 Is due to a Lack of Interactions with the Center of the Peptide," J. Biol. Chem. 274, 36422-36427, 1999.
Kumaran et al., "Conformationally driven protease-catalyzed splicing of peptide segments: V8 protease-mediated synthesis of fragments derived from thermolysin and ribonuclease A." Protein Sci. Oct. 1997; 6(10):2233-41.
Kunimoto et al., "Mazethramycin, a new member of anthramycin group antibiotics," J. Antibiotics, 33, 665-667 (1980).
Kurebayashi et al., "Isolation and characterization of a new human breast cancer cell line, KPL-4, expressing the Erb B family receptors and interleukin.6," (1999) Brit. Jour. Cancer 79(5-6):707-717.
Lambert J., "Drug-conjugated monoclonal antibodies for the treatment of cancer," (2005) Current Opin. In Pharmacal. 5:543-549.
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Larhammar et al., "Sequence of Gene and eDNA Encoding Murine Major Histocompatibility Complex Class II Gene AP2*," (1985) J. Biol. Chem. 260(26):14111-14119.
Launay et al., "TRPM4 Is a Ca2+-Activated Nonselective Cation Channel Mediating Cell Membrane Depolarization," Cell 109 (3):397-407 (2002).
Law et al., "Lymphocyte Activation Antigen CD70 Expressed by Renal Cell Carcinoma Is a Potential Therapeutic Target for Anti-CD70 Antibody-Drug Conjugates," (2006) Cancer Res. 66(4):2328-2337.
Lazar et al., "A molecular immunology approach to antibody humanization and functional optimization" Molecular Immunology, 2007, 44(8), 1986-1998.
Le et al., "Primary structure and expression of a naturally truncated human P2X ATP receptor subunit from brain and immune system," (1997) FEBS Lett. 418(1-2):195-199.
Leabman; et al., "Effects of altered FcyR binding on antibody pharmacokinetics in cynomolgus monkeys." MAbs. Nov.-Dec. 2013; 5(6):896-903.
Leber, J.D. et al., "A revised structure for sibiromycin," J. Am. Chem. Soc., 110, 2992-2993 (1988).
Leimgruber, W. et al., "Isolation and characterization of anthramycin, a new antitumor antibiotic," J. Am. Chem. Soc., 87, 5791-5793 (1965).
Leimgruber, W. et al., "The structure of anthramycin," J. Am. Chem. Soc., 87, 5793-5795 (1965).

(56) References Cited

OTHER PUBLICATIONS

Leimgruber, W. et al., "Total synthesis of anthramycin," J. Am. Chem. Soc., 90, 5641-5643 (1968).
Leonard et al., "Phase I/II trial of epratuzumab (humanized anti-CD22 antibody) in indolent non-Hodgkin's lymphoma," J. Clin. Oncology (2003) 21(16):3051-3059.
Leonard et al., "Preclinical and clinical evaluation of epratuzumab (anti-CD22 IgG) in B-cell malignancies," Oncogene (2007) 26:3704-3713.
Leung et al., "Construction and characterization of a humanized, internalizing, B-cell (CD22)-specific, leukemia/lymphoma antibody, LL2," Mol. Immunol. (1995) 32(1718):1413-1427.
Levenson et al., "MCF-7: The First Hormone-responsive Breast Cancer Cell Line," (1997) Cancer Res. 57(15):3071-3078.
Lewis Phillips et al., "Targeting HER2-Positive Breast Cancer with Trastuzumab-DM1, an Antibody—Cytotoxic Drug Conjugate," Cancer Res, 2008, 68: (22).
Li et al., "A Mini-Review for Cancer Immunotherapy: Molecular Understanding of PD-1/PD-L1 Pathway & Translational Blockade of Immune Checkpoints." Int. J. Mol. Sci. 2016, 17(7), 1151.
Liang et al., "The Gene for a Novel Transmembrane Protein Containing Epidermal Growth Factor and Follistatin Domains Is Frequently Hypermethylated in Human Tumor Cells," (2000) Cancer Res. 60:4907-4912.
Lin et al., "The PD-1/PD-L1 complex resembles the antigen-binding Fv domains of antibodies and T cell receptors" PNAS, Feb. 26, 2008., 105(8): 3011-3016.
Linden et al., "Dose-fractionated radioimmunotherapy in non-Hodgkin's lymphoma using DOTA-conjugated, 90Y-radiolabeled, humanized anti-CD22 monoclonal antibody, epratuzumab," J. Clin. Cancer Res. (2005) 11:5215-5222.
Lonberg, "Fully Human antibodies from transgenic mouse and phage display platforms" Curr. Opinion, 20(4), 450-459 (2008).
Lown et al., "Molecular Mechanism of Binding of Pyrrolo(1,4)benzodiazepine antitumour agents to deoxyribonucleic acid —anthramycin and tomaymycin," Biochem. Pharmacol. (1979), 28 (13), 2017-2026.
Lu et al., "Homeostatic regulation of the immune system by receptor tyrosine kinases of the Tyro 3 family." Science. Jul. 13, 2001; 293(5528):306-11.
Manfre et al., "Syntheses of Proline Analogues as Potential Mechanism-Based Inhibitors of Proline Dehydrogenase: 4-Methylene-L-, (E)- and (Z)-4-(Fluoromethylene)-L-, cis- and trans-5-Ethynyl-(±)-, and cis- and trans-5-Vinyl-L-proline," J. Org. Chem. 1992, 57, 2060-2065.
Marin, D., "Voltammetric studies of the interaction of pyrrolo[2,1-c][1,4]benzodiazepine (PBD) monomers and dimers with DNA," J. Electroanal. Chem. (2006) 593(1-2):241-246.
Marks et al., "By-passing Immunization, Human Antibodies from V-gene Libraries Displayed on Phage," (1991) J. Mol. Biol., 222:581-597.
Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.
Mastroberardino et al., "Amino-acid transport by heterodimers of 4F2hc/CD98 and members of a permease family," Nature 395 (6699):288-291 (1998).
Melaragno et al., "Increased expression of Axl tyrosine kinase after vascular injury and regulation by G protein-coupled receptor agonists in rats." Circ Res. Oct. 5, 1998;83(7):697-704.
Melaragono et al., "The Gas6/Axl system: a novel regulator of vascular cell function." Trends Cardiovasc Med. Nov. 1999; 9(8):250-3.
Mendoza et al., "Inhibition of Ligand-mediated HER2 Activation in Androgen-independent Prostate Cancer," (2002) Cancer Res. 62:5485-5488.
Miller et al., "Design, Construction, and in Vitro Analyses of Multivalent Antibodies," (2003) Jour. of Immunology 170:4854-4861.

Miller et al., "IRTAs: a new family of immunoglobulinlike receptors differentially expressed in B cells," Blood 99 (8):2662-2669 (2002).
Miller et al., "Reduced Proteolytic Shedding of Receptor Tyrosine Kinases Is a Post-Translational Mechanism of Kinase Inhibitor Resistance." Cancer Discov. Apr. 2016; 6(4):382-99.
Miura et al., "Molecular cloning of a human RP105 homologue and chromosomal localization of the mouse and human RP105 genes (Ly64 and LY64)." Genomics. Dec. 15, 1996; 38(3):299-304.
Miura et al., "RPIOS Is Associated With MD-1 and Transmits an Activation Signal in Human B Cells," (1998) Blood 92:2815-2822.
Moore M., et al., "Molecular cloning of the eDNA encoding the Epstein-Barr virus/C3d receptor (complement receptor type 2) of human B lymphocytes," Proc. Natl. Acad. Sci. U.S.A. 84, 9194-9198, 1987.
Morea et al., "Antibody modeling: implications for engineering and design." Methods. Mar. 2000; 20(3):267-79.
Mori, M. et al., "Total syntheses of prothracarcin and tomaymycin by use of palladium catalyzed carbonylation," Tetrahedron (1986) 42(14):3793-3806.
Morrison et al., "Chimeric human antibody molecules: Mouse antigen-binding domains with human constant region domains," (1984) Proc. Natl. Acad. Sci. USA, 81:6851-6855.
Mountzouris, J.A. et al., "Comparison of a DSB-120 DNA interstrand cross-linked adduct with the corresponding bis-Tomamycin adduct," J. Med. Chem. (1994) 37:3132-3140.
Muller et al., "Cloning and sequencing of the eDNA encoding the human homologue of the murine immunoglobulin-associated protein B29," (1992) Eur. J. Immunol. 22 (6): 1621-1625.
Mungall A.J., et al., "The DNA sequence and analysis of human chromosome 6," Nature 425, 805-811, 2003.
Nagasaka, T. et al., "Stereoselective Synthesis of Tilivalline," Tetrahedron Letters, 30:14, 1871-1872 (1989).
Nagase T., et al., "Prediction of the Coding Sequences of Unidentified Human Genes. XVII. The Complete Sequences of 100 New eDNA Clones from Brain Which Code for Large Proteins in vitro," (2000) DNA Res. 7 (2):143-150.
Nakamuta M., et al., "Cloning and Sequence Analysis of a cDNA Encoding Human Non-Selective Type of Endothelin Receptor," Biochem. Biophys. Res. Commun. 177, 34-39, 1991.
Nakayama et al., "Altered Gene Expression upon Bcr Cross-Linking in Burkitt's Lymphoma B Cell Line," (2000) Biochem. Biophys. Res. Commun. 277(1):124-127.
Narayanaswamy, M., "A novel HPLC/MS assay to measure DNA interstrand cross-linking efficacy in oligonucleotides of varying sequence," EJC Supplements (Nov. 2006) 4(12):92-93.
Narayanaswamy, M., "An assay combining high-performance liquid chromatography and mass spectrometry to measure DNA interstrand cross-linking efficiency in oligonucleotides of varying sequences," Anal. Biochem. (2008) 374(1):173-181.
Narayanaswamy, M., "Use of HPLC-MS to characterize novel mono and intrastrand cross-linked DNA adducts formed by the sequence-selective DNA-interactive agent SJG-136," Proceedings of the American Association for Cancer Research Annual Meeting (Apr. 2007) 48:760-761.
Narukawa, Y., "General and efficient synthesis of 2-alkylcarbapenems synthesis of dethia carba analogs of clinically useful carbapenems via palladium-catalyzed cross-coupling reaction," Tetrahedron (1997) 53:539-556.
Naruse et al., "The HLA-DOB gene displays limited polymorphism with only one amino acid substitution," (2002) Tissue Antigens 59:512-519.
Neuberger and Williams, "The intron requirement for immunoglobulin gene expression is dependent upon the promoter," (1988) Nucleic Acids Res. 16:6713-6724.
Neuenschwander et al., "Critical aspects of the Bayesian approach to phase I cancer trials." Statistics in Medicine 2008, 27:2420-2439.
Nicolaou et al., "Calicheamicin θ: A Rationally Designed Molecule with Extremely Potent and Selective DNA Cleaving Properties and Apoptosis Inducing Activity," Angew Chem. Intl. Ed. Engl. (1994) 33:183-186.
Nilius et al., "Voltage Dependence of the Ca2+-activated Cation Channel TRPM4," The Journal of Biological Chemistry, vol. 278, No. 33, Issue of Aug. 15, pp. 30813-30820, 2003.

(56) References Cited

OTHER PUBLICATIONS

Niraparib, NCBI Pubchem reference 24958200.
Nivolumab, DrugBank Reference DB09035.
Nocentini et al. "A new member of the tumor necrosis factor/nerve growth factor receptor family inhibits T cell receptor-induced apoptosis."Proc Natl Acad Sci U S A. Jun. 10, 1997;94(12):6216-21.
Nomi et al. "Clinical significance and therapeutic potential of the programmed death-1 ligand/programmed death-1 pathway in human pancreatic cancer." Clin Cancer Res. Apr. 1, 2007; 13(7):2151-7.
O'Neil, Chemical Abstract No. 171573p, "The synthesis of Functionalized Pyrrolo-[2,1-c][1,4]-Benzodiazepines", Chemical Abstracts, vol. 126, No. 13, 618 (1997).
O'Neil, I.A., et al., "The Synthesis of Functionalized Pyrrolo-[2,1-c][1,4]-Benzodiazepines," Synlett, 75-78 (1997).
O'Bryan et al., "The transforming receptor tyrosine kinase, Axl, is post-translationally regulated by proteolytic cleavage." J Biol Chem. Jan. 13, 1995;270(2):551-7.
Ogawa et al., "Molecular cloning of a non-isopeptide-selective human endothelin receptor," Biochem. Biophys. Res. Commun. 178, 248-255, 1991.
Okamoto Y., et al. "Palmitoylation of Human Endothelin B," Biol. Chem. 272, 21589-21596, 1997.
Olaparib, NCBI Pubchem reference 23725625.
O'Neil, I.A. et al., "DPPE: A Convenient Replacement for Triphenylphosphine in the Staudinger and Mitsunobu Reactions", Tetrahedron Letters, vol. 39, No. 42, 7787-7790 (1998).
Paolino et al., "The Role of TAM Family Receptors in Immune Cell Function: Implications for Cancer Therapy." Cancers (Basel) Oct. 21, 2016; 8(10).
Parrish-Novak J., et al., "Interleukins 19, 20, and 24 Signal through Two Distinct Receptor Complexes," J. Biol. Chem. 277, 47517-47523, 2002.
Paul, Fundamental Immunology, 3rd Edition, pp. 292-295.
Payne, G. "Progress in immunoconjugate cancer therapeutics," (2003) Cancer Cell 3:207-212.
PD1 polypeptide corresponds to Uniprot/Swiss-Prot accession No. Q9NZQ7, 2005.
Peggs et al., "Cancer immunotherapy: co-stimulatory agonists and co-inhibitory antagonists." Clin Exp Immunol. Jul. 2009;157(1):9-19.
Pepper, C., "Fludarabine-mediated suppression of the excision repair enzyme ERCC1 contributes to the cytotoxic synergy with the DNA minor groove crosslinking agent SJG-136 (NsSC 694501) in chronic lymphocytic leukaemia cells," Br. J. Cancer (2007) 97(2):253-259.
Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53- independent mechanism of cell kill," Cancer Res. (2004) 64:6750-6755.
Phillips et al., "Targeting HER2-Positive Breast Cancer with Trastuzumab-DM1, an Antibody-Cytotoxic Drug Conjugate," (2008) Cancer Res. 68(22):9280-9290.
Pingault V., et al., "SOX10 mutations in chronic intestinal pseudo-obstruction suggest a complex physiopathological mechanism," (2002) Hum. Genet. 111, 198-206.
Pletnev S., et al., "Characterization of the Recombinant Extracellular Domains of Human Interleukin-20 Receptors and Their Complexe with Interleukin-19 and Interleukin-20," (2003) Biochemistry 42:12617-12624.
Porkaa et al., "Cloning and Characterization of a Novel Six-Transmembrane Protein STEAP2, Expressed in Normal and Malignant Prostate," Lab. Invest. 82 (11):1573-1582 (2002).
Prasad et al.,"Human LAT1, a Subunit of System L Amino Acid Transporter: Molecular Cloning and Transport Function," Biochem. Biophys. Res. Commun. 255 (2), 283-288 (1999).
Preud'Homme et al., "Structure and expression of the mb-1 transcript in human lymphoid cells," (1992) Clin. Exp. Immunol. 90(1):141-146.

Puffenberger E.G., et al., "A Missense Mutation of the Endothelin-B Receptor Gene in Multigenic Hirschsprung's Disease," Cell 79, 1257-1266, 1994.
Puzanov, I., "Phase I and pharmacokinetic trial of SJG-136 administered on a daily x5 schedule," EJC Supplements (Nov. 2006) 4(12):93.
Quintas-Cardama, A., "Sequencing of subcloned PCR products facilitates earlier detetction of BCR-ABL1 and other mutants compared to direct sequencing of the ABL1 kinase domain," Leukemia (2008) 22(4):877-878.
Rahman et al. "Antistaphylococcal activity of DNA-interactive pyrrolobenzodiazepine (PBD) dimers and PBD-biaryl conjugates." J Antimicrob Chemother. Jul. 2012; 67(7):1683-96.
Rahman, K.M., "Effect of microwave irradiation on covalent ligand-DNA interactions," Chem. Commun. (Cambridge, UK), Apr. 2009, 20:2875-2877.
Rahman, K.M., "Rules of DNA adduct formation for pyrrolobenzodiazepine (PBD) dimers," Proceedings of the American Association for Cancer Research Annual Meeting (Apr. 2010) 51:851.
Rahman, K.M., "The pyrrolobenzodiazepine dimer SJG-136 forms sequence-dependent intrastrand DNA cross-lins and monoalkylated adducts in addition to interstrand cross-links," J. Am. Chem. Soc., Sep. 2009, 131(38):13756-13766.
Rao et al., "Influence of diet on mammary cancer in transgenic mice bearing an oncogene expressed in mammary tissue," (1997) Breast Cancer Res. and Treatment 45:149-158.
Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.
Reiter R.E., et al., "Prostate stem cell antigen: A cell surface marker overexpressed in prostate cancer," Proc. Natl. Acad. Sci. U.S.A. 95, 1735-1740, 1998.
Remmers et al., "Conformations of complexes between pyrrolo[1,4]benzodiazepines and DNA segments," J Med Chem. Dec. 1986;29(12):2492-2503.
Rich, I.N., "Validation and development of a predictive paradigm for hemotoxicology using a multifunctional bioluminescence colony-forming proliferation assay," Toxicological Sci. (2005) 87(2):427-441.
Rodrigues et al., "Synthesis and beta-lactamase-mediated activation of a cephalosporin-taxol prodrug," (1995) Chemistry Biology 2:223-227.
Ross et al., "Prostate Stem Cell Antigen as Therapy Target: Tissue Expression and in Vivo Efficacy of an Immunoconjugate," (2002) Cancer Res. 62:2546-2553.
Sagnou, M.J. et al., "Design and Synthesis of Novel Pyrrolobenzodiazepine (PDB) Prodrugs for ADEPT and GDEPT," Bioorganic & Medicinal Chemistry Letters, 10, 2083-2086 (2000).
Sakaguchi et al., "8 lymphocyte lineage-restricted expression of mb-1, a gene with CD3-like structural properties," (1988) EMBO J. 7(11):3457-3464.
Sakamoto A, Yanagisawa M., et al., "Cloning and Functional Expression of Human cDNA for The ETB Endothelin Receptor," Biochem. Biophys. Res. Commun. 178, 656-663, 1991.
Sanderson et al., "In vivo Drug-Linker Stability of an Anti-CD30 Dipeptide-Linked Auristatin Immunoconjugate," (2005) Clin. Cancer Res. 11:843-852.
Scholler et al., "Soluble member(s) of the mesothelin/ megakaryocyte potentiating factor family are detectable in sera from patients with ovarian carcinoma," Proc. Natl. Acad. Sci. USA vol. 96, pp. 11531-11536, Sep. 1999.
Schroder and Lubke, The Peptides, vol. 1. pp. 76-136 (1965) Academic Press.
Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.
Segawa et al., "Growth-related Renal Type II Na/Pi Cotransporter," The Journal of Biolocjcal Chemistry, vol. 277. No. 22, Issue of May 31, pp. 19665-19672, 2002.

(56) References Cited

OTHER PUBLICATIONS

Semba K., et al., "A v-erbB-related protooncogene, c-erbB-2, is distinct from the c-erbB-1 /epidermal growth factor-receptor gene and is amplified in a human salivary gland adenocarcinoma," 15 Proc. Natl. Acad. Sci. U.S.A 82, 6497-6501, 1985.
Servenius et al., "Class II Genes of the Human Major Histocompatibility Complex, The DOBeta Gene Is a Divergent Member of the Class II P Gene Family," (1987) J. Biol. Chem. 262:8759-8766.
Shamis et al., "Bioactivation of Self-Immolative Dendritic Prodrugs by Catalytic Antibody 38C2," (2004) J . Am. Chem. Soc. 126:1726-1731.
Sharkey et al., "Epratuzumab-SN-38: a new antibody-drug conjugate for the therapy of hematologic malignancies," Mol. Cancer Ther. (2012) 11(1):224-234.
Sheikh F., et al., "Cutting Edge: IL-26 Signals through a Novel Receptor Complex Composed of IL-20 Receptor 1 and IL-10 Receptor 21," (2004) J.Immunol, 172, 2006-2010.
Shen et al., "Conjugation site modulates the in vivo stability and therapeutic activity of antibody-drug conjugates," (2012) Nature Biotech., 30(2):184-191.
Shieh et al., "Expression of axl in lung adenocarcinoma and correlation with tumor progression." Neoplasia. Dec. 2005; 7(12):1058-64.
Shimizu, K et al., "Prothracarcin, a Novel Antitumor Antibiotic," J. Antibiotics, 35, 972-978 (1982).
Sinha S.K., et al., "Characterization of the EBV /C3d Receptor on the Human Jurkat T Cell Line: Evidence for a Novel Transcript," (1993) J. Immunol. 150, 5311-5320.
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Smith, P. K. et al., "Measurement of protein using bicinchoninic acid." Anal Biochem. Oct. 1985; 150(1):76-85.
Souillac, P. et al., "Characterization of delivery systems, differential scanning calorimetry," Encyclopedia of Controlled Drug Delivery (1999) 212-227 (pp. 217-218).
Stimmel et al., "Site-specific conjugation on serine right-arrow cysteine variant monoclonal antibodies." J Biol Chem. Sep. 29, 2000; 275(39):30445-50.
Storm et al., "Effect of Small Changes in Orientation on Reaction Rate," (1972) J. Amer. Chem. Soc. 94:5815-5825.
Strausberg et al., "Generation and initial analysis of more than 15,000 full-length human and mouse Edna sequences," (2002) Proc. Natl. Acad. Sci USA 99:16899-16903.
Strop et al., "Location matters: site of conjugation modulates stability and pharmacokinetics of antibody drug conjugates." Chem Biol. Feb. 21, 2013; 20(2):161-7.
Suggitt, M., "The hollow fibre model—facilitating anti-cancer pre-clinical pharmacodynamics and improving animal welfare," Int. J. Oncol. (2006) 29(6):1493-1499.
Suggs, J.W. et al., "Synthesis and structure of anthramycin analogs via hydride reduction of dilactams," Tetrahedron Letters, 26, No. 40, 4871-4874 (1985).
Sukumar et al., "Characterization of MK-4166, a Clinical Agonistic Antibody That Targets Human GITR and Inhibits the Generation and Suppressive Effects of T Regulatory Cells." Cancer Res. Aug. 15, 2017; 77(16):4378-4388.
Sun et al., "Enabling ScFvs as Multi-Drug Carriers: A Dendritic Approach," (2003) Bioorganic & Medicinal Chemistry 11:1761-1768.
Sun et al., "Syntheses of Dendritic Linkers Containing Chlorambucil Residues for the Preparation of Antibody-Multidrug Immunoconjugates," (2002) Bioorganic & Medicinal Chemistry Letters 12:2213-2215.
Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.
Svensson P.J., et al., "Phenotypic variation in a family with mutations in two Hirschsprung-related genes (RET and endothelin receptor B)," Hum. Genet. 103, 145148, 1998.
Swiercz J.M., et al., "Plexin-81 /RhoGEF-mediated Rho A activation involves the receptor tyrosine kinase ErbB-2," J. Cell Biol. 165, 869-880, 2004.
Syrigos and Epenetos, "Antibody Directed Enzyme Prodrug Therapy (ADEPT): A Review of the Experimental and Clinical Considerations," (1999) Anticancer Research 19:605-614.
Tai et al., "Axl promotes cell invasion by inducing MMP-9 activity through activation of NF-kappaB and Brg-1." Oncogene. Jul. 3, 2008; 27(29):4044-55.
Takahashi et al., "Human Fas ligand: gene structure, chromosomal location and species specificity." Int Immunol. Oct. 1994; 6(10):1567-74.
Takeuchi, T. et al., "Neothramycins A and B, New Antitumor Antibiotics," J. Antibiotics, 29, 93-96 (1976).
Tamoxifen, DrugBank reference DB00675, retrieved online https://www.drugbank.ca/.
Tamoxifen, NCBI Pubchem reference 2733526.
Tavolimab, NCI Thesaurus, Code C132267, Retrieved from https://ncit.nih.gov/ncitbrowser/.
Tawaragi Y., et al., "Primary Structure of Nonspecific Crossreacting Antigen (Nca), A Member of Carcinoembryonic Antigen (Cea) Gene Family, Deduced From Cdna Sequence," Biochem. Biophys. Res. Commun. 150, 89-96, 1988.
Tercel, M. et al., "Unsymmetrical DNA cross-linking agents: combination of the CBI and PBD pharmacophores," J. Med. Chem. (2003) 46:2132-2151.
Thompson J.S., et al., "BAFF-R, a Newly Identified TNF Receptor That Specifically Interacts with BAFF," Science 293 (5537), 2108-2111 (2001 ).
Thurston, D. E., "Advances in the study of Pyrrolo[2,1-c][1,4] benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Thurston, D.E. et al., "Effect of A-ring modifications on the DNA-binding behavior and cytotoxicity of pyrrolo[2,1-c][1,4]benzodiazepines", Journal of Medicinal Chemistry, 42:1951-1964 (1999).
Thurston, D.E. et al., "Synthesis of Sequence-selective C8-linked Pyrrolo [2,1c][1,4] Benzodiazepine DNA Interstrand Cross-linking Agent," J. Org. Chem., 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies for the 21st century," Brit. J. Cancer (1999) 80(1):65-85.
Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.
Tiberghien, A.C., "Application of the stille coupling reaction to the synthesis of C2-substituted endo-exo unsaturated pyrrolo[2,1-c][1,4]benzodiazepines (PBDs)," Bioorg. Med. Chem. Lett. (2008) 18(6):2073-2077.
Tigue et al., "MEDI1873, a potent, stabilized hexameric agonist of human GITR with regulatory T-cell targeting potential." Oncoimmunology. Feb. 3, 2017; 6(3):e1280645.
Toki et al., "Protease-Mediated Fragmentation of p-Amidobenzyl Ethers: A New Strategy for the Activation of Anticancer Prodrugs," (2002) J. Org. Chem. 67:1866-1872.
Tonnelle et al., "DO Beta a new chain gene in HLA-D with a distinct regulation of expression," (1985) EMBO J. 4(11):2839-2847.
Touchman et al., "The Genomic Region Encompassing the Nephropathic Cystinosis Gene (CTNS): Complete Sequencing of a 200-kb Seg-

(56) References Cited

OTHER PUBLICATIONS ment and Discovery of a Novel Gene within the Common Cystinosis-Causing Deletion," (2000) Genome Res. 10:165-173.
Tozuka et al., "Studies on tomaymycin. II. Total synthesis of the antitumor antibiotics, E-and Z-tomaymycins," J. Antibiotics (Tokyo) (1983) 36:276-282.
Trail et al., "Monoclonal antibody drug immunoconjugates for targeted treatment of cancer," (2003) Cancer Immunol. Immunother. 52:328-337.
Tsunakawa, M. et al., "Porothramycin, a new antibiotic of the anthramycin group: Production, isolation, structure and biological activity," J. Antibiotics, 41:1366-1373 (1988).
Tsushima et al., "Predominant expression of B7-H1 and its immunoregulatory roles in oral squamous cell carcinoma." Oral Oncol. Mar. 2006; 42(3):268-74.
Tsutsumi M., et al., "Novel endothelin B receptor transcripts with the potential of generating a new receptor," Gene 228, 43-49, 1999.
Uchida et al., "A Novel Epidermal Growth Factor-like Molecule Containing Two Follistatin Modules Stimulates Tyrosine Phosphorylation of erbB-4 in MKN28 Gastric Cancer Cells," (1999) Biochem. Biophys. Res. Commun. 266:593-602.
Umezawa, H. et al., "Mazethramycins," SciFinder Scholar, 2-3 (2002).
Umezawa, H. et al., Chemical Abstract No. 4427a, "Mazethramycins" Chemical Abstracts, vol. 90, No. 1, 428 (1979).
Uniprot Swiss-Prot accession No. P09874, 2019.
Uniprot Swiss-Prot accession No. Q15116, 1997.
Uniprot/Swiss-Prot accession No. P16410, 2019.
Uniprot/Swiss-Prot accession No. P43489, 2019.
UniProtKB/Swiss-Prot: Q9Y5U5.1, 2001.
Vajkoczy et al., "Dominant-negative inhibition of the Axl receptor tyrosine kinase suppresses brain tumor cell growth and invasion and prolongs survival." Proc Natl Acad Sci U S A. Apr. 11, 2006; 103(15):5799-804.
van Geel et al., "Chemoenzymatic Conjugation of Toxic Payloads to the Globally Conserved N-Glycan of Native mAbs Provides Homogeneous and Highly Efficacious Antibody-Drug Conjugates." Bioconjug Chem. Nov. 18, 2015;26(11):2233-42.
Veliparib, NCBI Pubchem reference 11960529.
Vemurafenib, DrugBank reference DB08881, retrieved online from.
Verheij J.B., et al., "ABCD Syndrome Is Caused by a Homozygous Mutation in the EDNRB Gene," Am. J. Med. 15 Genet. 108, 223-225, 2002.
Vippagunta, S.R. et al., "Crystalline solids," Adv. Drug Delivery Rev. (2001) 48:3-26.
Von Hoegen et al., "Identifigation of a Human Protein Homologous to the Mouse Lyb-2 B Cell Differentiation Antigen and Sequence of the Corresponding cDNA," (1990) J. Immunol. 144(12):4870-4877.
Wang et al., "Clinical experience of MEK inhibitors in cancer therapy." Biochim Biophys Acta. Aug. 2007;1773(8):1248-55.
Wang, J.H., "Determination of antitumor agent AJG-136 in human serum by HPLC with tandem mass spectrometric detection (HPLC-MS/MS)," Abstracts of Papers American Chemical Society (Mar. 13, 2005) 229(1):U119.
Webster et al., "Mammary tumorigenesis and metastasis in transgenic mice," (1994) Semin. Cancer Biol. 5:69-76.
Weidner-Wells, M.A. et al., "Photochemical approach to the synthesis of the pyrrolo[1,4]benzodiazepine antibiotics," J. Org. Chem. (1989) 54:5746-5758.
Weinberg, "Anti-OX40 (CD134) administration to nonhuman primates: immunostimulatory effects and toxicokinetic study." J Immunother. Nov.-Dec. 2006; 29(6):575-85.
Weis J.J., et al., "Identification of a partial eDNA clone for the C3d/Epstein-Barr virus receptor of human B lymphocytes: Homology with the receptor for fragments C3b and C4b of the third and fourth components of complement," Proc. Natl. Acad. Sci. U.S.A. 83, 5639-5643, 1986.

Weis J.J., et al., "Structure of the human b lymphocyte receptor for c3d and the epstein-barr virus and relatedness to other members of the family of c3/c4 binding proteins," J. Exp. Med. 167, 1047-1066, 1988.
Wells, G. et al., "Design, synthesis and biophysical and biological evaluation of a series of pyrrolobenzodiazepine-poly(N-methylpyrrole) conjugates," J. Med. Chem. (2006) 49:5442-5461.
Werlen et al., "Site-specific conjugation of an enzyme and an antibody fragment." Bioconjug Chem. Sep.-Oct. 1994; 5(5):411-7.
Wikipedia, "How many types of cancer are there?", 2012, 3 pages; http://wiki.answers.com/Q/How-many-different-types_of cancer_are_there.
Wikipedia, "Management of Cancer," 2012, 1 page; http://en.wikipedia.org/wiki/Management of cancer.
Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.
Wilkinson, G.P., "Pharmacokinetics, metabolism and glutathione reactivity of SJG-136," Br. J. Cancer (2003) 88(Supp. 1):S29.
Wilkinson, G.P., "Preliminary pharmacokinetic and bioanalytical studies of SJG-136 (NSC 694501), a sequence-selective pyrrolobenzodiazepine dimer DNA-cross-linking agent," Investigational New Drugs (2004) 22(3):231-240.
Wilson et al., "eDNA Cloning of the B Cell Membrane Protein CD22: A Mediator of B-B Cell Interactions," (1991) J. Exp. Med. 173:137-146.
Wilson, S.C. et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).
Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", J. Med. Chem. 42: 4028-4041 (1999).
Wines et al., "The IgG Fc contains distinct Fc receptor (FcR) binding sites: the leukocyte receptors Fc gamma RI and Fc gamma Rlla bind to a region in the Fc distinct from that recognized by neonatal FcR and protein a." J Immunol. May 15, 2000; 164(10):5313-8.
Wolff, M.E., Burger's Medicinal Chemistry, 4th Edition, Part I, Wiley: New York (1979) 336-337.
Wolff, M.E., Burger's Medicinal Chemistry, 5th Edition, Part I, John Wiley & Sons (1995) 975-977.
Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.
Wu et al., "Arming antibodies: prospects and challenges for immunoconjugates," (2005) Nature Biotech. 23(9):1137-1145.
Xie et al., "In vivo behaviour of antibody-drug conjugates for the targeted treatment of cancer," (2006) Expert. Opin Biol. Ther. 6(3):281-291.
Xie, G. et al., "Bisindolylmaleimides linked to DNA minor groove binding lexitropsins: synthesis, inhibitory activity against topoisomerasel, and biological evaluation," J. Med. Chem. (1996) 39:1049-1055.
Xu et al., "Molecular Cloning, Functional Characterization, Tissue Distribution, and Chromosomal Localization of a Human, Small Intestinal Sodium-Phosphate (Na +-Pi) Transporter (SLC34A2)," Genomics 62 (2):281-284 (1999).
Xu, M.J., et al., "Molecular Cloning and Characterization of SPAP1, an Inhibitory Receptor," (2001) Biochem. Biophys. Res. Commun. 280 (3):768-775.
Xu, X.Z., et al., "Regulation of melastatin, a TRP-related protein, through interaction with a cytoplasmic isoform," Proc. Natl. Acad. Sci. U.S.A. 98 (19):10692-10697 (2001).
Yamaguchi, N., et al., "A Novel Cytokine Exhibiting Megakaryocyte Potentiating Activity From a Human Pancreatic Tumor Cell Line HPC-Y5," Biol. Chem. 269 (2), 805-808 (1994).
Yamamoto T., et al., "Similarity of protein encoded by the human c-erb-B-2 gene to epidermal growth factor receptor," Nature 319, 230-234, 1986.

(56) References Cited

OTHER PUBLICATIONS

Yanagita et al., "Essential role of Gas6 for glomerular injury in nephrotoxic nephritis." J Clin Invest. Jul. 2002; 110(2):239-46.
Yang et al., "Murine Six-Transmembrane Epithelial Antigen of the Prostate, Prostate Stem Cell Antigen, and Prostate-specific Membrane Antigen: Prostate-specific Cell-Surface Antigens Highly Expressed in Prostate Cancer of Transgenic Adenocarcinoma Mouse Prostate Mice," Cancer Research, 61, 5857-5860. Aug. 1, 2001.
Yin & Lloyd, "Molecular Cloning of the CA125 Ovarian Cancer Antigen," J. Biol. Chem. 276 (29):27371-27375 (2001).
Yu et al., "Human mb-1 Gene: Complete eDNA Sequence and Its Expression in B Cells Bearing Membrane Ig of Various Isotypes," (1992) J. Immunol. 148(2) 633-637.
Zalevsky et al., "Enhanced antibody half-life improves in vivo activity." Nat Biotechnol. Feb. 2010; 28(2):157-9.
Zammarchi et al., "Pre-Clinical Development of Adct-402, a Novel Pyrrolobenzodiazepine (PBD)—Based Antibody Drug Conjugate (ADC) Targeting CD19-Expressing B-Cell Malignancies," Blood, 2015, 126:1564, Abstract.
Zhang et al., "AXL is a potential target for therapeutic intervention in breast cancer progression." Cancer Res. Mar. 15, 2008;68(6):1905-15.
Zhang et al., "Structural and functional analysis of the costimulatory receptor programmed death-1." Immunity. Mar. 2004; 20(3):337-47.

* cited by examiner

A. Human Axl

B. Cynomolgus monkey AXL

HUMANIZED ANTI-AXL ANTIBODIES

CROSS-REFERENCE TO RELATED APPLICATIONS

This application is a 35 U.S.C. § 371 National Stage Entry of International Application No. PCT/EP2016/058368 having an international filing date of Apr. 15, 2016, which claims the benefit of Great Britain Patent Application No. 1506411.6, filed Apr. 15, 2015, the contents of which are incorporated herein by reference in their entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 26,103 Byte ASCII (Text) file named "35710-251_SQL_ST25.TXT," created on Aug. 11, 2020. The present disclosure relates to humanized anti-Axl antibodies.

BACKGROUND

Axl

Axl is a member of the TAM (Tyro3-Axl-Mer) receptor tyrosine kinases (RTK) that share the vitamin K-dependent ligand Gas6 (growth arrest-specific 6). TAM family RTKs regulate a diverse range of cellular responses including cell survival, proliferation, autophagy, migration, angiogenesis, platelet aggregation, and natural killer cell differentiation. Axl is expressed in many embryonic tissues and is thought to be involved in mesenchymal and neural development, with expression in adult tissues largely restricted to smooth muscle cells (MGI Gene Expression Database; www.informatics.jax.org). Axl activation is linked to several signal transduction pathways, including Akt, MAP kinases, NE-KB, STAT, and others. Originally identified as a transforming gene from a patient with chronic myelogenous leukaemia, Axl has since been associated with various high-grade cancers and correlated with poor prognosis.

Axl receptor overexpression has been detected in a wide range of solid tumours and myeloid leukaemia (Linger et al, Adv Cancer Res. 100: 35, 2008; Linger et al, Expert Opin Ther Targets. 14:1073, 2010).

Axl expression correlates with malignant progression and is an independent predictor of poor patient overall survival in several malignancies including pancreatic (Song et al, Cancer. 117:734, 2011), prostate (Paccez et al, Oncogene. 32:698, 2013), lung (Ishikawa et al. Ann Surg Oncol. 2012; Zhang et al, Nat Genet. 44:852, 2012), breast (Gjerdrum, Proc natl Acad Sci USA 107:1124, 2010), colon cancer (Yuen et al, PLoS One, 8:e54211, 2013) and acute myeloid leukaemia (AML) (Ben-Batalla et al, Blood 122:2443, 2013).

Axl signal transduction is activated by a protein ligand (Gash) secreted by tumour associated macrophages (Loges et al, Blood. 115:2264, 2010) or autocrine mechanisms (Gjerdrum, Proc natl Acad Sci USA 107:1124, 2010), that drives receptor dimerization, autophosphorylation and downstream signalling, such as via PI3 kinase (PI3K)-AKT, particularly AKT and mitogen-activated protein kinase (MAPK) pathways (Korshunov, Clinical Science. 122:361, 2012). Heterodimerization with other tyrosine kinase receptors, e.g. epidermal growth factor receptor (EGFR), is also reported to occur (Linger et al, Expert Opin Ther Targets. 14:1073, 2010; Meyer et al Science Signalling 6:ra66, 2013).

Aberrant activation of Axl in tumour cells is widely associated with acquired drug resistance to targeted therapeutics in vitro and in vivo (Zhang et al. Nat Genet. 44: 852, 2012; Byers et al. Clin Cancer Res. 19: 279, 2013). Axl-targeting agents block tumour formation, metastasis and reverse drug resistance (e.g. to erlotinib) by reversing EMT/CSC characteristics in several experimental cancer models, including triple negative breast cancer, hormone resistant prostate cancer and adenocarcinoma of the lung (Holland et al Cancer Res 70:1544, 2010; Gjerdrum, Proc natl Acad Sci USA 107:1124, 2010; Zhang et al. Nat Genet. 44: 852, 2012; Paccez et al, Oncogene. 32:698, 2013).

Anti-Axl Antibodies

Applications relating to Axl and anti-Axl antibodies include EP2267454A2 [Diagnosis and prevention of cancer cell invasion measuring . . . Axl-Max Planck]; WO-2009063965 [anti Axl-Chugai Pharmaceutical]; WO2011-159980A1 [anti-Axl-Genentech], WO2011014457A1 [combination treatments Axl and VEGF antagonists-Genentech]; WO2012-175691A1 [Anti Axl 20G7-D9—INSERM], WO2012-175692A1 [Anti Axl 3E3E8—INSERM]; WO2009/062690A1 [anti Axl-U3 Pharma] and WO2010/130751A1 [humanised anti Axl-U3 Pharma].

GB1410826.0 discloses the murine anti-Axl antibody designated herein as "mouse 1H12". In view of the advantageous properties of this antibody and its potential clinical applications in humans, it is desirable to identify humanised versions of the murine antibody which have reduced immunogenicity to humans. The present disclosure concerns such antibodies, along with antibody-drug conjugates comprising the humanised 1H12 antibodies and PBD drug-moieties.

SUMMARY

The present disclosure provides humanized anti-AXL antibodies derived from the 'mouse 1H12' antibody.

The present inventors have generated a number of humanised heavy chain variable regions (SEQ ID NOs: 2 and 3) and humanised light chain variable regions (SEQ ID NOs:5 to 8) with a view to creating antibodies that have lower immunogenicity in a human individual than the 'mouse 1H12' antibody or 'chimeric 1H12' antibody whilst retaining antigen-binding potency. Surprisingly, these humanised antibodies have also been found to have other advantageous properties, such as increased charge at physiological pH and improved affinity for some Axl ligands.

Accordingly, in one aspect the present disclosure comprises an isolated humanized antibody that binds to AXL, wherein the isolated humanized antibody comprises a heavy chain variable region having the amino acid sequence of SEQ ID NO: 1, 2, or 3. In some embodiments the antibody further comprises a light chain variable region having the amino acid sequence of SEQ ID NO: 4, 5, 6, 7, or 8 and, optionally, further comprises a constant region derived from one or more human antibodies.

In some embodiments the isolated humanized antibody that binds to AXL comprises; a heavy chain variable region having the amino acid sequence of SEQ ID NO: 2 or 3; a light chain variable region having the amino acid sequence of SEQ ID NO: 5, 6, 7, or 8; and, optionally, comprises a constant region derived from one or more human antibodies.

In some embodiments, the humanized antibody does not comprise a heavy chain variable region having the amino acid sequence of SEQ ID NO: 1 and a light chain variable region having the amino acid sequence of SEQ ID NO: 4.

In some embodiments the isolated humanized antibody that binds to AXL comprises:

(i) a heavy chain variable region having the amino acid sequence of SEQ ID NO: 1 and a light chain variable region having the amino acid sequence of SEQ ID NO: 4;

(ii) a heavy chain variable region having the amino acid sequence of SEQ ID NO: 1 and a light chain variable region having the amino acid sequence of SEQ ID NO: 5;

(iii) a heavy chain variable region having the amino acid sequence of SEQ ID NO: 1 and a light chain variable region having the amino acid sequence of SEQ ID NO: 6;

(iv) a heavy chain variable region having the amino acid sequence of SEQ ID NO: 1 and a light chain variable region having the amino acid sequence of SEQ ID NO: 7;

(v) a heavy chain variable region having the amino acid sequence of SEQ ID NO: 1 and a light chain variable region having the amino acid sequence of SEQ ID NO: 8;

(vi) a heavy chain variable region having the amino acid sequence of SEQ ID NO: 2 and a light chain variable region having the amino acid sequence of SEQ ID NO: 4;

(vii) a heavy chain variable region having the amino acid sequence of SEQ ID NO: 2 and a light chain variable region having the amino acid sequence of SEQ ID NO: 5;

(viii) a heavy chain variable region having the amino acid sequence of SEQ ID NO: 2 and a light chain variable region having the amino acid sequence of SEQ ID NO: 6;

(ix) a heavy chain variable region having the amino acid sequence of SEQ ID NO: 2 and a light chain variable region having the amino acid sequence of SEQ ID NO: 7;

(x) a heavy chain variable region having the amino acid sequence of SEQ ID NO: 2 and a light chain variable region having the amino acid sequence of SEQ ID NO: 8;

(xi) a heavy chain variable region having the amino acid sequence of SEQ ID NO: 3 and a light chain variable region having the amino acid sequence of SEQ ID NO: 4;

(xii) a heavy chain variable region having the amino acid sequence of SEQ ID NO: 3 and a light chain variable region having the amino acid sequence of SEQ ID NO: 5;

(xiii) a heavy chain variable region having the amino acid sequence of SEQ ID NO: 3 and a light chain variable region having the amino acid sequence of SEQ ID NO: 6;

(xiv) a heavy chain variable region having the amino acid sequence of SEQ ID NO: 3 and a light chain variable region having the amino acid sequence of SEQ ID NO: 7; or (xv) a heavy chain variable region having the amino acid sequence of SEQ ID NO: 3 and a light chain variable region having the amino acid sequence of SEQ ID NO: 8.

In some embodiments AXL is human AXL.

The sequences of the antibody heavy chain variable regions and/or the light chain variable regions disclosed herein may be modified by, for example, insertions, substitutions and/or deletions to the extent that the humanized antibody maintains the ability to bind to AXL. The skilled person can ascertain the maintenance of this activity by performing the functional assays described herein, or known in the art.

Accordingly, in some embodiments the heavy chain variable region comprises no more than 20 insertions, substitutions and/or deletions, such as no more than 15, no more than 10, no more than 9, no more than 8, no more than 7, no more than 6, no more than 5, no more than 4, no more than 3, no more than 2, or no more than 1 insertion, substitution and/or deletion.

In some embodiments the light chain variable region comprises no more than 20 insertions, substitutions and/or deletions, such as no more than 15, no more than 10, no more than 9, no more than 8, no more than 7, no more than 6, no more than 5, no more than 4, no more than 3, no more than 2, or no more than 1 insertion, substitution and/or deletion.

In some embodiments the humanized antibodies of the disclosure include antibodies comprising $V_H$ and $V_L$ domains with amino acid sequences that are identical to the sequences described herein.

DETAILED DISCLOSURE

Antibody Properties
Antigen Binding

The antibody of the conjugates described herein is an antibody (Ab) which binds AXL. That is, the conjugates described herein are conjugates comprising antibodies which specifically bind to AXL.

As used herein, AXL refers to the Axl member of the TAM family of receptor tyrosine kinases. 'Human Axl' refers to the Axl member of the human TAM family of receptor tyrosine kinases. In some embodiments, the human Axl polypeptide corresponds to Genbank accession no. AAH32229, version no. AAH32229.1 GI:21619004, record update date: Mar. 6, 2012 01:18 PM (SEQ ID NO.9). In one embodiment, the nucleic acid encoding the human Axl polypeptide corresponds to Genbank accession no. M76125, version no. M76125.1 GI:292869, record update date: Jun. 23, 2010 08:53 AM. 'Murine Axl' refers to the Axl member of the murine TAM family of receptor tyrosine kinases. In some embodiments, the murine Axl polypeptide corresponds to Genbank accession no. AAH46618, version no. AAH46618.1 GI:55777082, record update date: Mar. 6, 2012 01:36 PM (SEQ ID NO.10). In one embodiment, the nucleic acid encoding the murine Axl polypeptide corresponds to Genbank accession no. NM_009465, version no. NM_009465.4 GI:300794836, record update date: Mar. 12, 2014 03:52 PM.

Antibody Affinity

In some embodiments the humanized antibody binds human AXL with a dissociation constant ($K_D$) of at least $10^{-6}$ M, such as at least $5 \times 10^{-7}$ M, at least $10^{-7}$ M, at least $5 \times 10^{-8}$ M, at least $10^{-9}$ M, such as at least $5 \times 10^{-10}$ M, at least $10^{-10}$ M, at least $5 \times 10^{-11}$ M, at least $10^{-11}$ M, at least $5 \times 10^{-12}$ M, at least $10^{-12}$ M, at least $5 \times 10^{-13}$ M, at least $10^{-13}$ M, at least $5 \times 10^{-14}$ M, at least $10^{-14}$ M, at least $5 \times 10^{-15}$ M, or at least $10^{-15}$ M.

In one embodiment the humanized antibody competitively inhibits the in vivo and/or in vitro binding to human AXL of an antibody comprising a heavy chain variable region having the amino acid sequence of SEQ ID NO: 1 and a light chain variable region having the amino acid sequence of SEQ ID NO: 4. In one embodiment the humanized antibody competitively inhibits the in vivo and/or in vitro binding to human-AXL of the 'mouse 1H12' antibody. In some embodiments an equimolar dose of the humanised antibody competitively inhibits at least 20% of the binding by the 'mouse 1H12' antibody, such as at least 30%, at least 40%, at least 50%, at least 60%, at least 70%, at least 80%, or at least 90% of the binding. Percentage binding may be measured by, for example, a competitive ELISA assay where % inhibition of binding is calculated as [(1−absorbance of test sample)/(absorbance of negative control)].

In some embodiments the humanized antibody has a higher affinity for an Axl antigen (for example the Axl-Strep-His antigen described in Protocol 4) than an antibody comprising a $V_H$ domain having the sequence according to SEQ ID NO. 1, a VL domain having the sequence according to SEQ ID NO. 4, and a constant region derived from one or more human antibodies (for example, Ab1 described herein). In some embodiments the KD of the humanized antibody with the Axl antigen (for example the Axl-Strep-His antigen described in Protocol 4) will be no more than 0.9 of the KD of the antibody comprising a VH domain having the sequence according to SEQ ID NO. 1, a VL domain having the sequence according to SEQ ID NO. 4, and a constant region derived from one or more human antibodies, for example no more than 0.8, 0.7, 0.6, 0.5, 0.4, 0.3, 0.2, 0.1, 0.05, 0.01, or 0.001 of the KD of the antibody comprising a VH domain having the sequence according to SEQ ID NO. 1, a VL domain having the sequence according to SEQ ID NO. 4, and a constant region derived from one or more human antibodies.

In some embodiments the humanized antibody has a higher affinity for an Axl antigen (for example the Axl-Fc antigen described in Protocol 4) than an antibody comprising a VH domain having the sequence according to SEQ ID NO. 1, a VL domain having the sequence according to SEQ ID NO. 4, and a constant region derived from one or more human antibodies (for example, Ab1 described herein). In some embodiments the KD of the humanized antibody with the Axl antigen (for example the Axl-Fc antigen described in Protocol 4) will be no more than 0.9 of the KD of the antibody comprising a VH domain having the sequence according to SEQ ID NO. 1, a VL domain having the sequence according to SEQ ID NO. 4, and a constant region derived from one or more human antibodies, for example no more than 0.8, 0.7, 0.6, 0.5, 0.4, 0.3, 0.2, 0.1, 0.05, 0.01, or 0.001 of the KD of the antibody comprising a VH domain having the sequence according to SEQ ID NO. 1, a VL domain having the sequence according to SEQ ID NO. 4, and a constant region derived from one or more human antibodies.

Antibody Isoelectric Point (pI)

A molecule carries no net charge when the pH of its surrounding equal the molecules pI. The net charge of a molecule affects the solubility of the molecule, with biological molecules such as proteins typically having minimum solubility in water or salt solutions at the pH that corresponds to their pI. Thus, proteins whose pI is 7.35-7.45 are at their minimum solubility in human blood, whose pH is typically in the range 7.35-7.45.

In some embodiments the humanized antibody of the disclosure has a pI greater than an antibody comprising a heavy chain variable region having the amino acid sequence of SEQ ID NO: 1 and a light chain variable region having the amino acid sequence of SEQ ID NO: 4. In some embodiments the humanized antibody of the disclosure has a pI greater than the mouse 1H12 antibody. In some embodiments the humanized antibody of the disclosure has a pI of at least 8.00, such as at least 8.05, at least 8.10, at least 8.15, at least 8.20, at least 8.30, at least 8.40, at least 8.50, at least 9, at least 9.5, at least 10, at least 10.5, or at least 11.

In some embodiments the humanized antibody of the disclosure has a pI less than an antibody comprising a heavy chain variable region having the amino acid sequence of SEQ ID NO: 1 and a light chain variable region having the amino acid sequence of SEQ ID NO: 4. In some embodiments the humanized antibody of the disclosure has a pI less than the mouse 1H12 antibody. In some embodiments the humanized antibody of the disclosure has a pI of no more than 7.0, such as no more than 6.5, no more than 6.0, no more than 5.5, no more than 5.0, no more than 4.5, or no more than 4.0.

Antibody Immunogenicity

Preferably the humanized antibody of the disclosure has reduced immunogenicity in a human subject as compared to a non-humanized antibody of the same specificity (for example, a mouse antibody precursor prior to humanization. In one embodiment the humanized antibody has immunogenicity in a human subject lower than an otherwise identical antibody or antibody fragment comprising a heavy chain variable region having the amino acid sequence of SEQ ID NO: 1 and a light chain variable region having the amino acid sequence of SEQ ID NO: 4. In one embodiment the humanized antibody has immunogenicity in a human subject lower than the 'mouse 11-112' antibody.

Low or reduced immunogenicity can be characterized by the ability to treat patients for extended periods with measurable alleviation of symptoms and low and/or acceptable toxicity. Low or acceptable immunogenicity and/or high affinity, as well as other suitable properties, can contribute to the therapeutic results achieved. "Reduced immunogenicity" is defined herein as raising significant HAHA, HACA or HAMA responses in less 90%, such as less than 80%, less than 70%, less than 60%, less than 50%, less than 40%, less than 30%, less than 20%, less than 10% of the proportion of patients who show a significant HAHA, HACA or HAMA response when treated with the mouse 1H12 antibody.

The disclosure also provided the means produce the antibodies of the disclosure.

Accordingly, in another aspect the disclosure provides nucleic acid molecules encoding the humanised antibodies, along with nucleic acid molecules complementary to nucleic acid molecules encoding the humanised antibodies.

In another aspect, the disclosure provides a pharmaceutical composition comprising an antibody pf the disclosure, optionally further comprising a pharmaceutically acceptable carrier or excipient.

In another aspect the disclosure provides a vector, such as an expression vector, comprising a nucleic acid of the disclosure.

In another aspect, the disclosure provides host cells transfected with a vector of the disclosure. The host cells may be prokaryotic or eukaryotic. For example, the cells may be bacterial, fungal, insect, or mammalian (such as mouse, primate or human).

In another aspect the disclosure provides a method of making the antibodies by culturing the host cells of the disclosure.

The disclosure provides methods relating to the identification of subjects particularly suitable for treatment with the antibodies or pharmaceutical composition of the disclosure. Also provided are methods for determining the optimum timing and dosage of administration of the antibodies of the disclosure to a subject. In some embodiments the subject has a proliferative disease, such as cancer. In some embodiments the subject has an autoimmune disease. Preferably, administration of the treatment inhibits or reduces one or more aspects of the disease, for example reduces tumour volume, or reduces the level of one or more biomarkers of tumour progression, such as AXL, Akt3, or GAS6. In some embodiments the level of the biomarker is reduced to no more than 90% of the level immediately before treatment, such as no more than 80%, no more than 70%, no more than 60%, no more than 50%, no more than 40%, no more than 30%, no more than 20%, no more than 10%, or no more than 5% of the level immediately before treatment.

In one aspect the disclosure provides a method of selecting a subject for treatment with the antibody or pharmaceutical composition of the disclosure, the method comprising assessing the level of one or more biomarkers associated with disease pathology, wherein subjects having the one or more biomarker, or subjects having a level of the one or more biomarkers which exceeds a threshold level, are selected for treatment. In some embodiments the biomarker is AXL, Akt3, or GAS6. In some embodiments the threshold is at least 10% higher than the upper boundary of the normal clinical range, such as at least 20% higher, at least 30% higher, at least 40% higher, at least 50% higher, at least 100% higher, or at least 200% higher.

In another aspect the disclosure provides a method of timing the administration of treatment of a subject with the antibody or pharmaceutical composition of the disclosure, the method comprising assessing the level of one or more biomarkers associated with disease pathology, wherein the treatment is administered when the subject has the one or more biomarker, or the subject has a level of one or more biomarkers which exceeds a threshold level. In some embodiments the biomarker is AXL, Akt3, or GAS6. In some embodiments the threshold is at least 10% higher than the upper boundary of the normal clinical range, such as at least 20% higher, at least 30% higher, at least 40% higher, at least 50% higher, at least 100% higher, or at least 200% higher.

In another aspect the disclosure provides a method of determining the optimum dosage of the antibody or pharmaceutical composition of the disclosure for administration to a subject, the method comprising assessing the level of one or more biomarkers associated with disease pathology, wherein subjects having the one or more biomarker, or subjects having a level of the one or more biomarkers which exceeds the threshold level, are selected for a particular dosage level. In some embodiments the biomarker is AXL, Akt3, or GAS6. In some embodiments the threshold is at least 10% higher than the upper boundary of the normal clinical range, such as at least 20% higher, at least 30% higher, at least 40% higher, at least 50% higher, at least 100% higher, or at least 200% higher.

In some embodiments the level of one or more biomarkers is assessed in a sample of blood, urine, other body fluid, or tissue. Level of one or more biomarkers samples can be assessed by immunoassay, proteomic assay, nucleic acid hybridization or amplification assays, immunohistochemistry, or in situ hybridization assays.

Definitions

Antibody

The term "antibody" as used encompasses any molecule comprising an antibody antigen-binding site (as, for example, formed by a paired VH domain and a VL domain). Thus, for example, the term "antibody" encompasses monoclonal antibodies (including intact monoclonal antibodies), polyclonal antibodies, multispecific antibodies formed from at least two different epitope binding fragments (e.g., bispecific antibodies), human antibodies, humanized antibodies, camelised antibodies, chimeric antibodies, single-chain antibodies (such as scFv fusions with CH3), antibody fragments that exhibit the desired biological activity (e.g. the antigen binding portion; for example minibodies), and anti-idiotypic (anti-Id) antibodies, intrabodies, and epitope-binding fragments of any of the above, so long as they exhibit the desired biological activity, for example, the ability to bind the cognate antigen. Antibodies may be murine, human, humanized, chimeric, or derived from other species. In one embodiment the antibody is a single-chain Fv antibody fused to a CH3 domain (scFv-CH3). In one embodiment the antibody is a single-chain Fv antibody fused to a Fc region (scFv-Fc). In one embodiment the antibody is a minibody.

An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes an intact immunoglobulin molecule or an immunologically active portion of a intact immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease.

In particular, antibodies include immunoglobulin molecules and immunologically active fragments of immunoglobulin molecules, i.e., molecules that contain at least one antigen binding site. The antibody can be of any isotype (e.g. IgG, IgE, IgM, IgD, and IgA), class (e.g. IgG1, IgG2, IgG3, IgG4, IgA1 and IgA2) or subclass, or allotype (e.g. human G1m1, G1m2, G1m3, non-G1m1 [that, is any allotype other than G1m1], G1m17, G2m23, G3m21, G3m28, G3m11, G3m5, G3m13, G3m14, G3m10, G3m15, G3m16, G3m6, G3m24, G3m26, G3m27, A2m1, A2m2, Km1, Km2 and Km3) of antibody molecule. The immunoglobulins can be derived from any species, including human, murine, or rabbit origin.

An "intact antibody" herein is one comprising VL and $V_H$ domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

In preferred embodiments the antibody is an intact IgG antibody. That is an antibody comprising two light chains, each having a variable and constant domain, and two heavy chains, each having one variable domain and three constant domains.

Humanized

As used herein "humanized" antibodies include any combination of the herein described Anti-AXL antibodies. In these antibodies the mouse framework residues from the murine 1H12 antibody have been largely replaced with the corresponding residues from human immunoglobulins. As many of the human amino acid residues as possible are retained, but critical human residues may be modified as necessary to support the antigen binding site formed by the CDRs and recapitulate the antigen binding potency of the original mouse antibody. Such changes or variations optionally and preferably retain or reduce the immunogenicity in humans or other primate species relative to non-modified antibodies.

It is pointed out that a humanized antibody can be produced by a non-human animal or prokaryotic or eukaryotic cell that is capable of expressing functionally rearranged human immunoglobulin (e.g., heavy chain and/or light chain) genes. Further, when the antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

For example, in some embodiments the humanised antibody of the disclosure are produced by a method comprising the step of grafting the CDRs of the mouse 1H12 antibody into human FW regions such as AB021508, AB063892, AF233253, and AJ399878. In some embodiments the method of producing the humanised antibodies of the invention further comprises the step of back-mutating mismatches at vernier and 5A CDR envelope residues. In other embodiments the method of producing the humanised antibodies of the invention further comprises the step of back-mutating mismatched vernier residues only.

The human constant region of the humanized antibody can be of any class (IgG, IgA, IgM, IgE, IgD, etc.) or isotype and can comprise a kappa or lambda light chain. In one embodiment, the human constant region comprises an IgG heavy chain or defined fragment, for example, at least one of isotypes, IgG1, IgG2, IgG3 or IgG4. In another embodiment, the humanized antibody comprises an IgG1 heavy chain and a IgG1 K light chain. The isolated humanized antibodies described herein comprise antibody amino acid sequences disclosed herein encoded by any suitable polynucleotide.

Sequence Modifications

The sequences of the antibody heavy chain variable regions and/or the light chain variable regions disclosed herein may be modified by substitution, insertion or deletion. Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Preferred conservative substitutions are those wherein one amino acid is substituted for another within the groups of amino acids indicated herein below:

Amino acids having polar side chains (Asp, Glu, Lys, Arg, His, Asn, Gin, Ser, Thr, Tyr, and Cys)
Amino acids having non-polar side chains (Gly, Ala, Val, Leu, Ile, Phe, Trp, Pro, and Met)
Amino acids having aliphatic side chains (Gly, Ala Val, Leu, Ile)
Amino acids having cyclic side chains (Phe, Tyr, Trp, His, Pro)
Amino acids having aromatic side chains (Phe, Tyr, Trp)
Amino acids having acidic side chains (Asp, Glu)
Amino acids having basic side chains (Lys, Arg, His)
Amino acids having amide side chains (Asn, Gin)
Amino acids having hydroxy side chains (Ser, Thr)
Amino acids having sulphur-containing side chains (Cys, Met),
Neutral, weakly hydrophobic amino acids (Pro, Ala, Gly, Ser, Thr)
Hydrophilic, acidic amino acids (Gin, Asn, Glu, Asp), and
Hydrophobic amino acids (Leu, Ile, Val)

Particular preferred conservative amino acids substitution groups are: Val-Leu-Ile, Phe-Tyr, Lys-Arg, Ala-Val, and Asn-Gln.

In some embodiments, the antibody of the conjugates described herein comprises a heavy chain having an amino acid sequence with 80% or more amino acid sequence identity (for example, about 85% or more, 86% or more, 87% or more, 88% or more, 89% or more, 90% or more, 91% or more, 92% or more, 93% or more, 94% or more, 95% or more, 96% or more, 97% or more, 98% or more, 99% or more sequence identity) to a heavy chain described herein. In some embodiments, the antibody of the conjugates described herein comprises a light chain having an amino acid sequence with 80% or more amino acid sequence identity (for example, about 85% or more, 86% or more, 87% or more, 88% or more, 89% or more, 90% or more, 91% or more, 92% or more, 93% or more, 94% or more, 95% or more, 96% or more, 97% or more, 98% or more, 99% or more sequence identity) to a light chain described herein.

In some embodiments, the antibody of the conjugates described herein comprises a heavy chain having an amino acid sequence identical to the amino acid sequence of a heavy chain described herein, except that it includes 1, 2, 3, 4, 5, 6, 7, 8, 9 or 10 amino acid modifications (e.g., substitutions, insertions and/or deletions) relative to the amino acid sequence of the heavy chain described herein. In some embodiments, the antibody of the conjugates described herein comprises a light chain having an amino acid sequence identical to the amino acid sequence of a light chain described herein, except that it includes 1, 2, 3, 4, 5, 6, 7, 8, 9 or 10 amino acid modifications (e.g., substitutions, insertions and/or deletions) relative to the amino acid sequence of the light chain described herein.

Antibody Production

Humanized antibodies, fragments and regions can be produced by cloning DNA segments encoding the H and L chain antigen-binding regions of the anti-AXL antibody, and joining these DNA segments to DNA segments including CH and CL regions, respectively, to produce full length immunoglobulin-encoding genes.

For full-length antibody molecules, the immunoglobulin cDNAs can be obtained from mRNA of hybridoma cell lines. Antibody heavy and light chains are cloned in a mammalian expression vector system. Assembly is documented with DNA sequence analysis. The antibody construct can be expressed in human or other mammalian host cell lines. The construct can be validated by transient transfection assays and immunoassay of the expressed antibody. Stable cell lines with the highest productivity can be isolated and screened using rapid assay methods.

Biological Activity

In Vitro Cell Proliferation Assays

Generally, the cytotoxic or cytostatic activity of an antibody is measured by: exposing mammalian cells having receptor proteins to the antibody in a cell culture medium; culturing the cells for a period from about 6 hours to about 5 to 7 days; and measuring cell viability. Cell-based in vitro assays are used to measure viability (proliferation), cytotoxicity, and induction of apoptosis (caspase activation) of an antibody of the disclosure.

The in vitro potency of antibodies can be measured by a cell proliferation assay. The CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713 and 5,700,670). This cell proliferation assay determines the number of viable cells in culture based on quantitation of the ATP present, an indicator of metabolically active cells (Crouch et al (1993) *J. Immunol. Meth.* 160:81-88; U.S. Pat. No. 6,602,677). The CellTiter-Glo® Assay is conducted in 96 well format, making it amenable to automated high-throughput screening (HTS) (Cree et al (1995) *AntiCancer Drugs* 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with antibody, or they may be treated and separated from antibody. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

The in vitro potency of antibody-drug conjugates can also be measured by a cytotoxicity assay. Cultured adherent cells are washed with PBS, detached with trypsin, diluted in complete medium, containing 10% FCS, centrifuged, re-suspended in fresh medium and counted with a haemocytometer. Suspension cultures are counted directly. Monodisperse cell suspensions suitable for counting may require agitation of the suspension by repeated aspiration to break up cell clumps.

The cell suspension is diluted to the desired seeding density and dispensed (100 pl per well) into black 96 well plates. Plates of adherent cell lines are incubated overnight to allow adherence. Suspension cell cultures can be used on the day of seeding.

A stock solution (1 ml) of antibody (20 µg/ml) is made in the appropriate cell culture medium. Serial 10-fold dilutions of stock antibody are made in 15 ml centrifuge tubes by serially transferring 100 µl to 900 µl of cell culture medium.

Four replicate wells of each antibody dilution (100 µl) are dispensed in 96-well black plates, previously plated with cell suspension (100 µl), resulting in a final volume of 200 µl. Control wells receive cell culture medium (100 µl).

If the doubling time of the cell line is greater than 30 hours, antibody incubation is for 5 days, otherwise a four day incubation is done.

At the end of the incubation period, cell viability is assessed with the Alamar blue assay. AlamarBlue (Invitrogen) is dispensed over the whole plate (20 µl per well) and incubated for 4 hours. Alamar blue fluorescence is measured at excitation 570 nm, emission 585 nm on the Varioskan flash plate reader. Percentage cell survival is calculated from the mean fluorescence in the antibody treated wells compared to the mean fluorescence in the control wells.

Use

The antibody of the disclosure may be used to target a target location.

The target location is preferably a proliferative cell population. The antibody is an antibody for an antigen present on a proliferative cell population.

In one embodiment the antigen is absent or present at a reduced level in a non-proliferative cell population compared to the amount of antigen present in the proliferative cell population, for example a tumour cell population.

The target location may be in vitro, in vivo or ex vivo.

The antibodies of the disclosure include those with utility for anticancer activity. Thus, in one aspect, the present disclosure provides an antibody as described herein for use in therapy.

In a further aspect there is also provides an antibody as described herein for use in the treatment of a proliferative disease. A second aspect of the present disclosure provides the use of an antibody in the manufacture of a medicament for treating a proliferative disease.

One of ordinary skill in the art is readily able to determine whether or not a candidate conjugate treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), lymphomas, leukemias, psoriasis, bone diseases, fibroproliferative disorders (e.g. of connective tissues), and atherosclerosis. Cancers of particular interest include, but are not limited to, metastatic cancer cells, such as circulating tumour cells, which may be found circulating in body fluids such as blood or lymph, lymphomas (e.g., non-Hodgkin's lymphoma, NHL), leukemia (particularly acute myeloid leukemia, AML) and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

It is contemplated that the antibody of the present disclosure may be used to treat various diseases or disorders, e.g. characterized by the overexpression of a tumour antigen. Exemplary conditions or hyperproliferative disorders include benign or malignant tumours; leukemias, haematological, and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemias or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the antibody may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Methods of Treatment

The antibody of the present disclosure may be used in a method of therapy. Also provided is a method of treatment, comprising administering to a subject in need of treatment a therapeutically-effective amount of an antibody of the disclosure. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

An antibody may be administered alone or in combination with other treatments, either simultaneously or sequentially dependent upon the condition to be treated. Examples of treatments and therapies include, but are not limited to, chemotherapy (the administration of active agents, including, e.g. drugs, such as chemotherapeutics); surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7, 9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gamma1I, calicheamicin omega1I (*Angew Chem. Intl. Ed. Engl*. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenishes such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumours such as anti-estrogens and selective estrogen receptor modulators (SERMs), including, for example, tamoxifen (including NOLVADEX®; tamoxifen citrate), raloxifene, droloxifene, 4-hydrmtamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; Astra-Zeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), ofatumumab (ARZERRA®, GSK), pertuzumab (PERJETA™, OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the conjugates of the disclosure include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Pharmaceutical compositions according to the present disclosure, and for use in accordance with the present disclosure, may comprise, in addition to the active ingredient, i.e. an antibody, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Formulations

While it is possible for the antibody to be used (e.g., administered) alone, it is often preferable to present it as a composition or formulation.

In one embodiment, the composition is a pharmaceutical composition (e.g., formulation, preparation, medicament) comprising an antibody, as described herein, and a pharmaceutically acceptable carrier, diluent, or excipient.

In one embodiment, the composition is a pharmaceutical composition comprising at least one antibody, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives*, 2nd Edition (eds. M. Ash and I. Ash), 2001 (Synapse Information Resources, Inc., Endicott, New York, USA), *Remington's Pharmaceutical Sciences*, 20th edition, pub. Lippincott, Williams & Wilkins, 2000; and *Handbook of Pharmaceutical Excipients*, 2nd edition, 1994.

Another aspect of the present disclosure pertains to methods of making a pharmaceutical composition comprising admixing at least one [$^{11}$C]-radiolabelled antibody or antibody-like molecule, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the antibody, and compositions comprising the antibody, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the antibody is in the range of about 100 ng to about 25 mg (more typically about 1 μg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the antibody is administered to a human patient according to the following dosage regime: about 100 mg, 3 times daily.

In one embodiment, the antibody is administered to a human patient according to the following dosage regime: about 150 mg, 2 times daily.

In one embodiment, the antibody is administered to a human patient according to the following dosage regime: about 200 mg, 2 times daily.

However in one embodiment, the antibody is administered to a human patient according to the following dosage regime: about 50 or about 75 mg, 3 or 4 times daily.

In one embodiment, the antibody is administered to a human patient according to the following dosage regime: about 100 or about 125 mg, 2 times daily.

For the prevention or treatment of disease, the appropriate dosage of an antibody of the disclosure will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of antibody to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of an antibody. Other dosage regimens may be useful. The progress of this therapy is easily monitored by conventional techniques and assays.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an antibody, or a material, composition or dosage from comprising an antibody, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an antibody, or a material, composition or dosage from comprising an antibody, which is effective for producing some desired prophylactic effect, commensurate with a reasonable benefit/risk ratio, when administered in accordance with a desired treatment regimen.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

MATERIALS AND METHODS

Figure 1:
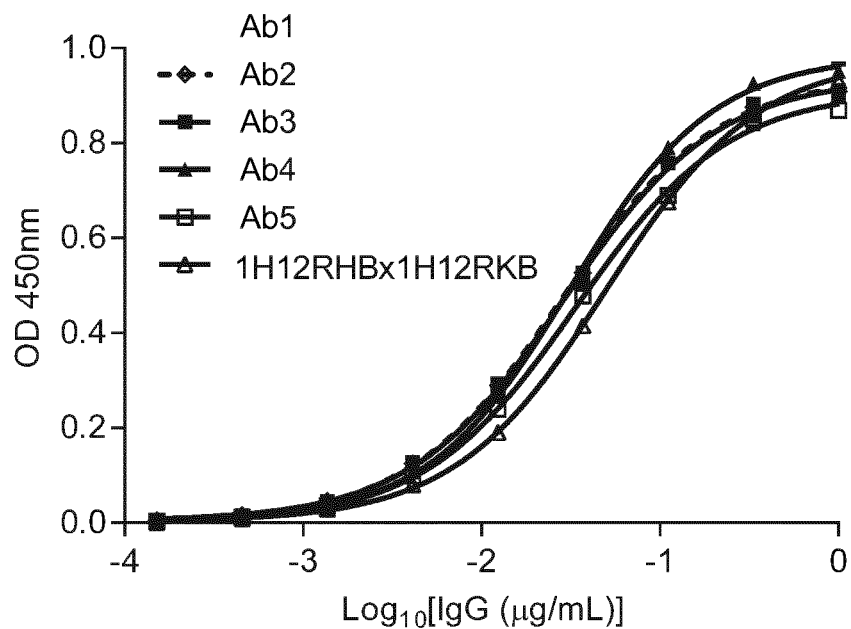
FIG. 1: AXL binding ELISA of fully humanised constructs. (2A) to Human AXL. (2B) to Cynomolgus monkey AXL.
Figure 1:
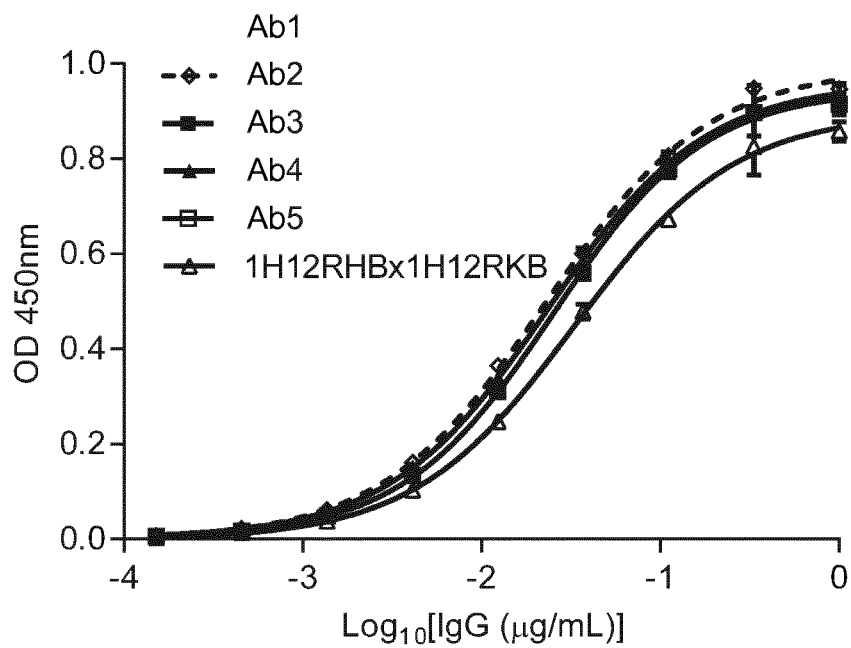

Protocol 1: Production of DNA Plasmids for Expression
Materials
For heavy chain construct selection, Zeocin 25 µg/ml (Invivogen) was used.
For light chain construct selection, Blasticidin 100 µg/ml (Life Technologies) was used.
Method
Transformed bacteria were spread on LB-agar Zeocin/Blasticidin plates, as required, incubated overnight at 37 C, then colonies were picked from each plate.
VH or VK colonies/glycerol stocks were inoculated into 3 ml LB containing Zeocin 25 µg/ml or Blasticidin 50 µg/ml, respectively.
p21, p27, pAdvantage (Promega) and pSVLT (generous gift from Tom Vink) were inoculated in LB-Ampicillin and shaken overnight.
3 ml overnight colony was seeded into 200 ml of LB-antibiotic and shaken overnight.
DNA plasmids were isolated from each culture using the Promega PureYield™ Plasmid Maxiprep Kit following the manufacturer's instructions.

Protocol 2. Transient Transfection of HEK293T Cells with Expression Constructs Materials
Cells: HEK293T cells
Culture medium: DMEM high glucose 4.5 g/L (PAA) with 10% v/v FCS, penicillin and streptomycin
Fugene HD transfection reagent (Promega #E2311)
Opti-MEM (Life Technologies #11058-021) or
FreeStyle 293 Expression Medium (Life Technologies #12338-018)
Method
Grow HEK293T cells in a T75 or T175 flask in a $CO_2$-gassed cell culture incubator. Split cultures 1:3 every 2 days or 1:4 to 1:5 every 3-4 days. The cells adhere weakly to the flasks and only a light trypsinisation is necessary to detach cells during passaging.

The Day Before Transfection:
1. Trypsinise the cells, wash 1× in DMEM/10% FCS and count the cells.
2. Seed cells in a 6 well plate in 2 ml per well containing $2×10^5$ cells.

Next day, check cells are at least 80% confluent and replace the medium (2 ml/well).
1. 1.2 µg of total DNA (0.6 ug of each high and light chain DNA) is needed for each transfection and better results are obtained if the DNA concentration is at or above 90 ng/µl.
2. Add 0.6 ug of VH and 0.6 ug VK expression plasmid DNAs into of Fugene HD (4.5 µl) and OptiMEM/Freestyle medium, in a total volume of 60 ul, avoiding touching the sides of the tube with the Fugene HD.
3. Mix and leave at RT for 15 minutes.
4. Add Fugene mixture drop-wise around the well of HEK293T cells.
5. Return the 6-well plate to the $CO_2$-gassed cell culture incubator for 4 days.
6. Harvest each conditioned medium, centrifuge, and store at 4° C.

Protocol 3: IgG Quantitation by ELISA
Materials
Nunc-Immuno Plate MaxiSorp (Life Technologies, 43945A)
Goat Anti-Human IgG(Fc)-AffiniPure: Stratech Scientific, 109-005-098-JIR; 1 mg:
1.3 mg/ml
Human IgG1/kappa antibody (Sigma, 1-3889-1 mg: 1 mg/ml)
Goat anti-human kappa light chain peroxidase conjugate (Sigma, A-7164-1 ml)
1-Step Turbo TMB-ELISA, 250 mL (Thermo Scientific: #34022)
Acid stop=0.1M HCL
Sample enzyme conjugate (SEC) buffer Tween 20 (0.02% v/v), BSA 0.2% (w/v) in PBS
Washing buffer: 1×PBS, Tween 20 (0.1% v/v)
Method
1. Coat each well of a 96-well immunoplate with 100 pl aliquots of 0.4 µg/ml (dilute stock×3000=10 ul in 30 ml: coat 5 ml per plate) goat anti-human IgG antibody, diluted in PBS, incubate overnight at 4° C. (or 37 C 1 hr). (Plates may be stored for 1 month at this stage). Also coat another blank plate with BSA/PBS blocking solution.
2. wash plate 3× with 200 µl/well of washing buffer.
3. Block coated plate: add 200 ul 3% BSA in PBS: incubate 37 C 1 hr
4. Into blank plate, dispense 200 µl SEC buffer into all wells except row B, cols 2-11 (blue, below).
5. Prepare 1 ug/ml solution of the human IgG1/kappa antibody in SEC buffer (×1000 diln)

Blocked Uncoated Plate:
6. Pipette 50 µl/well of stds/unknowns into rows A-H, cols 1 and 7 (makes a ×5 dilution).
7. Serially transfer 100 µl across plate to achieve serial ×3 dilution series.
8. Transfer 100 µl from each well to the corresponding well of the BLOCKED anti-IgG-COATED plate.

Blocked Anti-IgG Coated Plate:
9. Incubate at 37° C. for 1 hr. Rinse all the wells 3× with washing buffer (200 µl).
10. Dilute the goat anti-human kappa light chain peroxidase conjugate 5000-fold in SEC buffer and add 100 µl to each well. Repeat the incubation and washing steps (step 9).
11. Add 100 µl of TMB Turbo substrate to each well, incubate in the dark at room temperature for 10 min.
12. Stop the reaction by adding 50 µl of acid (0.1M HCl) to each well.
13. Read the optical density at 450 nm.

Protocol 4: AXL Binding ELISA
Materials
Human AXL-Strep-His was produced by Evitria AG in transiently transfected CHO cells and purified on Ni Sepharose High Performance (GE Healthcare 17-5268-01) following manufacturers instructions and stored in aliquots at −20 C.
Goat anti-human kappa light chain peroxidase conjugate (Sigma, A-7164-1 ml)
Nunc-Immuno Plate MaxiSorp (Life Technologies, 43945A)
Plate washer: Biotek LS405
3% BSA: BSA 3% w/v in PBS
PBS Tween: Tween 20 0.05% v/v in PBS
PBS/Tween/BSA: BSA 0.5% w/v in PBS/Tween
1-Step Turbo TMB-ELISA (Thermo Scientific #3402)
Protocol
1. Dispense 50 µl/well of human AXL-strep-His (1 ug/ml in PBS)
2. Cover with adhesive plate sealer and incubate at 4 C overnight.
3. Block: Dispense 50 µl/well of 3% BSA and incubate for 1 hr 37 C,
4. Wash plate with PBS/Tween 3×
5. Serially 3-fold dilute 5E5 antibodies (2 ml HEK293T culture supernatants) on non-binding polypropylene plate in PBS/Tween/BSA: serially transfer 50 ul onto 100 ul.
6. Transfer 50 ul from antibody dilution plate onto washed, blocked AXL-coated plate

|   | 1 | 2 | 3 | 4 | 5 | 6 | 7 | 8 | 9 | 10 | 11 | 12 |
|---|---|---|---|---|---|---|---|---|---|----|----|----|
| A | STD | | | | | | unk4 | | | | | |
| B | STD | | | | | | unk4 | | | | | |
| C | unk1 | | | | | | unk5 | | | | | |
| D | unk1 | | | | | | unk5 | | | | | |
| E | unk2 | | | | | | unk6 | | | | | |
| F | unk2 | | | | | | unk6 | | | | | |
| G | unk3 | | | | | | unk7 | | | | | |
| H | unk3 | | | | | | unk7 | | | | | |

200 µl diluent in every well

+50 µl sample Transfer 100 µl →    +50 µl sample Transfer 100 µl →

200  66.67  22.22  7.41  2.47  0.82    200  66.67  22.22  7.41  2.47  0.82  ng/ml

Stock std = 1 µg/ml

7. Incubate 37 C 1 hr
8. Wash plate with PBS/Tween 3×
9. Dispense anti-human IgG-HRP conjugate, diluted 1:1000 in PBS/Tween/BSA
10. Incubate 37 C 1 hr
11. Wash plate with PBS/Tween 3
12. Wash plate with PBS 3×
13. Dispense 100 ul/well 1-Step Turbo TMB-ELISA substrate solution
14. Incubate 30 min at room temperature (or less if reaction is rapid)
15. Dispense 100 ul/well 0.6M HCl to stop the substrate reaction
16. Measure optical density at 450 nm Protocol 4A: SPR Measurement of Antibody Affinity
Materials
1. Sensor Chip CM5 Biacore; Cat. #BR-1000-14
2. Amine Coupling Kit (EDC, NHS, ethanolamine-HCl) Biacore; Cat. #BR-1000-50
3. Immobilization buffer (10 mM Na acetate, pH 4.0) Biacore; Cat. #BR-1003-49
4. 50 mM NaOH Biacore; Cat. #BR-1003-58
5. Running buffer (PBS/Tween20 0.05% v/v)
6. Biacore T200 GE Healthcare
7. Regeneration solution: 10 mM HCl, 1 M NaCl Coupling Method
Activate flow cell 2 with NHS-EDC 420s at 5 µl/min, then inject human Axl-Strep-His (Evitria) (10 µg/mL in 10 mM sodium acetate, pH 4.0) to achieve a coupling of 10-20 RU. Block with ethanolamine for 420s. Repeat the process for flow cell 1 but with no antigen to create a reference flow cell. 12RU AXL fusion protein was coated.

For the Fc fusion, Human Axl-Fc chimera (R&D Systems #154-AL) (5 µg/mL in 10 mM sodium acetate, pH 4.5) was used with the above protocol. 16RU of AXL-Fc was coated.

Protocol with AXL-Strep-His Antigen
Serial 10× dilutions of antibody, from 3000 nM, were made in PBS/Tween20. 2× regeneration cycles were used with 10 mM HCl, 1 M NaCl for 30s at 30 µl/min for both cycles. Start-up solution was PBS/Tween20 and set to 3 cycles.
Sample injection parameters were 120s at 30 µl/min, with 600s dissociation time.
Prime and normalise detector were run before sample application with experimental conditions 25 C and sample storage at 4 C.
Kinetic analysis used BIAevaluation software with bivalent ligand binding model. For chimeric 1H12 with AXL-Strep-His, "heterogeneous ligand" binding model was used due to poor fit with bivalent or monovalent algorithms.
Each antibody dilution was injected twice.

Protocol with AXL-Fc Chimera Antigen
The above protocol was used except that the running buffer was HBSEP+, serial 10× dilutions of antibody were from 500 nM in HBSEP+ running buffer and were injected for 180 sec.
Analysis used BIAevaluation software with the bivalent binding model.

Protocol 5: Capillary Isoelectric Focusing
Materials
PA 800 plus (AB SCIEX)
Anolyte Solution: 200 mM Phosphoric Acid (Sigma-Aldrich #345 245).
4.3M Urea (Sigma-Aldrich #U0631) in water.
Catholyte Solution: 300 mM Sodium Hydroxide.
3M Urea (Sigma-Aldrich #U0631) in cIEF Gel (Beckman Coulter #477497).
Chemical Mobiliser: 350 mM Acetic Acid (Sigma-Aldrich #537 020).
Pharmalyte 3-10 (GE Healthcare 17-0456-01).
Cathodic Stabiliser: 500 mM Arginine (Sigma-Aldrich #A5006).
cIEF Peptide markers PI 4-10 (Beckman Coulter #A58481).
Anodic Stabiliser: 200 mM Iminodiacetic Acid (Sigma-Aldrich #220 000).
Neutral Capillary, 50 µm i.d.×45 cm, (Beckman Coulter #477 441)

Figure 3:
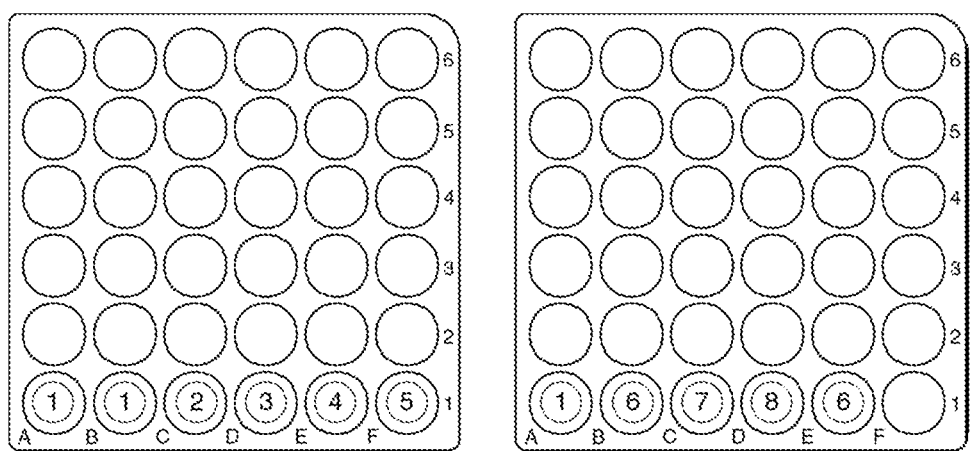
FIG. 3 is a schematic diagram of buffer trays containing reagents as described in Protocol 5.

Method
Turn on the PA800+ machine and UV lamp, allowing it to warm up 30 mins before use.
Clean the system electrodes and interface block with a damp Kimwipe.
Prepare buffer trays as shown in FIG. 3, with 1.5 mL reagent per vial, 1 mL of water in the waste and place in the system.
1. DDI water
2. Anolyte
3. Urea Solution
4. 3M urea/cIEF Gel
5. Chemical Mobilizer
6. Waste
7. Catholyte
8. Chemical Mobilizer
9. BI (Inlet Buffer Tray)
10. BO (Outlet Buffer Tray)
NOTE. Each set of buffer vials is good for 6 consecutive runs or for 24 hours inside the instrument.
Insert the capillary cartridge into the system and close the front panel.
NOTE. Do not expose the neutral-coated capillary ends to air for more than fifteen min. When the capillary is not in use, submerge the capillary ends in vials filled with DDI water.
Prepare cIEF master mix using the table below. Dispense each reagent into a centrifuge tube, vortex 1 min, invert every 15-20 sec to ensure complete mixing and store at 2° C. to 8° C. for up to 1 day.

| Reagent | Volume per sample (µl) |
| --- | --- |
| 3M Urea-cIEF Gel | 100 |
| Pharmalyte 3-10 | 12 |
| Cathodic Stabiliser | 20 |
| Anodic Stabiliser | 2 |
| pI marker 10 | 2 |
| pI marker 9.5 | 2 |
| pI marker 7 | 2 |
| pI marker 5.5 | 2 |
| pI marker 4.1 | 2 |

Desalt and concentrate each antibody (to about 5 mg/ml) in 2M urea using Amicon Ultra 0.5 mL centrifugal filters (Sigma Z677108).
Mix 200 µL of master mix with 10 µL of protein, vortex the cIEF sample for 1 min, inverting the tube every 15-20 sec, then centrifuge at high speed to remove any air bubbles. Transfer 100 µL of sample into a micro vial. Place the micro vial into a universal plastic vial and cap it with a blue cap. Then place the sample vial in the inlet sample tray.

Figure 2:
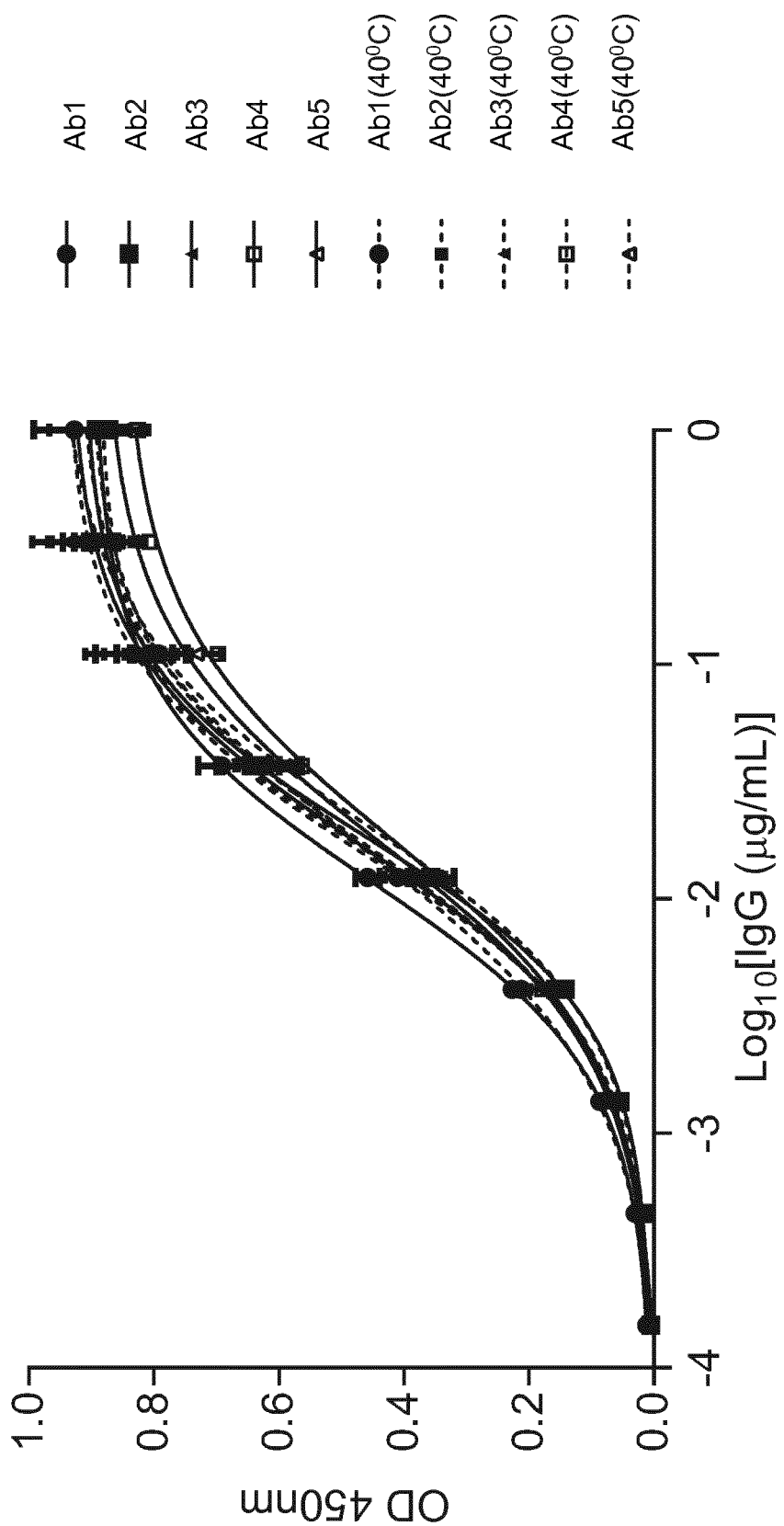
FIG. 2: Accelerated stability analysis

Run the "cIEF Conditioning—PA 800 plus.met" method to condition the column.
  Rinse for 5 min at 50 psi with Chemical Mobilizer. See FIG. 2.10.
  2 Rinse for 2 min at 50 psi with DDI water.
  3 Rinse for 5 min at 50 psi with cIEF gel.
  4 Submerge both of the capillary ends in vials filled with DDI water.
Use the "cIEF Separation-PA 800 plus.met" method to create a sequence containing all protein samples and a blank.
  Rinse for 3 min at 50 psi with Urea Solution. See FIG. 2.11.
  Rinse for 2 min at 50 psi with DDI water.
  Inject sample for 99.0 sec at 25 psi.
  Water dip by submerging both capillary ends in DDI water.
  Focusing step, 15 min at 25 kV under normal polarity (Time=0).
  Chemical mobilization, 30 min at 30 kV under normal polarity (Time=15 min).
  Stop data collection (Time=45 min).
  Rinse for 2 min at 50 psi with DDI water (Time=45.10 min).
  Submerged both of the capillary ends in DDI water (Time=47.20 min).
  End the method (Time=47.30 min).
Put the "cIEF Shutdown—PA 800 plus.met" method at the end of the sequence to rinse the capillary and turn off the UV.
  Rinse for 2 min at 50 psi with DDI water. See FIG. 2.12.
  Rinse for 5 min at 50 psi with cIEF gel.
  Turn off the UV lamp.
  Submerge both of the capillary ends in vials filled with DDI water.
  For short term storage (1 to 3 days), leave the capillary on the instrument. For long term storage (over 3 days), place the capillary cartridge in the storage box with both ends submerged in water tubes and store upright at 4 C.

Protocol 6: Protein Thermal Shift Protocol
Materials
96 well optical plate semi-skirted (Starlab cat.L1402-9700).
Protein thermal shift dye kit (Life Technologies cat.446148).
Microamp optical adhesive film (Applied Biosystems)
7500 Real-Time PCR System (Life Technologies)
Test items: Antibodies from Evitria and Spirogen
Protein thermal shift v1.2 software (Life Technologies)
Method
Protein thermal shift dye (2.5 µL 1:1000 dilution) was added to sample proteins (17.5 µL of 0.5 mg/mL in PBS) in a 96 well optical plate and mixed thoroughly. Every sample was done in quadruplicate. The plate was sealed with a optical adhesive film and bubbles in the wells were removed by centrifugation 1 min at 500 g, then placed on ice. The sealed plate was introduced in the 7500 Real-Time PCR System and subsequently the experiment was set up as follows:

| Experiment Name | Name (using up to 100 letters/numbers) |
| --- | --- |
| Instrument type | 7500 Fast (96 Wells) or 7500 (96 Wells) |
| Experiment type | Melt Curve |

-continued

| Reagent type | Other |
| --- | --- |
| Ramp speed | Standard |
| Reporter | ROX |
| Quencher | None |
| Passive Reference | None |

Temperature cycling on the ABI 7500 set up:

| Reaction vol | 20 µl | | |
| --- | --- | --- | --- |
| Ramp mode | continuous | | |
| Step | Ramp rate | Temp ° C. | Time (mm:ss) |
| 1 | 100% | 25.0 | 02:00 |
| 2 | 1% | 99.0 | 02:00 |

Data analysis and derivation of Tm data were done using the software following the manufacturers instructions.

Protocol 7: HPLC Size Exclusion Chromatography
Materials
Shimadzu HPLC system, or equivalent, consisting of the following, or equivalent:
  2×DGU-20A$_{5R}$ Prominence Degassing units
  2× LC-20AD$_{XR}$ Nexera Pumps
  SIL-20AC$_{XR}$ Nexera Autosampler
  CTO-20AC Prominence Column oven
  SPD-M30A Prominence DAD detector
  Computer with LabSolutions software.
  TSKgel Super SW mAb HTP 4 um 4.6 mm×15 cm
  200 mM Potassium Phosphate, 250 mM Potassium Chloride, 10% v/v i-Propanol, pH 6.95.
Sample Preparation
Mobile Phase: 200 mM Potassium Phosphate, 250 mM Potassium Chloride, 10% v/v i-Propanol, pH 6.95.
Analytical Sample: Inject 2-20 µL of neat ADC sample (at least 1 mg/ml for best results). Typically 10 µL of 5 mg/ml gives good results.
HPLC Parameters
Method File name: MSOP-018
HPLC Column: TSKgel Super SW mAb HTP 4 urn 4.6 mm×15 cm
Flow Rate: 0.5 ml/min
Injection volume: 2-20 µL
Detection, UV: 280 nm
330 nm (for information only)
Column Temp: ambient temperature
Autosampler Temp: 15° C.
Gradient: Isocratic
Method
Intact ADCs typically elute at ~16-18 minutes.
Aggregates typically elute at ~11-14 minutes.
Low molecular weight species typically elute at ~>20 minutes.

Protocol 8: Hydrophobic Interaction Chromatography
Materials
HPLC system, or equivalent, consisting of the following, or equivalent:
SRD-3600 SOLVENT RACK, 6 DEGASS. LINES
HPG-3400RS PUMP (Thermo Scientific)
HPG-3200RS PUMP (Thermo Scientific)
WPS-3000TFC ANALYTICAL AUTOSAMPLER (Thermo Scientific)
TCC-3000RS COLUMN THERMOSTAT (Thermo Scientific)
DAD-3000RS DETECTOR (Thermo Scientific)
Computer with Chromeleon software (Thermo Scientific)

Proteomix HIC Butyl-NPS, 5 um, non-porous, 4.6×35 mm (Sepax) column
Ammonium sulfate (($NH_4$)$_2$$SO_4$)
Sodium acetate (NaOAc)
i-Propanol
Water, HPLC grade
Mobile Phase A: 1.25 M ($NH_4$)$_2$$SO_4$, 25 mM NaOAc (pH 5.50)
Mobile Phase B: 75% 25 mM NaOAc (pH 5.50), 25% i-Propanol
Blank Solution: Water
Sample Preparation
Analytical Sample: ≤10 μL of neat ADC sample at a concentration of 1-5 mg/mL.
HPLC Parameters
Method File name: HIC_Gradient_1_AB
HPLC Column: Proteomix HIC Butyl-NPS, 5 um, non-porous, 4.6×35 mm (Sepax)
Flow Rate: 0.8 ml/min
Injection volume: 5 10 μL
Detection, UV: 214 nm
330 nm (for information only)
Column Temp: 25° C.
Autosampler Temp: 10° C.
Gradient

| Time (min) | % B |
| --- | --- |
| 0 | 0 |
| 1 | 0 |
| 13 | 100 |
| 14 | 100 |
| 14.1 | 0 |
| 18 | 0 |

Method

Flush the flow-path of the HPLC and column with water. Set up the HPLC under the operating conditions outlined above and equilibrate the system for a minimum of 10 minutes.

Protocol 9: Reverse Phase Chromatography

Materials

HPLC system, or equivalent, consisting of the following, or equivalent:
SRD-3600 SOLVENT RACK, 6 DEGASS. LINES
HPG-3400RS PUMP (Thermo Scientific)
HPG-3200RS PUMP (Thermo Scientific)
WPS-3000TFC ANALYTICAL AUTOSAMPLER (Thermo Scientific)
TCC-3000RS COLUMN THERMOSTAT (Thermo Scientific)
DAD-3000RS DETECTOR (Thermo Scientific)
Computer with Chromeleon software (Thermo Scientific)
Aeris Widepore XB-C18, 200 Å, 3.6 μm, 2.1×150 mm (Phenomenex, 00F-4482-AN)
Acetonitrile, HPLC grade.
Water, HPLC grade.
Trifluoroacetic acid (TFA), HPLC grade.
100 mM NaBorate, pH 8.4
500 mM DTT
49:49:2 Acetonitrile/Water/Formic acid
Mobile Phase A: Water+0.1% v/v TFA.
Mobile Phase B: Acetonitrile+0.1% v/v TFA.
Blank Solution: 1:1 v/v Acetonitrile/Water.

Sample Preparation

To 40 μL of sample (5 mg/ml) add water, 30 μl, NaBorate, 20 μl, and DTT (500 mM), 10 μL. Incubate at 37° C., 30 min, then add 100 pl of 49:49:2 Acetonitrile/Water/Formic acid.

HPLC Parameters

Method File name: RP_Aeris_Column6
HPLC Column: Aeris Widepore XB-C18, 200 Å, 3.6 μm, 2.1×150 mm (Phenomenex, 00E-4482-AN)
Flow Rate: 1.0 ml/min
Injection volume: 10 pl (or full loop)
Detection, UV: 214 nm
330 nm (for information only)
Column Temp: 80° C.
Autosampler Temp: 15° C.
Gradient

| Time (minutes) | % B |
| --- | --- |
| 0 | 22.5 |
| 1 | 22.5 |
| 11 | 50 |
| 11.5 | 90 |
| 13.5 | 90 |
| 14.5 | 22.5 |
| 16 | 22.5 |

Method

Set up the HPLC under the operating conditions outlined above and equilibrate the system for a minimum of 10 minutes. Inject a blank sample, followed by the sample for analysis.

Example 1: Characterization of Humanized Antibodies

The five antibodies described below were produced, expressed, and quantified according to Protocols 1-3 described herein. The expression levels recorded are shown below in Table 1.

Ab1 is an anti-AXL antibody comprising a VH domain having the sequence according to SEQ ID NO. 1, a VL domain having the sequence according to SEQ ID NO. 4, and a constant region derived from one or more human antibodies.

Ab2 is an anti-AXL antibody comprising a VH domain having the sequence according to SEQ ID NO. 2, a VL domain having the sequence according to SEQ ID NO. 5, and a constant region derived from one or more human antibodies.

Ab3 is an anti-AXL antibody comprising a VH domain having the sequence according to SEQ ID NO. 2, a VL domain having the sequence according to SEQ ID NO. 7, and a constant region derived from one or more human antibodies.

Ab4 is an anti-AXL antibody comprising a VH domain having the sequence according to SEQ ID NO. 3, a VL domain having the sequence according to SEQ ID NO. 5, and a constant region derived from one or more human antibodies.

Ab5 is an anti-AXL antibody comprising a VH domain having the sequence according to SEQ ID NO. 3, a VL domain having the sequence according to SEQ ID NO. 7, and a constant region derived from one or more human antibodies.

A stability assay was performed during which the antibodies were heated in sterile PBS at 40° C. for 60 hr and analysed for aggregation by SEC and for binding activity by human AXL ELISA. No increase in aggregation or loss in AXL binding activity was detected for any of the antibodies (see FIG. 2).

The antibodies were further characterised using Prtocols 5-9 as described herein. The results are shown below in Table 1 (all assays were performed on the HEK293F expression product unless otherwise stated; "F"=HEK293F, "T"=HEK293T).

TABLE 1

| Antibody | Expression (μg/mL) in ... | | | SEC % monomer 280 nm | | HIC retention time min | | Tm | RP HPLC LC2 peak % protein 280 nm | |
|---|---|---|---|---|---|---|---|---|---|---|
| | T | F | CHO | CHO | F | F | CHO | pI (°C.) | F | CHO |
| Ab1 | 33.7, 40.1 | 7.16 | 366 | 97.9 | 87% | 4.5 | 4.5 | 8.05 69.52 | 0 | 0 |
| Ab2 | 18.2 | 2.55 | 265 | 97.6 | 86% | 5.2 | 5.2 | 8.06 59.71 | 6.4% | 5.9% |
| Ab3 | 15.2 | 2.24 | 287 | 98.3 | 88% | 4.8 | 4.7 | 8.15 62.05 | 0 | 0 |
| Ab4 | 17.8 | 1.91 | 306 | 96.9 | 96% | 5.6 | 5.6 | 7.56 60.32 | 8.1% | 5.9% |
| Ab5 | 16.5 | 1.95 | 298 | 97.7 | 98% | 5.0 | 4.9 | 7.54 63.06 | 0 | 0 |

Binding of the antibodies to AXL antigens indicated that binding was unusually sensitive to both antigen preparation and presentation and antibody geometry.

Initial measurements by ELISA using Axl-Strep-His antigen, as disclosed in Protocol 4 suggested that the binding of antibodies comprising humanised 1H12 heavy and light chains (Ab2-Ab5) were broadly similar to the antibody comprising the murine VH and VL domains (Ab1) (see FIG. 1).

SPR measurements of antibody affinity using Axl-Strep-His antigen indicated that Ab2, Ab3, and Ab5 had higher affinity for Axl-Strep-His than Ab1 (see Table 2).

SPR measurements of antibody affinity using Axl-Fc antigen indicated that Ab2 and Ab4 had higher affinity for Axl-Fc than Ab1 (see Table 2).

TABLE 2

| | AXL-Strep-His antigen | | | AXL-Fc antigen | | |
|---|---|---|---|---|---|---|
| Antibody | ka (1/Ms) | kd (1/s) | KD1 (nM) | ka (1/Ms) | kd (1/s) | KD (nM) |
| Ab1 | 1.31E+04 | 5.33E−04 | 40.7** | 3.09E+04 | 1.42E−04 | 4.6 |
| Ab2 | 1.32E+04 | 4.41E−04 | 33.4 | 8.37E+04 | 1.54E−04 | 1.84 |
| Ab3 | 1.92E+04 | 6.36E−04 | 33.1 | 2.45E+04 | 2.00E−04 | 8.5 |
| Ab4 | 9759 | 5.90E−04 | 60.4 | 2.90E+05 | 3.96E−04 | 1.37 |
| Ab5 | 1.89E+04 | 4.35E−04 | 23 | 2.06E+04 | 1.59E−04 | 7.69 |

**The observed binding data for 1H12 chimeric antibody did not fit monovalent or bivalent algorithms well, so in this one case, a "heterogeneous ligand" model was used. For all other binding data, the bivalent ligand model was used.

Abbreviations

5 Å+ set The FW residues in the 5A CDR envelope, defined by the homology model, together with the canonical, vernier and VH/VK interface residues
1H12 The anti-AXL mouse monoclonal antibody
1H12 VK VK of mouse 1H12 antibody
1H12RKA1 Humanised version, A1, of 1H12 VK
1H12RHA Humanised version, A, of 1H12 VH
1H12RHA× IgG1k antibody comprising the VH and VK constructs 1H12RHA and
1H12RKA 1H12RKA respectively, functionally contiguous with the constant regions of human IgG1 and Ig-kappa heavy and light chains respectively
A Adenine
A Angstrom
Ac acetyl
Acm acetamidomethyl
Alloc allyloxycarbonyl
B7 The anti-LPA antibody product of mouse hybridoma clone B7
Boc di-tert-butyl dicarbonate
bp base pairs
Bzl benzyl, where Bzl-OMe is methoxybenzyl and Bzl-Me is methylbenzene
C Cytosine
Cbz or Z benzyloxy-carbonyl, where Z—Cl and Z—Br are chloro- and bromobenzyloxy carbonyl respectively
CDR Complementarity determining region in the immunoglobulin variable regions, defined using the Kabat numbering system
CHO Chinese hamster ovary cell line
D-gene Diversity gene
DMF N,N-dimethylformamide
DNA Deoxyribonucleic acid
Dnp dinitrophenyl
DTT dithiothreitol
Fmoc 9H-fluoren-9-ylmethoxycarbonyl
FW Framework region: the immunoglobulin variable regions excluding the CDR regions
G Guanine
IgG Immunoglobulin G
imp N-10 imine protecting group: 3-(2-methoxyethoxy) propanoate-Val-Ala-PAB
MC-OSu maleimidocaproyl-O-N-succinimide
J-gene Joining gene
Kabat an immunoglobulin alignment and numbering system pioneered by Elvin A Kabat
mAb monoclonal antibody
Moc methoxycarbonyl
MP maleimidopropanamide
Mtr 4-methoxy-2,3,6-trimethtylbenzenesulfonyl
PAB para-aminobenzyloxycarbonyl
PEG ethyleneoxy
PNZ p-nitrobenzyl carbamate
Psec 2-(phenylsulfonyl)ethoxycarbonyl
T Thymine
TBDMS tert-butyldimethylsilyl
TBDPS tert-butyldiphenylsilyl
t-Bu tert-butyl
Teoc 2-(trimethylsilyl)ethoxycarbonyl
Tos tosyl
Troc 2,2,2-trichlorethoxycarbonyl chloride
Trt trityl V region The segment of IgG chains which is variable in sequence between different antibodies. It extends to Kabat residue 109 in the light chain and 113 in the heavy chain.

VCI Framework residue classified as vernier or canonical or VH-VL interface

V-gene The gene segment that is rearranged, together with a J (and D for VH) gene, to generate a complete VK (or VH)

VH Immunoglobulin heavy chain variable region

VK Immunoglobulin kappa light chain variable region

Xan xanthyl

REFERENCES

[1] C. Chothia, et al., "Domain association in immunoglobulin molecules. The packing of variable domains," J Mol. Biol. 186(3), 651 (1985).

[2] J. Foote and G. Winter, "Antibody framework residues affecting the conformation of the hypervariable loops," J Mol. Biol. 224(2), 487 (1992).

[3] E. A Kabat, et al., sequences of proteins of immunological interest, 5 ed. (NIH National Technical Information Service, 1991).

[4] V. Morea, A. M. Lesk, and A. Tramontano, "Antibody modeling: implications for engineering and design," Methods 20(3), 267 (2000).

Statements of Disclosure

1. An isolated humanized antibody that binds to AXL, wherein the isolated humanized antibody comprises a heavy chain variable region having the amino acid sequence of SEQ ID NO: 1, SEQ ID NO: 2 or SEQ ID NO: 3.

2. The isolated humanized antibody according to statement 1, wherein the isolated humanized antibody further comprises a light chain variable region having the amino acid sequence of SEQ ID NO: 4, 5, 6, 7, or 8; and, optionally, comprises a constant region derived from one or more human antibodies.

3. The isolated humanized antibody according to either one of statements 1 or 2, wherein the isolated humanized antibody comprises:

(i) a heavy chain variable region having the amino acid sequence of SEQ ID NO: 1 and a light chain variable region having the amino acid sequence of SEQ ID NO: 4;

(ii) a heavy chain variable region having the amino acid sequence of SEQ ID NO: 1 and a light chain variable region having the amino acid sequence of SEQ ID NO: 5;

(iii) a heavy chain variable region having the amino acid sequence of SEQ ID NO: 1 and a light chain variable region having the amino acid sequence of SEQ ID NO: 6;

(iv) a heavy chain variable region having the amino acid sequence of SEQ ID NO: 1 and a light chain variable region having the amino acid sequence of SEQ ID NO: 7;

(v) a heavy chain variable region having the amino acid sequence of SEQ ID NO: 1 and a light chain variable region having the amino acid sequence of SEQ ID NO: 8;

(vi) a heavy chain variable region having the amino acid sequence of SEQ ID NO: 2 and a light chain variable region having the amino acid sequence of SEQ ID NO: 4;

(vii) a heavy chain variable region having the amino acid sequence of SEQ ID NO: 2 and a light chain variable region having the amino acid sequence of SEQ ID NO: 5;

(viii) a heavy chain variable region having the amino acid sequence of SEQ ID NO: 2 and a light chain variable region having the amino acid sequence of SEQ ID NO: 6;

(ix) a heavy chain variable region having the amino acid sequence of SEQ ID NO: 2 and a light chain variable region having the amino acid sequence of SEQ ID NO: 7;

(x) a heavy chain variable region having the amino acid sequence of SEQ ID NO: 2 and a light chain variable region having the amino acid sequence of SEQ ID NO: 8;

(xi) a heavy chain variable region having the amino acid sequence of SEQ ID NO: 3 and a light chain variable region having the amino acid sequence of SEQ ID NO: 4;

(xii) a heavy chain variable region having the amino acid sequence of SEQ ID NO: 3 and a light chain variable region having the amino acid sequence of SEQ ID NO: 5;

(xiii) a heavy chain variable region having the amino acid sequence of SEQ ID NO: 3 and a light chain variable region having the amino acid sequence of SEQ ID NO: 6;

(xiv) a heavy chain variable region having the amino acid sequence of SEQ ID NO: 3 and a light chain variable region having the amino acid sequence of SEQ ID NO: 7; or (xv) a heavy chain variable region having the amino acid sequence of SEQ ID NO: 3 and a light chain variable region having the amino acid sequence of SEQ ID NO: 8.

4. The humanized antibody according to any one of statements 1 to 3, wherein said antibody binds human AXL with an affinity (Kd) of at least $10^{-6}$ M.

5. The humanized antibody according to statement 3, wherein said antibody binds human AXL with an affinity (Kd) of at least $10^{-6}$ M.

6. The humanized antibody according to any one of statements 1 to 5, wherein said antibody competitively inhibits the binding to human AXL of an antibody comprising a heavy chain variable region having the amino acid sequence of SEQ ID NO: 1 and a light chain variable region having the amino acid sequence of SEQ ID NO: 4.

7. The humanized antibody according to any one of statements 1 to 6, wherein said antibody binds the Axl-Strep-His antigen with an affinity (Kd) of no more 0.6 of the Kd of an antibody comprising a VH domain having the sequence according to SEQ ID NO. 1, a VL domain having the sequence according to SEQ ID NO. 4, and a constant region derived from one or more human antibodies.

8. The humanized antibody according to any one of statements 1 to 7, wherein said antibody binds the Axl-Fc antigen with an affinity (Kd) of no more 0.5 of the Kd of an antibody comprising a VH domain having the sequence according to SEQ ID NO. 1, a VL domain having the sequence according to SEQ ID NO. 4, and a constant region derived from one or more human antibodies.

9. The humanized antibody according to any one of statements 1 to 8, wherein said antibody competitively inhibits the binding to human AXL of the mouse 1H12 antibody.

10. The humanized antibody according to any one of statements 1 to 9, wherein said antibody has a pI of at least 8.00.

11. The humanized antibody according to statement 10 wherein the antibody has a pI of at least 8.15.

12. The humanized antibody according to any one of statements 1 to 11, wherein said antibody or antibody fragment has a constant region of either isotype IgG1, IgG2, IgG3 or IgG4, or a mutated IgG constant region, and optionally a light chain constant region of isotype kappa or lambda.

13. The humanized antibody according to any one of statements 1 to 12, wherein the humanized antibody fragment is a scFv, Fab or F(ab')$_2$.

14. The antibody according to any one of statements 1 to 13, for use in therapy.

15. The antibody according to any one of statements 1 to 14, for use in the treatment of a proliferative disease in a subject.

16. The antibody according to any one of statements 1 to 15, for use in the treatment of a proliferative disease in a subject, wherein the subject has raised levels of AXL, Akt3, or GAS6 and wherein the method comprises identifying that the subject has raised levels of AXL, Akt3, or GAS6 and administering the antibody or conjugate to the patient.

17. The antibody or drug-conjugate according to any one of statements 1 to 16, for use in the treatment of a proliferative disease in a subject, wherein the proliferative disease is associated with raised levels of AXL, Akt3, or GAS6, the method comprising administering the conjugate to the patient.

18. The drug-conjugate according to any one of statements 15 to 17, wherein the disease is cancer.

19. A pharmaceutical composition comprising the antibody of any one of statements 1 to 13 and a pharmaceutically acceptable diluent, carrier or excipient.

20. The pharmaceutical composition of statement 19 further comprising a therapeutically effective amount of a chemotherapeutic agent.

21. Use of an antibody according to any one of statements 1 to 13 in the preparation of a medicament for use in the treatment of a proliferative disease in a subject.

22. A method of treating cancer comprising administering to a patient the pharmaceutical composition according to either one of statements 20 or 21.

23. The method of statement 22 wherein the patient is administered a chemotherapeutic agent, in combination with the composition.

24. A polynucleotide encoding a humanized antibody according to any one of statements 1 to 13.

25. A vector comprising the polynucleotide of statement 24.

26. The vector of statement 25 wherein the vector is an expression vector.

27. A host cell comprising a vector according to either one of statements 25 or 26.

28. The host cell according to statement 27 wherein the host cell is prokaryotic, eukaryotic, or mammalian.

29. A method of selecting an individual for treatment with the according to any one of statements 1 to 13, or with the pharmaceutical composition of either one of statements 20 or 21, which method comprises assessing the level of AXL;
  wherein individuals having raised levels of AXL are selected for treatment.

30. A method of timing the application of treatment of an individual with the antibody or drug-conjugate according to any one of statements 1 to 13, or with the pharmaceutical composition of either one of statements 20 or 21, which method comprises assessing the level of AXL;
  wherein the treatment is applied if the individual has raised levels of AXL.

31. The method according to either one of statements 29 or 30, wherein the individual has cancer and treatment reduces tumour volume.

SEQUENCES

SEQ ID NO: 1 [1H12VH]
MGFKMESQFQVFVFVFLWLSGVDGEVQLVESGGDLVKPGGSLKLSCAASG
FTFSSYGMSWVRQTPDKRLEWVATISSGGSYTYYPDSVKGRFTISRDNAK
NTLYLQMSSLKSEDTAMYYCARHPIYYTYDDTMDYWGQGTSVTVSS

SEQ ID NO: 2 [1H12RHA]
MGFKMESQFQVFVFVFLWLSGVDGVQLVESGGGVVQPGRSLRLSCAASG
FTFSSYGMSVRQAPGKGLEWVATISSGGSYTYYPDSVKGRFTISRDNSKN
TLYLQMNSLRAEDTAVYYCARHPIYYTYDDTMDYWGQGTTVTVSS

SEQ ID NO: 3 [1H12RHB]
MGFKMESQFQVFVFVFLWLSGVDGEVQLVESGGGLVQPGGSLRLSCAASG
FTFSSYGMSWVRQAPGKGLEWVATISSGGSYTYYPDSVKGRFTISRDNAK
NSLYLQMNSLRAEDTAVYYCARHPIYYTYDDTMDYWGQGTLVTVSS

SEQ ID NO: 4 [1H12VK]
MGFKMESQFQVFVFVFLWLSGVDGENVLTQSPAIMAASPGEKVTMTCSAS
SSVSSGNFHWYQQKPGTSPKLWIYRTSNLASGVPARFSGSGSGTSYSLTI
SSMEAEDAATYYCQQWSGYPWTFGGGTKLEIK

SEQ ID NO: 5 [1H12RKA]
MGFKMESQFQVFVFVFLWLSGVDGEIVLTQSPATLSLSPGERATLSCSAS
SSVSSGNFHWYQQKPGLAPRLLIYRTSNLASGIPDRFSGSGSGTDFTLTI
SRLEPEDFAVYYCQQWSGYPWTFGPGTKVDIK

SEQ ID NO: 6 [1H12RKA1]
MGFKMESQFQVFVFVFLWLSGVDGENVLTQSPATLSLSPGERATLSCSAS
SSVSSGNFHWYQQKPGLAPRLWIYRTSNLASGIPDRFSGSGSGTDYTLTI
SRLEPEDFAVYYCQQWSGYPWTFGPGTKVDIK

SEQ ID NO: 7 [1H12RKB]
MGFKMESQFQVFVFVFLWLSGVDGEIVLTQSPGTLSLSPGERATLSCSAS
SSVSSGNFHWYQQKPGLAPRLLIYRTSNLASGIPARFSGSGSGTDFTLTI
SSLEPEDFAVYYCQQWSGYPWTFGGGTKLEIK

SEQ ID NO: 8 [1H12RKB1]
MGFKMESQFQVFVFVFLWLSGVDGENVLTQSPGTLSLSPGERATLSCSAS
SSVSSGNFHWYQQKPGLAPRLWIYRTSNLASGIPARFSGSGSGTDYTLTI
SSLEPEDFAVYYCQQWSGYPWTFGGGTKLEIK

SEQ ID NO: 9 [Human Axl]
MAWRCPRMGRVPLAWCLALCGWACMAPRGTQAEESPFVGNPGNITGARGL
TGTLRCQLQVQGEPPEVHWLRDGQILELADSTQTQVPLGEDEQDDWIVVS
QLRITSLQLSDTGQYQCLVFLGHQTFVSQPGYVGLEGLPYFLEEPEDRTV
AANTPFNLSCQAQGPPEPVDLLWLQDAVPLATAPGHGPQRSLHVPGLNKT
SSFSCEAHNAKGVTTSRTATITVLPQQPRNLHLVSRQPTELEVAWTPGLS
GIYPLTHCTLQAVLSDDGMGIQAGEPDPPEEPLTSQASVPPHQLRLGSLH
PHTPYHIRVACTSSQGPSSVVTHWLPVETPEGVPLGPPENISATRNGSQA
FVHWQEPRAPLQGTLLGYRLAYQGQDTPEVLMDIGLRQEVTLELQGDGSV
SNLTVCVAAYTAAGDGPWSLPVPLEAWRPGQAQPVHQLVKEPSTPAFSWP
WWYVLLGAVVAAACVLILALFLVHRRKKETRYGEVFEPTVERGELVVRYR
VRKSYSRRTTEATLNSLGISEELKEKLRDVMVDRHKVALGKTLGEGEFGA
VMEGQLNQDDSILKVAVKTMKIAICTRSELEDFLSEAVCMKEFDHPNVMR
LIGVCFQGSERESFPAPVVILPFMKHGDLHSFLLYSRLGDQPVYLPTQML
VKFMADIASGMEYLSTKRFIHRDLAARNCMLNENMSVCVADFGLSKKIYN
GDYYRQGRIAKMPVKWIAIESLADRVYTSKSDVWSFGVTMWEIATRGQTP
YPGVENSEIYDYLRRGNRLKQPADCLDGLYALMSRCWELNPQDRPSFTEL
REDLENTLKALPPAQEPDEILYVNMDEGGGYPEPPGAAGGADPPTQPDPK
DSCSCLTAAEVHPAGRYVLCPSTTPSPAQPADRGSPAAPGQEDGA SEQ ID NO: 10 [Murine Axl]
MGRVPLAWWLALCCWGCAAHKDTQTEAGSPFVGNPGNITGARGLTGTLRC
ELQVQGEPPEVVWLRDGQILELADNTQTQVPLGEDWQDEWKVVSQLRISA
LQLSDAGEYQCMVHLEGRTFVSQPGFVGLEGLPYFLEEPEDKAVPANTPF
NLSCQAQGPPEPVTLLWLQDAVPLAPVTGHSSQHSLQTPGLNKTSSFSCE
AHNAKGVTTSRTATITVLPQRPHHLHVVSRQPTELEVAWTPGLSGIYPLT
HCNLQAVLSDDGVGIWLGKSDPPEDPLTLQVSVPPHQLRLEKLLPHTPYH
IRISCSSSQGPSPVVTHWLPVETTEGVPLGPPENVSAMRNGSQVLVRWQE
PRVPLQGTLLGYRLAYRGQDTPEVLMDIGLTREVTLELRGDRPVANLTVS
VTAYTSAGDGPWSLPVPLEPWRPGQGQPLHHLVSEPPPRAFSWPWWYVLL
GALVAAACVLILALFLVHRRKKETRYGEVFEPTVERGELVVRYRVRKSYS
RRTTEATLNSLGISEELKEKLRDVMVDRHKVALGKTLGEGEFGAVMEGQL
NQDDSILKVAVKTMKIAICTRSELEDFLSEAVCMKEFDHPNVMRLIGVCF
QGSDREGFPEPVVILPFMKHGDLHSFLLYSRLGDQPVFLPTQMLVKFMAD
IASGMEYLSTKRFIHRDLAARNCMLNENMSVCVADFGLSKKIYNGDYYRQ
GRIAKMPVKWIAIESLADRVYTSKSDVWSFGVTMWEIATRGQTPYPGVEN
SEIYDYLRQGNRLKQPVDCLDGLYALMSRCWELNPRDRPSFAELREDLEN
TLKALPPAQEPDEILYVNMDEGGSHLEPRGAAGGADPPTQPDPKDSCSCL
TAADVHSAGRYVLCPSTAPGPTLSADRGCPAPPGQEDGA

The invention claimed is:

1. An isolated humanized antibody that binds to AXL, wherein the isolated humanized antibody comprises:
   (a) a heavy chain variable region having the amino acid sequence of SEQ ID NO: 2; and
   (b) a light chain variable region having the amino acid sequence of SEQ ID NO: 4, 5, 6, 7, or 8.

2. The isolated humanized antibody according to claim 1, wherein the isolated humanized antibody comprises:
   (i) a heavy chain variable region having the amino acid sequence of SEQ ID NO: 2 and a light chain variable region having the amino acid sequence of SEQ ID NO: 4;
   (ii) a heavy chain variable region having the amino acid sequence of SEQ ID NO: 2 and a light chain variable region having the amino acid sequence of SEQ ID NO: 5;
   (iii) a heavy chain variable region having the amino acid sequence of SEQ ID NO: 2 and a light chain variable region having the amino acid sequence of SEQ ID NO: 6;
   (iv) a heavy chain variable region having the amino acid sequence of SEQ ID NO: 2 and a light chain variable region having the amino acid sequence of SEQ ID NO: 7; or
   (v) a heavy chain variable region having the amino acid sequence of SEQ ID NO: 2 and a light chain variable region having the amino acid sequence of SEQ ID NO: 8.

3. The humanized antibody according to claim 1, wherein said antibody competitively inhibits the binding to human AXL of an antibody comprising a heavy chain variable region having the amino acid sequence of SEQ ID NO: 1 and a light chain variable region having the amino acid sequence of SEQ ID NO: 4.

4. The humanized antibody according to claim 1, wherein said antibody binds the Axl-Strep-His antigen with an affinity (Kd) of no more 0.6 of the Kd of an antibody comprising a VH domain having the sequence according to SEQ ID NO. 1, a VL domain having the sequence according to SEQ ID NO. 4, and a constant region derived from one or more human antibodies.

5. The humanized antibody according to claim 1, wherein said antibody has a constant region of either isotype IgG1, IgG2, IgG3 or IgG4, or a mutated IgG constant region, and optionally a light chain constant region of isotype kappa or lambda.

6. The humanized antibody according to claim 1, wherein the humanized antibody is an antibody fragment selected from scFv, Fab or F(ab')$_2$.

7. The antibody of claim 1, which further comprises a constant region derived from one or more human antibodies.

8. The antibody of claim 1, which comprises a heavy chain variable region having the amino acid sequence of SEQ ID NO: 2 and a light chain variable region having the amino acid sequence of SEQ ID NO: 7.

9. A pharmaceutical composition comprising the antibody of claim 1 and a pharmaceutically acceptable diluent, carrier or excipient, optionally further comprising a therapeutically effective amount of a chemotherapeutic agent.

10. A method of treating a proliferative disease in a subject, which comprises administering the antibody of claim 1 to the subject, wherein the subject has raised levels of AXL, and optionally wherein the disease is cancer.

11. A method of selecting an individual for treatment with the antibody according to claim 1, which method comprises assessing the level of AXL; wherein individuals having raised levels of AXL are selected for treatment, and optionally wherein the individual has cancer and the treatment reduces tumour volume.

* * * * *

UNITED STATES PATENT AND TRADEMARK OFFICE
CERTIFICATE OF CORRECTION

PATENT NO. : 11,059,893 B2
APPLICATION NO. : 15/566635
DATED : July 13, 2021
INVENTOR(S) : Van Berkel et al.

Page 1 of 1

It is certified that error appears in the above-identified patent and that said Letters Patent is hereby corrected as shown below:

In the Specification

Column 34, Line 7, SEQ ID NO. 2 should read as follows:
MGFKMESQFQVFVFVFLWLSGVDGQVQLVESGGGVVQPGRSLRLSCAASGFTFSSYGMSWV
RQAPGKGLEWVATISSGGSYTYYPDSVKGRFTISRDNSKNTLYLQMNSLRAEDTAVYYCARH
PIYYTYDDTMDYWGQGTTVTVSS Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 10

<210> SEQ ID NO 1
<211> LENGTH: 146
<212> TYPE: PRT
<213> ORGANISM: Artificial sequence
<220> FEATURE:
<223> OTHER INFORMATION: Synthetic heavy chain variable region 1H12VH

<400> SEQUENCE: 1

```
Met Gly Phe Lys Met Glu Ser Gln Phe Gln Val Phe Val Phe
1               5                  10                  15

Leu Trp Leu Ser Gly Val Asp Gly Glu Val Gln Leu Val Glu Ser Gly
            20                  25                  30

Gly Asp Leu Val Lys Pro Gly Gly Ser Leu Lys Leu Ser Cys Ala Ala
            35                  40                  45

Ser Gly Phe Thr Phe Ser Ser Tyr Gly Met Ser Trp Val Arg Gln Thr
    50                  55                  60

Pro Asp Lys Arg Leu Glu Trp Val Ala Thr Ile Ser Ser Gly Gly Ser
65                  70                  75                  80

Tyr Thr Tyr Tyr Pro Asp Ser Val Lys Gly Arg Phe Thr Ile Ser Arg
                85                  90                  95

Asp Asn Ala Lys Asn Thr Leu Tyr Leu Gln Met Ser Ser Leu Lys Ser
            100                 105                 110

Glu Asp Thr Ala Met Tyr Tyr Cys Ala Arg His Pro Ile Tyr Tyr Thr
            115                 120                 125

Tyr Asp Asp Thr Met Asp Tyr Trp Gly Gln Gly Thr Ser Val Thr Val
            130                 135                 140

Ser Ser
145
```

<210> SEQ ID NO 2
<211> LENGTH: 146
<212> TYPE: PRT
<213> ORGANISM: Artificial sequence
<220> FEATURE:
<223> OTHER INFORMATION: Synthetic heavy chain variable region 1H12RHA

<400> SEQUENCE: 2

```
Met Gly Phe Lys Met Glu Ser Gln Phe Gln Val Phe Val Phe
1               5                  10                  15

Leu Trp Leu Ser Gly Val Asp Gly Gln Val Gln Leu Val Glu Ser Gly
            20                  25                  30

Gly Gly Val Val Gln Pro Gly Arg Ser Leu Arg Leu Ser Cys Ala Ala
            35                  40                  45

Ser Gly Phe Thr Phe Ser Ser Tyr Gly Met Ser Trp Val Arg Gln Ala
    50                  55                  60

Pro Gly Lys Gly Leu Glu Trp Val Ala Thr Ile Ser Ser Gly Gly Ser
65                  70                  75                  80

Tyr Thr Tyr Tyr Pro Asp Ser Val Lys Gly Arg Phe Thr Ile Ser Arg
                85                  90                  95

Asp Asn Ser Lys Asn Thr Leu Tyr Leu Gln Met Asn Ser Leu Arg Ala
            100                 105                 110

Glu Asp Thr Ala Val Tyr Tyr Cys Ala Arg His Pro Ile Tyr Tyr Thr
            115                 120                 125

Tyr Asp Asp Thr Met Asp Tyr Trp Gly Gln Gly Thr Thr Val Thr Val
            130                 135                 140
```

Ser Ser
145

<210> SEQ ID NO 3
<211> LENGTH: 146
<212> TYPE: PRT
<213> ORGANISM: Artificial sequence
<220> FEATURE:
<223> OTHER INFORMATION: Synthetic heavy chain variable region 1H12RHB

<400> SEQUENCE: 3

Met Gly Phe Lys Met Glu Ser Gln Phe Gln Val Phe Val Phe Val Phe
1               5                   10                  15

Leu Trp Leu Ser Gly Val Asp Gly Glu Val Gln Leu Val Glu Ser Gly
            20                  25                  30

Gly Gly Leu Val Gln Pro Gly Gly Ser Leu Arg Leu Ser Cys Ala Ala
        35                  40                  45

Ser Gly Phe Thr Phe Ser Ser Tyr Gly Met Ser Trp Val Arg Gln Ala
    50                  55                  60

Pro Gly Lys Gly Leu Glu Trp Val Ala Thr Ile Ser Ser Gly Gly Ser
65                  70                  75                  80

Tyr Thr Tyr Tyr Pro Asp Ser Val Lys Gly Arg Phe Thr Ile Ser Arg
                85                  90                  95

Asp Asn Ala Lys Asn Ser Leu Tyr Leu Gln Met Asn Ser Leu Arg Ala
            100                 105                 110

Glu Asp Thr Ala Val Tyr Tyr Cys Ala Arg His Pro Ile Tyr Tyr Thr
        115                 120                 125

Tyr Asp Asp Thr Met Asp Tyr Trp Gly Gln Gly Thr Leu Val Thr Val
    130                 135                 140

Ser Ser
145

<210> SEQ ID NO 4
<211> LENGTH: 132
<212> TYPE: PRT
<213> ORGANISM: Artificial sequence
<220> FEATURE:
<223> OTHER INFORMATION: Synthetic light chain variable region 1H12VK

<400> SEQUENCE: 4

Met Gly Phe Lys Met Glu Ser Gln Phe Gln Val Phe Val Phe Val Phe
1               5                   10                  15

Leu Trp Leu Ser Gly Val Asp Gly Glu Asn Val Leu Thr Gln Ser Pro
            20                  25                  30

Ala Ile Met Ala Ala Ser Pro Gly Glu Lys Val Thr Met Thr Cys Ser
        35                  40                  45

Ala Ser Ser Ser Val Ser Ser Gly Asn Phe His Trp Tyr Gln Gln Lys
    50                  55                  60

Pro Gly Thr Ser Pro Lys Leu Trp Ile Tyr Arg Thr Ser Asn Leu Ala
65                  70                  75                  80

Ser Gly Val Pro Ala Arg Phe Ser Gly Ser Gly Ser Gly Thr Ser Tyr
                85                  90                  95

Ser Leu Thr Ile Ser Ser Met Glu Ala Glu Asp Ala Ala Thr Tyr Tyr
            100                 105                 110

Cys Gln Gln Trp Ser Gly Tyr Pro Trp Thr Phe Gly Gly Gly Thr Lys
        115                 120                 125

Leu Glu Ile Lys
    130

<210> SEQ ID NO 5
<211> LENGTH: 132
<212> TYPE: PRT
<213> ORGANISM: Artificial sequence
<220> FEATURE:
<223> OTHER INFORMATION: Synthetic light chain variable region 1H12RKA

<400> SEQUENCE: 5

```
Met Gly Phe Lys Met Glu Ser Gln Phe Gln Val Phe Val Phe
1               5                   10                  15

Leu Trp Leu Ser Gly Val Asp Gly Glu Ile Val Leu Thr Gln Ser Pro
            20                  25                  30

Ala Thr Leu Ser Leu Ser Pro Gly Glu Arg Ala Thr Leu Ser Cys Ser
        35                  40                  45

Ala Ser Ser Val Ser Ser Gly Asn Phe His Trp Tyr Gln Gln Lys
    50                  55                  60

Pro Gly Leu Ala Pro Arg Leu Leu Ile Tyr Arg Thr Ser Asn Leu Ala
65                  70                  75                  80

Ser Gly Ile Pro Asp Arg Phe Ser Gly Ser Gly Ser Gly Thr Asp Phe
                85                  90                  95

Thr Leu Thr Ile Ser Arg Leu Glu Pro Glu Asp Phe Ala Val Tyr Tyr
            100                 105                 110

Cys Gln Gln Trp Ser Gly Tyr Pro Trp Thr Phe Gly Pro Gly Thr Lys
        115                 120                 125

Val Asp Ile Lys
    130
```

<210> SEQ ID NO 6
<211> LENGTH: 132
<212> TYPE: PRT
<213> ORGANISM: Artificial sequence
<220> FEATURE:
<223> OTHER INFORMATION: Synthetic light chain variable region 1H12RKA1

<400> SEQUENCE: 6

```
Met Gly Phe Lys Met Glu Ser Gln Phe Gln Val Phe Val Phe
1               5                   10                  15

Leu Trp Leu Ser Gly Val Asp Gly Glu Asn Val Leu Thr Gln Ser Pro
            20                  25                  30

Ala Thr Leu Ser Leu Ser Pro Gly Glu Arg Ala Thr Leu Ser Cys Ser
        35                  40                  45

Ala Ser Ser Val Ser Ser Gly Asn Phe His Trp Tyr Gln Gln Lys
    50                  55                  60

Pro Gly Leu Ala Pro Arg Leu Trp Ile Tyr Arg Thr Ser Asn Leu Ala
65                  70                  75                  80

Ser Gly Ile Pro Asp Arg Phe Ser Gly Ser Gly Ser Gly Thr Asp Tyr
                85                  90                  95

Thr Leu Thr Ile Ser Arg Leu Glu Pro Glu Asp Phe Ala Val Tyr Tyr
            100                 105                 110

Cys Gln Gln Trp Ser Gly Tyr Pro Trp Thr Phe Gly Pro Gly Thr Lys
        115                 120                 125

Val Asp Ile Lys
    130
```

<210> SEQ ID NO 7
<211> LENGTH: 132
<212> TYPE: PRT

<213> ORGANISM: Artificial sequence
<220> FEATURE:
<223> OTHER INFORMATION: Synthetic light chain variable region 1H12RKB

<400> SEQUENCE: 7

Met Gly Phe Lys Met Glu Ser Gln Phe Gln Val Phe Val Phe
1               5                   10                  15

Leu Trp Leu Ser Gly Val Asp Gly Glu Ile Val Leu Thr Gln Ser Pro
            20                  25                  30

Gly Thr Leu Ser Leu Ser Pro Gly Glu Arg Ala Thr Leu Ser Cys Ser
            35                  40                  45

Ala Ser Ser Val Ser Ser Gly Asn Phe His Trp Tyr Gln Gln Lys
        50                  55                  60

Pro Gly Leu Ala Pro Arg Leu Leu Ile Tyr Arg Thr Ser Asn Leu Ala
65                  70                  75                  80

Ser Gly Ile Pro Ala Arg Phe Ser Gly Ser Gly Ser Gly Thr Asp Phe
            85                  90                  95

Thr Leu Thr Ile Ser Ser Leu Glu Pro Glu Asp Phe Ala Val Tyr Tyr
                100                 105                 110

Cys Gln Gln Trp Ser Gly Tyr Pro Trp Thr Phe Gly Gly Gly Thr Lys
            115                 120                 125

Leu Glu Ile Lys
    130

<210> SEQ ID NO 8
<211> LENGTH: 132
<212> TYPE: PRT
<213> ORGANISM: Artificial sequence
<220> FEATURE:
<223> OTHER INFORMATION: Synthetic light chain variable region 1H12RKB1

<400> SEQUENCE: 8

Met Gly Phe Lys Met Glu Ser Gln Phe Gln Val Phe Val Phe
1               5                   10                  15

Leu Trp Leu Ser Gly Val Asp Gly Glu Asn Val Leu Thr Gln Ser Pro
            20                  25                  30

Gly Thr Leu Ser Leu Ser Pro Gly Glu Arg Ala Thr Leu Ser Cys Ser
            35                  40                  45

Ala Ser Ser Val Ser Ser Gly Asn Phe His Trp Tyr Gln Gln Lys
        50                  55                  60

Pro Gly Leu Ala Pro Arg Leu Trp Ile Tyr Arg Thr Ser Asn Leu Ala
65                  70                  75                  80

Ser Gly Ile Pro Ala Arg Phe Ser Gly Ser Gly Ser Gly Thr Asp Tyr
            85                  90                  95

Thr Leu Thr Ile Ser Ser Leu Glu Pro Glu Asp Phe Ala Val Tyr Tyr
                100                 105                 110

Cys Gln Gln Trp Ser Gly Tyr Pro Trp Thr Phe Gly Gly Gly Thr Lys
            115                 120                 125

Leu Glu Ile Lys
    130

<210> SEQ ID NO 9
<211> LENGTH: 894
<212> TYPE: PRT
<213> ORGANISM: Homo sapiens

<400> SEQUENCE: 9

Met Ala Trp Arg Cys Pro Arg Met Gly Arg Val Pro Leu Ala Trp Cys

-continued

```
  1               5                  10                 15
Leu Ala Leu Cys Gly Trp Ala Cys Met Ala Pro Arg Gly Thr Gln Ala
             20                 25                 30
Glu Glu Ser Pro Phe Val Gly Asn Pro Gly Asn Ile Thr Gly Ala Arg
             35                 40                 45
Gly Leu Thr Gly Thr Leu Arg Cys Gln Leu Gln Val Gln Gly Glu Pro
 50                 55                 60
Pro Glu Val His Trp Leu Arg Asp Gly Gln Ile Leu Glu Leu Ala Asp
 65                 70                 75                 80
Ser Thr Gln Thr Gln Val Pro Leu Gly Glu Asp Glu Gln Asp Asp Trp
             85                 90                 95
Ile Val Val Ser Gln Leu Arg Ile Thr Ser Leu Gln Leu Ser Asp Thr
             100                105                110
Gly Gln Tyr Gln Cys Leu Val Phe Leu Gly His Gln Thr Phe Val Ser
             115                120                125
Gln Pro Gly Tyr Val Gly Leu Glu Gly Leu Pro Tyr Phe Leu Glu Glu
             130                135                140
Pro Glu Asp Arg Thr Val Ala Ala Asn Thr Pro Phe Asn Leu Ser Cys
145                150                155                160
Gln Ala Gln Gly Pro Pro Glu Pro Val Asp Leu Leu Trp Leu Gln Asp
                 165                170                175
Ala Val Pro Leu Ala Thr Ala Pro Gly His Gly Pro Gln Arg Ser Leu
             180                185                190
His Val Pro Gly Leu Asn Lys Thr Ser Ser Phe Ser Cys Glu Ala His
             195                200                205
Asn Ala Lys Gly Val Thr Thr Ser Arg Thr Ala Thr Ile Thr Val Leu
210                215                220
Pro Gln Gln Pro Arg Asn Leu His Leu Val Ser Arg Gln Pro Thr Glu
225                230                235                240
Leu Glu Val Ala Trp Thr Pro Gly Leu Ser Gly Ile Tyr Pro Leu Thr
                 245                250                255
His Cys Thr Leu Gln Ala Val Leu Ser Asp Asp Gly Met Gly Ile Gln
             260                265                270
Ala Gly Glu Pro Asp Pro Pro Glu Glu Pro Leu Thr Ser Gln Ala Ser
             275                280                285
Val Pro Pro His Gln Leu Arg Leu Gly Ser Leu His Pro His Thr Pro
             290                295                300
Tyr His Ile Arg Val Ala Cys Thr Ser Ser Gln Gly Pro Ser Ser Trp
305                310                315                320
Thr His Trp Leu Pro Val Glu Thr Pro Glu Gly Val Pro Leu Gly Pro
                 325                330                335
Pro Glu Asn Ile Ser Ala Thr Arg Asn Gly Ser Gln Ala Phe Val His
             340                345                350
Trp Gln Glu Pro Arg Ala Pro Leu Gln Gly Thr Leu Leu Gly Tyr Arg
             355                360                365
Leu Ala Tyr Gln Gly Gln Asp Thr Pro Glu Val Leu Met Asp Ile Gly
             370                375                380
Leu Arg Gln Glu Val Thr Leu Glu Leu Gln Gly Asp Gly Ser Val Ser
385                390                395                400
Asn Leu Thr Val Cys Val Ala Ala Tyr Thr Ala Ala Gly Asp Gly Pro
                 405                410                415
Trp Ser Leu Pro Val Pro Leu Glu Ala Trp Arg Pro Gly Gln Ala Gln
             420                425                430
```

```
Pro Val His Gln Leu Val Lys Glu Pro Ser Thr Pro Ala Phe Ser Trp
        435                 440                 445

Pro Trp Trp Tyr Val Leu Leu Gly Ala Val Val Ala Ala Ala Cys Val
    450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
            500                 505                 510

Leu Asn Ser Leu Gly Ile Ser Glu Glu Leu Lys Glu Lys Leu Arg Asp
        515                 520                 525

Val Met Val Asp Arg His Lys Val Ala Leu Gly Lys Thr Leu Gly Glu
    530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
        595                 600                 605

Glu Arg Glu Ser Phe Pro Ala Pro Val Val Ile Leu Pro Phe Met Lys
    610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
        675                 680                 685

Ala Asp Phe Gly Leu Ser Lys Lys Ile Tyr Asn Gly Asp Tyr Tyr Arg
    690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Arg Gly Asn Arg Leu
        755                 760                 765

Lys Gln Pro Ala Asp Cys Leu Asp Gly Leu Tyr Ala Leu Met Ser Arg
    770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Tyr Pro Glu
            820                 825                 830

Pro Pro Gly Ala Ala Gly Gly Ala Asp Pro Thr Gln Pro Asp Pro
    835                 840                 845
```

```
Lys Asp Ser Cys Ser Cys Leu Thr Ala Ala Glu Val His Pro Ala Gly
    850                 855                 860
Arg Tyr Val Leu Cys Pro Ser Thr Thr Pro Ser Pro Ala Gln Pro Ala
865                 870                 875                 880
Asp Arg Gly Ser Pro Ala Ala Pro Gly Gln Glu Asp Gly Ala
                885                 890

<210> SEQ ID NO 10
<211> LENGTH: 888
<212> TYPE: PRT
<213> ORGANISM: Mus musculus

<400> SEQUENCE: 10

Met Gly Arg Val Pro Leu Ala Trp Trp Leu Ala Leu Cys Cys Trp Gly
1               5                   10                  15
Cys Ala Ala His Lys Asp Thr Gln Thr Glu Ala Gly Ser Pro Phe Val
                20                  25                  30
Gly Asn Pro Gly Asn Ile Thr Gly Ala Arg Gly Leu Thr Gly Thr Leu
            35                  40                  45
Arg Cys Glu Leu Gln Val Gln Gly Glu Pro Pro Glu Val Val Trp Leu
    50                  55                  60
Arg Asp Gly Gln Ile Leu Glu Leu Ala Asp Asn Thr Gln Thr Gln Val
65                  70                  75                  80
Pro Leu Gly Glu Asp Trp Gln Asp Glu Trp Lys Val Val Ser Gln Leu
                85                  90                  95
Arg Ile Ser Ala Leu Gln Leu Ser Asp Ala Gly Glu Tyr Gln Cys Met
            100                 105                 110
Val His Leu Glu Gly Arg Thr Phe Val Ser Gln Pro Gly Phe Val Gly
    115                 120                 125
Leu Glu Gly Leu Pro Tyr Phe Leu Glu Glu Pro Glu Asp Lys Ala Val
130                 135                 140
Pro Ala Asn Thr Pro Phe Asn Leu Ser Cys Gln Ala Gln Gly Pro Pro
145                 150                 155                 160
Glu Pro Val Thr Leu Leu Trp Leu Gln Asp Ala Val Pro Leu Ala Pro
                165                 170                 175
Val Thr Gly His Ser Ser Gln His Ser Leu Gln Thr Pro Gly Leu Asn
            180                 185                 190
Lys Thr Ser Ser Phe Ser Cys Glu Ala His Asn Ala Lys Gly Val Thr
    195                 200                 205
Thr Ser Arg Thr Ala Thr Ile Thr Val Leu Pro Gln Arg Pro His His
210                 215                 220
Leu His Val Val Ser Arg Gln Pro Thr Glu Leu Glu Val Ala Trp Thr
225                 230                 235                 240
Pro Gly Leu Ser Gly Ile Tyr Pro Leu Thr His Cys Asn Leu Gln Ala
                245                 250                 255
Val Leu Ser Asp Asp Gly Val Gly Ile Trp Leu Gly Lys Ser Asp Pro
            260                 265                 270
Pro Glu Asp Pro Leu Thr Leu Gln Val Ser Val Pro His Gln Leu
    275                 280                 285
Arg Leu Glu Lys Leu Leu Pro His Thr Pro Tyr His Ile Arg Ile Ser
290                 295                 300
Cys Ser Ser Ser Gln Gly Pro Ser Pro Trp Thr His Trp Leu Pro Val
305                 310                 315                 320
Glu Thr Thr Glu Gly Val Pro Leu Gly Pro Pro Glu Asn Val Ser Ala
                325                 330                 335
```

```
Met Arg Asn Gly Ser Gln Val Leu Val Arg Trp Gln Glu Pro Arg Val
            340                 345                 350
Pro Leu Gln Gly Thr Leu Leu Gly Tyr Arg Leu Ala Tyr Arg Gly Gln
            355                 360                 365
Asp Thr Pro Glu Val Leu Met Asp Ile Gly Leu Thr Arg Glu Val Thr
370                 375                 380
Leu Glu Leu Arg Gly Asp Arg Pro Val Ala Asn Leu Thr Val Ser Val
385                 390                 395                 400
Thr Ala Tyr Thr Ser Ala Gly Asp Gly Pro Trp Ser Leu Pro Val Pro
            405                 410                 415
Leu Glu Pro Trp Arg Pro Gly Gln Gly Gln Pro Leu His His Leu Val
            420                 425                 430
Ser Glu Pro Pro Arg Ala Phe Ser Trp Pro Trp Trp Tyr Val Leu
            435                 440                 445
Leu Gly Ala Leu Val Ala Ala Ala Cys Val Leu Ile Leu Ala Leu Phe
        450                 455                 460
Leu Val His Arg Arg Lys Lys Glu Thr Arg Tyr Gly Glu Val Phe Glu
465                 470                 475                 480
Pro Thr Val Glu Arg Gly Glu Leu Val Val Arg Tyr Arg Val Arg Lys
            485                 490                 495
Ser Tyr Ser Arg Arg Thr Thr Glu Ala Thr Leu Asn Ser Leu Gly Ile
            500                 505                 510
Ser Glu Glu Leu Lys Glu Lys Leu Arg Asp Val Met Val Asp Arg His
        515                 520                 525
Lys Val Ala Leu Gly Lys Thr Leu Gly Glu Gly Glu Phe Gly Ala Val
        530                 535                 540
Met Glu Gly Gln Leu Asn Gln Asp Asp Ser Ile Leu Lys Val Ala Val
545                 550                 555                 560
Lys Thr Met Lys Ile Ala Ile Cys Thr Arg Ser Glu Leu Glu Asp Phe
            565                 570                 575
Leu Ser Glu Ala Val Cys Met Lys Glu Phe Asp His Pro Asn Val Met
            580                 585                 590
Arg Leu Ile Gly Val Cys Phe Gln Gly Ser Asp Arg Glu Gly Phe Pro
        595                 600                 605
Glu Pro Val Val Ile Leu Pro Phe Met Lys His Gly Asp Leu His Ser
        610                 615                 620
Phe Leu Leu Tyr Ser Arg Leu Gly Asp Gln Pro Val Phe Leu Pro Thr
625                 630                 635                 640
Gln Met Leu Val Lys Phe Met Ala Asp Ile Ala Ser Gly Met Glu Tyr
            645                 650                 655
Leu Ser Thr Lys Arg Phe Ile His Arg Asp Leu Ala Ala Arg Asn Cys
            660                 665                 670
Met Leu Asn Glu Asn Met Ser Val Cys Val Ala Asp Phe Gly Leu Ser
        675                 680                 685
Lys Lys Ile Tyr Asn Gly Asp Tyr Tyr Arg Gln Gly Arg Ile Ala Lys
        690                 695                 700
Met Pro Val Lys Trp Ile Ala Ile Glu Ser Leu Ala Asp Arg Val Tyr
705                 710                 715                 720
Thr Ser Lys Ser Asp Val Trp Ser Phe Gly Val Thr Met Trp Glu Ile
            725                 730                 735
Ala Thr Arg Gly Gln Thr Pro Tyr Pro Gly Val Glu Asn Ser Glu Ile
            740                 745                 750
```

```
Tyr Asp Tyr Leu Arg Gln Gly Asn Arg Leu Lys Gln Pro Val Asp Cys
        755                 760                 765

Leu Asp Gly Leu Tyr Ala Leu Met Ser Arg Cys Trp Glu Leu Asn Pro
    770             775                 780

Arg Asp Arg Pro Ser Phe Ala Glu Leu Arg Glu Asp Leu Glu Asn Thr
785             790                 795                     800

Leu Lys Ala Leu Pro Pro Ala Gln Glu Pro Asp Glu Ile Leu Tyr Val
            805                 810                     815

Asn Met Asp Glu Gly Gly Ser His Leu Glu Pro Arg Gly Ala Ala Gly
            820                 825                 830

Gly Ala Asp Pro Pro Thr Gln Pro Asp Pro Lys Asp Ser Cys Ser Cys
            835                 840                 845

Leu Thr Ala Ala Asp Val His Ser Ala Gly Arg Tyr Val Leu Cys Pro
    850                 855                 860

Ser Thr Ala Pro Gly Pro Thr Leu Ser Ala Asp Arg Gly Cys Pro Ala
865             870                 875                     880

Pro Pro Gly Gln Glu Asp Gly Ala
                885
```